(12) United States Patent
Hacker et al.

(10) Patent No.: US 6,864,217 B2
(45) Date of Patent: Mar. 8, 2005

(54) HERBICIDAL COMPOSITIONS WITH SUBSTITUTED PHENYLSULFONYLUREAS FOR CONTROLLING WEEDS IN RICE

(75) Inventors: Erwin Hacker, Hocchheim (DE); Hermann Bieringer, Eppstein (DE)

(73) Assignee: Hoechst Schering AgrEvo GmbH, Frankfurt am Main (DE)

( * ) Notice: Subject to any disclaimer, the term of this patent is extended or adjusted under 35 U.S.C. 154(b) by 0 days.

(21) Appl. No.: 10/238,153

(22) Filed: Sep. 10, 2002

(65) Prior Publication Data
US 2003/0191025 A1 Oct. 9, 2003

Related U.S. Application Data

(62) Division of application No. 09/353,701, filed on Jul. 14, 1999, now Pat. No. 6,492,301.

(30) Foreign Application Priority Data

Jul. 16, 1998 (DE) .......................... 198 32 017

(51) Int. Cl.⁷ ................ A01N 43/54; A01N 43/66; A01N 47/36
(52) U.S. Cl. .............. 504/128; 504/132; 504/133; 504/134; 504/135; 504/136
(58) Field of Search .................. 504/128, 132, 504/133, 134, 135, 136, 214, 267

(56) References Cited

U.S. PATENT DOCUMENTS 6,054,410 A * 4/2000 Landes et al. ............ 504/134

FOREIGN PATENT DOCUMENTS

| DE | 42 09 475 | 9/1993 |
| DE | 196 42 082 | 4/1998 |
| DE | 198 34 627 | 12/1998 |
| DE | 198 51 854 | 4/1999 |
| DE | 199 19 951 | 9/1999 |
| WO | WO 92/13845 | 8/1992 |
| WO | WO 95/08919 | 4/1995 |
| WO | WO 95/10507 | 4/1995 |
| WO | WO 96/41537 | 12/1996 |
| WO | WO 97/10714 | 3/1997 |
| WO | WO 98/24320 | 6/1998 |

* cited by examiner

Primary Examiner—S. Mark Clardy
(74) Attorney, Agent, or Firm—Frommer Lawrence & Haug LLP

(57) ABSTRACT

Herbicidal compositions comprising
A) at least one herbicidally active compound from the group of the substituted phenylsulfonylureas of the formula I and their agriculturally accepted, i.e. acceptable and compatible, salts

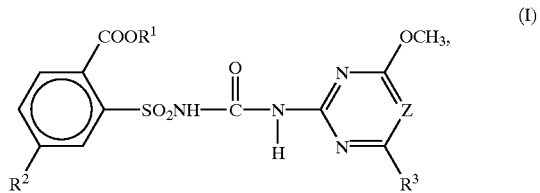

in which
$R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy;
$R^2$ is I or $CH_2NHSO_2CH_3$;
$R^3$ is methyl or methoxy; and
Z is N or CH;
and
B) at least one herbicidally active compound from the group of the compounds consisting of
Ba) herbicides which are selective in rice, mainly against grasses,
Bb) herbicides which are selective in rice, mainly against dicotyledonous harmful plants and cyperaceae,
Bc) herbicides which are selective in rice, mainly against cyperaceae, and
Bd) herbicides which are selective in rice, mainly against grasses an dicotyledenous harmful plants and also against harmful cyperaceae plants.

39 Claims, No Drawings

HERBICIDAL COMPOSITIONS WITH SUBSTITUTED PHENYLSULFONYLUREAS FOR CONTROLLING WEEDS IN RICE

RELATED APPLICATIONS

This application is a divisional application of U.S. Ser. No. 09/353,701, filed Jul. 14, 1999, now U.S. Pat. No. 6,492,301, now allowed and herein incorporated by reference, which claims priority to German application No. 198 32 017.5, filed on Jul. 16, 1998.

The invention relates to the technical field of crop protection agents and relates in particular to herbicidal compositions comprising compounds of the formula I

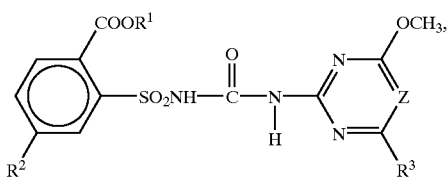

in which $R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy;

$R^2$ is I, or $CH_2NHSO_2CH_3$;

$R^3$ is methyl or methoxy; and z is N or CH;

and/or their salts, which are highly suitable, for controlling weeds in rice which have hitherto been difficult to control with individual herbicides, in particular grass-like, dicotyledonous and/or cyperaceae-like weeds in rice or transgenic crops of rice.

For the relevant prior art, the following publications may be mentioned:

WO 92/13845 (PCT/EP92/00304)=D1,
WO 95/10507 (PCT/EP94/03369)=D2,
WO 96/41537 (PCT/EP96/02443)=D3 and
WO 98/24320 (PCT/EP97/06416)=D4.

D1 discloses iodinated arylsulfonylureas of the formula I and salts thereof,

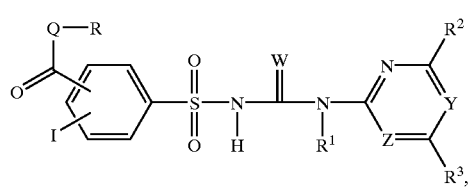

where the formula I embraces a large number of possible individual compounds, owing to the extensive and broad definition of the radicals Q, W, Y, Z, R, $R^1$, $R^2$ and $R^3$.

D1 indicates, in a general manner, that the compounds of the formula I may be used together with other herbicides. This indication is followed by an exemplary enumeration of more than about 250 different standard active compounds. Information about a particular reason and purpose of joint application is, except for the fact that the substances are mentioned, not given in D1, nor a motivation for targetted selection and combination of certian active compounds.

D2 discloses phenylsulfonylureas of the formula 2 and salts thereof

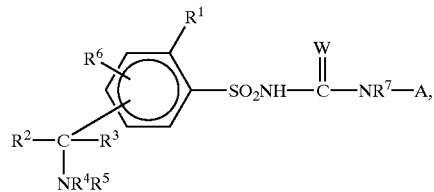

where, once more, the formula 2 embraces a very large number of possible individual compounds, owing to the extensive and broad definition of the radicals A, W, $R^1$, $R^2$, $R^3$, $R^4$, $R^5$, $R^6$ and $R^7$.

In Table 1 of D2, compounds of the formula (2a) are listed

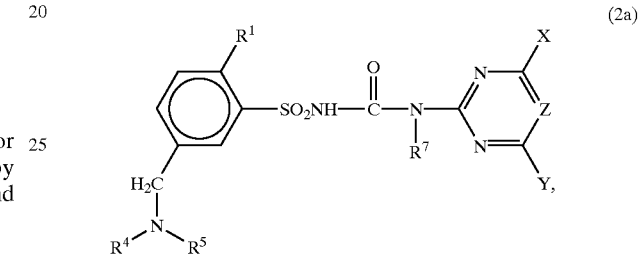

where the examples Nos. 105, 209, 217, 395, 399, 403, 407, 497 and 536 relate to those compounds of the formula 2a in which Z is CH, X and Y is methoxy, $R^7$ is hydrogen, $R^1$ is alkoxycarbonyl, $R^4$ is hydrogen and $R^5$ is a radical which contains a sulfonyl group ($SO_2CH_3$, $SO_2NHCH_3$, $SO_2N(CH_3)_2$, $SO_2N(CH_3)_2$, $SO_2CH_2F$, $SO_2CF_3$, $SO_2C_2H_5$, $SO_2$—n—$C_3H_7$, preferably $SO_2CH_3$).

D2 gives biological examples for the compounds mentioned individually above in that, in a general manner, it is mentioned that the compounds of Examples 105, 217 and 536—in addition to a large number of other compounds—have very good activity against harmful plants such as *Sinapis alba, Stellaria media, Chrysanthemum segetum* and *Lolium multiflorum* when applied pre- or post-emergence at an application rate of from 0.3 kg to 0.005 kg of active substance per hectare. In the abovementioned international laid-open publication, the crop plant compatibility of the compounds of the formula 2 or 2a is not demonstrated by any examples.

Furthermore, D2 indicates, in a general manner, the possibility of using the compounds of the formula 2 together with other herbicides. This indication is followed by an exemplary list of more than about 250 different standard active compounds. The proposed combinations seem to have been given more or less at random, and they do not teach anything that exceeds the fact that herbicides can be combined in principle.

D3 discloses herbicidal compositions comprising

A) at least one herbicidally active compound from the group of the substituted phenylsulfonylureas of the formula 3

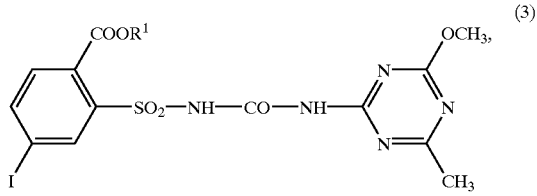

(3)

in which
R$^1$ is (C$_1$–C$_8$)-alkyl, (C$_3$–C$_4$)-alkenyl, (C$_3$–C$_4$)-alkynyl or (C$_1$–C$_4$)-alkyl, which is mono- to tetrasubstituted by radicals from the group consisting of halogen and (C$_1$–C$_2$)-alkoxy
and
B) at least one herbicidally active compound from the group of the compounds consisting of
Ba) herbicides that are selective in cereals and/or in maize against grasses,
Bb) herbicides that are selective in cereals and/or maize against dicotyledonous plants,
Bc) herbicides that are selective in cereals and/or maize against grasses and dicotyledonous plants and
Bd) herbicides that are nonselective in non-crop land and/or selective in transgenic crops against wheat-grasses and broad-leaved weeds.

D3 discloses, in particular, combinations of the sulfonylurea of the formula 3 with fenoxaprop, fenoxaprop-P, isoproturon, diclofop, clodinafop, mixtures of clodinafop and cloquintocet, chlortoluron, methabenzthiazuron, imazamethabenz, tralkoxydim, difenzoquat, flamprop, flamprop-M, pendimethalin, nicosulfuron, rimsulfuron, primisulfuron, mecoprop, mecoprop-P, MCPA, dichlorprop, dichlorprop-P, 2,4-D, dicamba, fluroxypyr, ioxynil, bromoxynil, bifenox, fluoroglycofen, acifluorfen, lactofen, fomesafen, oxyfluorfen, ET-751, azoles according to WO/08999, diflufenican, bentazon, metolachlor, metribuzin, atrazin, terbuthylazin, alachlor, acetochlor, dimethenamid, amidosulfuron, metsulfuron, tribenuron, thifensulfuron, triasulfuron, chlorsulfuron, prosulfuron or CGA-152005, sulfonylureas according to WO 94/10154, flupyrsulfuron (DPX-KE459), sulfosulfuron (MON37500), KIH-2023, glufosinate, glufosinate-P or glyphosate.

The particular combinations that are mentioned are synergistic, the area of use is limited to cereals and maize.

D4 discloses combinations comprising:
A) at least one compound from the group of the substituted phenylsulfonylureas of the formula 4 and their agriculturally accepted salts

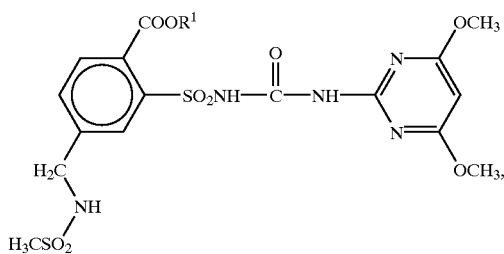

(4)

in which
R$^1$ is (C$_1$–C$_8$)-alkyl, (C$_3$–C$_4$)-alkenyl, (C$_3$–C$_4$)-alkynyl or (C$_1$–C$_4$)-alkyl, which is mono- to tetrasubstituted by radicals from the group consisting of halogen and (C$_1$–C$_2$)-alkoxy
and
B) at least one herbicidally active compound from the group of the compounds consisting of Ba) herbicides which are selective in cereals against grasses,
Bb) herbicides which are selective in cereals against dicotyledonous plants,
Bc) herbicides which are selective in cereals against grasses and dicotyledonous plants and
Bd) herbicides which are nonselective in non-crop land or in perennial crops (plantations) and/or selective in transgenic crops against wheat grasses and broad-leaved weeds.

In particular, combinations with fenoxaprop, fenoxaprop-P, isoproturon, diclofop, clodinafop, mixtures of clodinafop and cloquintocet, chlortoluron, methabenzthiazuron, imazamethabenz, tralkoxydim, difenzoquat, flamprop, flamprop-M, pendimethalin, mecoprop, mecoprop-P, MCPA, dichlorprop, dichlorprop-P, 2,4-D, dicamba, fluroxypyr, ioxynil, bromoxynil, bifenox, fluoroglycofen, lactofen, fomesafen, oxyfluorfen, ET-751, azoles according to WO 94/08999, F 8426, diflufenican, bentazon, metribuzin, metosulam, flupoxam, prosulfocarb, flurtamone, amidosulfuron, metsulfuron, tribenuron, thifensulfuron, triasulfuron, chlorsulfuron, sulfonylureas according to WO 94/10154, sulfonylureas according to WO 92/13845, flupyrsulfuron (DPX-KE459), MON 48500, sulfosulfuron (MON37500), glufosinate, glufosinate-P or glyphosate are known.

Most of the sulfonylureas known from D1 and D2 according to the formulae 1 and 2 have useful to good activity against a broad spectrum of mono- and dicotyledonous harmful plants of economic importance, and even weeds which are encountered under the specific cultivation conditions in rice, such as, for example, *Sagittaria, Alisma, Eleocharis, Scirpus, Cyperus* etc., are controlled with the aid of active compounds of the formulae 1, 2 and 3; however, for optimum control of thee spectrum of mono- and dicotyledonuos weeds encountered in agricultural practice especially in rice, the individual active compounds are frequently insufficient. Moreover, the synergistic combinations of D3 or D4 can generally not be used with above-average success in rice. At least, this could not be expected with a more than average probability, in particular because the useful plant rice is, to a not unconsiderable extent, damaged by most of the combinations known from D3 or D4, so that these are not suitable for use in crops of rice.

Moreover, there exist, in particular in rice, a number of economically very important monocotyledonous weeds, such as, for example, primarily *Echinochloa crus-galli, Ischaenum* ssp. or *Leptochloa* which cannot be controlled in a satisfactory manner by using just the prior art rice herbicides or mixtures thereof. In particular from the rice crops in Japan and Southeast Asia, we know weeds such as *Sagittaria* spp., *Eleocharis* spp., for example *Eleocharis kuroguwai, Cyperus serotinus, Scirpus juncoides*, but also other weed species, which predominantly germinate from resting organs in the soil and are therefore more difficult to control than weeds which germinate from seeds, and also broad-leaved species which are not simple to control in an optimum manner in the entire width of the weed spectrum.

Furthermore, resistant species (inter alia of *Cyperus* ssp. or *Echinochloa* ssp.) which in many cases can no longer be controlled with individual active compounds and even with customary combinations are found increasingly.

With respect to the prior art mentioned and discussed herein, it was therefore the object of the invention to provide mixtures having herbicidal activity to enable the practitioner to control the weed spectrum or individual weed species which are difficult to control in rice with a single application or a few applications of herbicides. Furthermore, the mixtures of essentially known herbicidally active compounds are intended to close so-called "activity gaps" and, if possible, to reduce simultaneously the application rates of the individual active compounds. Moreover, it was the object to provide combinations which permit a very long duration of action to be obtained. Finally, the combinations are also intended to permit the effective control of resistant species.

Surprisingly, it has been found that these objects, inter alia, are achieved by herbicidal compositions having the features of claim 1. Accordingly, the invention provides herbicidal compositions, comprising A) at least one herbicidally active compound from the group of the substituted phenylsulfonylureas of the formula I and their agriculturally accepted, i.e. acceptable and compatible, salts

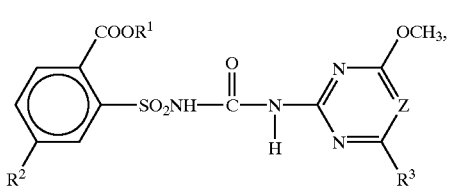

in which
$R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy;
$R^2$ is I or $CH_2NHSO_2CH_3$;
$R^3$ is methyl or methoxy; and
Z is N or CH;
and
B) at least one herbicidally active compound from the group of the compounds consisting of
Ba) herbicides which are selective in rice, mainly against grasses,
Bb) herbicides which are selective in rice, mainly against dicotyledonous harmful plants and cyperaceae,
Bc) herbicides which are selective in rice, mainly against cyperaceae,
and
Bd) herbicides which are selective in rice, mainly against grasses and dicotyledonous harmful plants and also against harmful cyperaceae plants,
with the proviso that
i) compositions comprising
A') at least one compound from the group of the substituted phenylsulfonylureas of the formula I' and their agriculturally accepted salts

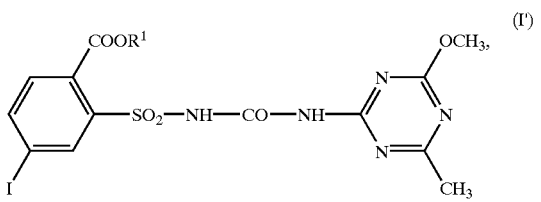

in which
$R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from group consisting of halogen and $(C_1-C_2)$-alkoxy
in combination with , B') fenoxaprop, pendimethalin, nicosulfuron, mecoprop, MCPA, 2,4-D, dicamba, acifluorfen, azoles of the formula III

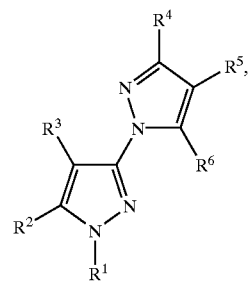

in which $R^1$ is $(C_1-C_4)$-alkyl, $R^2$ is $(C_1-C_4)$-alkyl, $(C_1-C_4)$-alkylthio or $(C_1-C_4)$-alkoxy, each radical of which may be substituted by one or more halogen atoms, or $R^1$ and $R^2$ together form the group $(CH_2)_m$ where m=3 or 4, $R^3$ is hydrogen or halogen, $R^4$ is hydrogen or $(C_1-C_4)$-alkyl, $R^5$ is hydrogen, nitro, cyano or one of the groups $—COOR^7$, $—C(=X)NR^7R^8$ or $—C(=X)R^{10}$, $R^6$ is hydrogen, halogen, cyano, $(C_1-C_4)$-alkyl, $(C_1-C_4)$-alkylthio or $—NR^{11}R^{12}$, $R^7$ and $R^8$ are identical or different and are hydrogen or $(C_1-C_4)$-alkyl, or $R^7$ and $R^8$ together with the nitrogen to which they are attached form a saturated 5- or 6-membered carbocyclic ring, $R^{10}$ is hydrogen or $(C_1-C_4)$-alkyl, where the latter may be unsubstituted or substituted by one or more halogen atoms, and $R^{11}$ and $R^{12}$ are identical or different and are hydrogen, $(C_1-C_4)$-alkyl or $(C_1-C_4)$-alkoxycarbonyl, where $R^{11}$ and $R^{12}$ together with the nitrogen to which they are attached may form a 3-, 5- or 6-membered carbocyclic or aromatic ring in which one carbon atom may optionally be replaced by an oxygen atom, bentazon, metsulfuron, triasulfuron, ioxynil, acetochlor, metolachlor, oxyfluorfen or KIH-2023, as the only herbicidally active compounds and ii) compositions which comprise
A") at least one compound from the group of the substituted phenylsulfonylureas of the formula I" and their agriculturally accepted salts

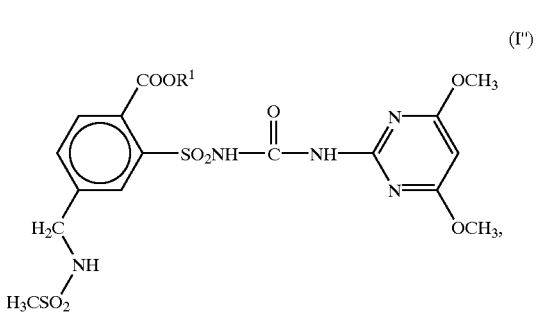

(I'')

in which
R¹ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy in combination with B'')fenoxaprop, pendimethalin, mecoprop, MCPA, 2,4-D, dicamba, a compound of the abovementioned formula III, bentazon, triasulfuron, ioxynil, metosulam, oxyfluorfen or metsulfuron as the only herbicidally active compounds, are excluded.

The combinations according to the invention of herbicidally active compounds of types A and B permit, in a particularly advantageous manner, the control of the weed spectrum required by the practitioner to be achieved, and even individual species which are difficult to control are covered. Furthermore, using the combinations according to the invention, it is possible to reduce the active compound application rates of the individual combination partners contained in the combination considerably, permitting more economical problem solutions by the user.

Finally, it was surprisingly possible to achieve activity increases which exceed the expected degree, and the herbicidal compositions of the invention consequently displayed extensive synergistic activities.

Besides, it is also possible to control many resistant species in an excellent manner.

The boundary conditions i) and ii) (disclaimers with respect to product protection) take into account prior art combinations; however, these previously published combinations did not permit any conclusions with respect to the suitability of the combined preparations in rice applications to be drawn.

Specifically, the disclaimer i) avoids the combinations of one or more type A compounds and a type B compound which are already known from D3, their area of use unambiguously being different from the use of the combinations according to the present invention, and the subject matter of D3 and the present invention therefore being clearly differentiated from one another. While D3 describes combinations with herbicides for use in cereals or maize, the present invention relates to combinations for use in rice.

The disclaimer ii) defines the novelty with respect to D4, which relates to combinations having a type B compound for use in cereals. Here, likewise, the intended uses of the combination are clearly different from the intended uses in accordance with the present invention.

The compounds of type A (formula I) can form salts in which the hydrogen of the —SO₂—NH— group is replaced by an agriculturally suitable cation. These salts are, for example, metal salts, in particular alkali metal salts (for example Na or K salts) or alkaline earth metal salts, or else ammonium salts or salts with organic amines. Salt formation can also be achieved by adding a strong acid to the heterocycle moiety of the compounds of the formula I. Acids which are suitable for this purpose are, for example, HCl, HNO₃, trichloroacetic acid, acetic acid or palmitic acid.

Particularly advantageous type A compounds are those in which the salt of the herbicide of the formula (I) is formed by replacing the hydrogen of the —SO₂—NH— group by a cation from the group of the alkali metals, alkaline earth metals and ammonium, preferably sodium.

If the compounds of the formula I contain one or more asymmetric carbon atoms or else double bonds, which are not specifically indicated in the formula, they nevertheless belong to the type A compounds. All possible stereoisomers, such as enantiomers, diastereomers, Z and E isomers, defined by their specific spatial form are embraced by the formula I and can be obtained from mixtures of the stereoisomers by customary methods, or else by stereoselective reactions in combination with the use of stereochemically pure starting materials. The abovementioned stereoisomers, both in pure form and as mixtures, can accordingly be used according to the invention.

In a first distinguished variant of the invention, compounds of group Aa) are of particular interest as combination partners of type A for the combination of the invention, these compounds being compounds of the formula I in which R¹ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy, R² is iodine, R³ is methyl and Z is N.

In principle, the phenylsulfonylureas of the formula I which carry iodine substituents in the 4-position of the phenyl ring are included, for example, in the formula 1 from WO 92/13845, and their suitability as synergism partners for herbicides to be used in cereals or maize is likewise already part of the prior art (cf. D3); however, their excellent suitability for use as combination partners for synergistic mixtures with other herbicides, which are used in rice, is not disclosed in the prior art. In particular, there are no indications in the published literature that combinations of compounds of group Aa), i.e. the relatively limited and clearly defined group of the 4-iodo-2-[3-(4-methoxy-6-methyl-1,3,5-triazin-2-yl)ureidosulfonyl]benzoates, which are optionally present in the form of their salts, with rice herbicides have such an exceptional rank in the control of the most important harmful plants in rice crops. Here, it also has to be taken into consideration, in particular, that using a combination in crops of maize or cereals does not allow an extrapolation to the effect in crops of rice. Even if the compounds of group Aa) on their own are suitable for controlling harmful plants and rice, it is not possible to predict with a good or even some chance of success whether combinations with other rice herbicides permit, in the control of harmful plants, activity increases which exceed the additive activity.

Combination partners of type A which are of great interest for the combinations of the invention are compounds or their salts of group Aa) in which in the formula I R¹ is methyl, ethyl, n- or isopropyl, n-, tert-, 2-butyl or isobutyl, n-pentyl, isopentyl, n-hexyl, isohexyl, 1,3-dimethylbutyl, n-heptyl, 1-methylhexyl or 1,4-dimethylpentyl, R² is iodine, R³ is methyl and Z is N.

In a particularly preferred embodiment, the herbicidal compositions according to the invention comprise a type A compound from group Aa) of the formula I or their salt, where R¹ is methyl, R² is iodine, R³ is methyl and Z is N.

A special combination partner is the compound A1) methyl 4-iodo-2-[3-(4-methoxy-6-methyl-1,3,5-triazin-2-yl)ureidosulfonyl]benzoate:

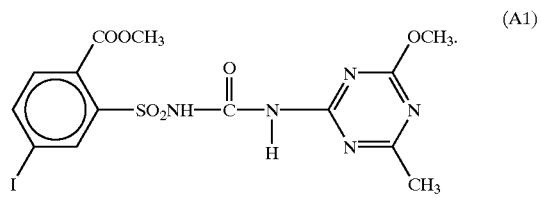

(A1)

A combination partner which, in certain cases, is even more advantageous is the sodium salt of the compound A1) which is to be referred to as A1*).

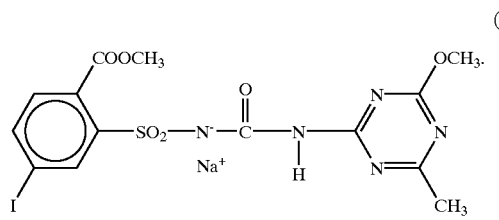

(A1*)

In a further embodiment of the invention, preference is given to using sulfonylureas of the formula I which carry a methylsulfonylamidomethyl substituent in the 5-position of the phenyl ring as compounds of type A). The group Ab) is formed by compounds of the formula I in which $R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals from the group consisting of halogen and $(C_1-C_2)$-alkoxy, $R^2$ is $CH_2NHSO_2CH_3$, $R^3$ is methoxy and Z is CH.

The specific sulfonylureas of group Ab) are, in combination with other herbicides of type B), outstandingly suitable for controlling weed species which are difficult to control in crops of rice effectively. In particular, unexpected specific activity effects against resistant harmful grasses are achieved here.

Of particular interest for the combinations of the invention are, as combination partners of type A compounds of the general formula I from group Ab) or their salts in which $R^1$ is methyl, ethyl, n- or isopropyl, n-, tert-, 2 butyl or isobutyl, n-pentyl, isopentyl, n-hexyl, isohexyl, 1,3-dimethylbutyl, n-heptyl, 1-methylhexyl or 1,4-dimethylpentyl, $R^2$ is $CH_2NHSO_2CH_3$, $R^3$ is methoxy and Z is CH.

In a very particularly preferred embodiment, the herbicidal compositions according to the invention comprise a type A compound from group Ab) of the general formula I or a salt thereof in which $R^1$ is methyl, $R^2$ is $CH_2NHSO_2CH_3$, $R^3$ is $OCH_3$ and Z is CH.

Particular combination partners include the compounds A2):

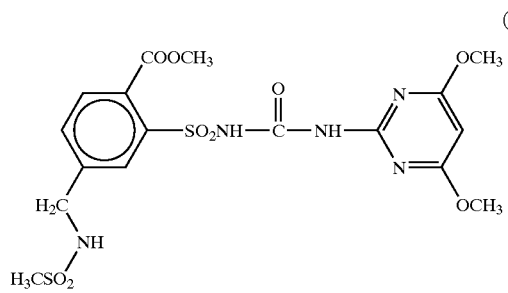

(A2)

and A3)

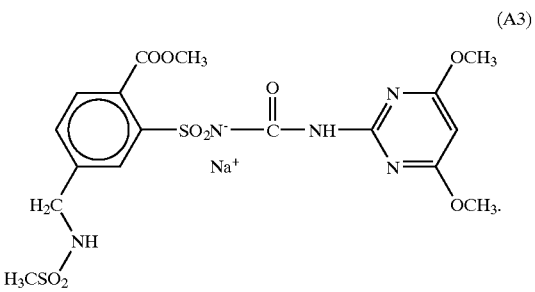

(A3)

The combinaton partners of type B are generally standard herbicides; however, they have been selected using certain criteria. Thus, without exception they are herbicides which are selective in rice against undesirable plants. The harmful plants which are to be controlled here especially include grasses and dicotyledonous plants/cyperaceae. The notation "dicotyledonous plants/cyperaceae" is meant to express that the activity is against dicotyledonous plants and cyperaceae, but that the activity against dicotyledonous plants is in the foreground.

With respect to the activity of the standard herbicides of type B, it is possible to categorize them with respect to which plants are mainly controlled.

Thus, some of the type B herbicides are predominantly, or almost exclusively, active against grasses (subgroup Ba)), others are mainly active against dicotyledonous plants and cyperaceae (subgroup Bb)), others are mainly active against cyperaceae (subgroup Bc)), and another group shows activity both against grasses and against dicotyledonous plants/cyperaceae (subgroup Bd)).

In each case, however, an optimized activity spectrum results for the combination according to the invention by complementation and intensivation of the herbicidal properties of the compounds of type A.

Considering what was said above, a particular embodiment of the herbicidal composition of the invention comprises, as herbicides of type B, one or more herbicides from the group Ba) which are selective in rice against grasses, which includes herbicidally active anilides, in particular chloroacetanilides, thiocarbamates, quinolincarboxylic acids, cyclohexanediones and cyclohexanedione oximes, tetrazoles, organophosphorus compounds, 2-(4-Aryloxyphenoxy)propionic acids, preferably their esters, ureas, pyridinecarbothioates, butyramides, menthyl benzyl ethers and triazoles.

In another very particularly advantageous embodiment, the herbicidally active mixture of the invention comprises, as herbicides of type B, one or more herbicides, which are selective in rice against grasses, from the group consisting of B1) butachlor,

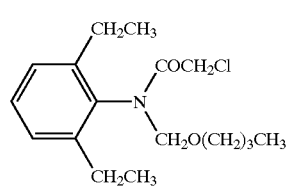

N-(butoxymethyl)-2-chloro-N-(2,6-diethylphenyl) acetamide, Pesticide Manual, 10th Ed. 1994, pp.130–131;

B2) butenachlor,

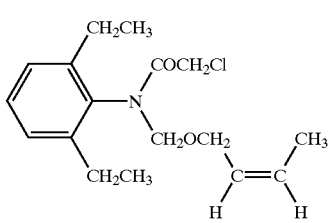

(Z)-2-chloro-N-[(2-butenyloxy)methyl]-N-(2,6-diethylphenyl)acetamide, Pesticide Manual, 10th Ed. 1994, pp.132–133;

B3) thenylchlor

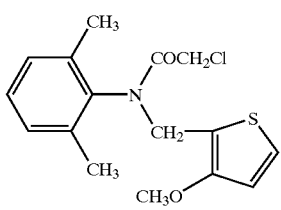

2-chloro-N-(2,6-dimethylphenyl)-N-[(3-methoxy-2-thienyl)methyl]acetamide Pesticide Manual, 10th Ed. 1994, pp.971–972;

B4) pretilachlor

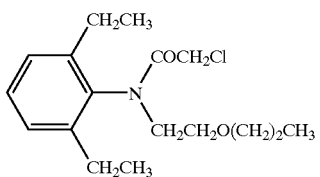

2-chloro-N-(2,6-diethylphenyl)-N-(2-propoxyethyl)acetamide Pesticide Manual, 10th Ed. 1994, pp.828–829;

B5) mefenacet

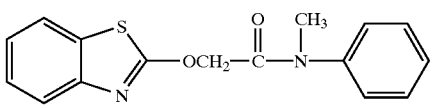

2-(2-benzothiazolyloxy)-N-methyl-N-phenylacetamide Pesticide Manual, 10th Ed. 1994, pp.649–650;

B5a) BAY FOE 5043

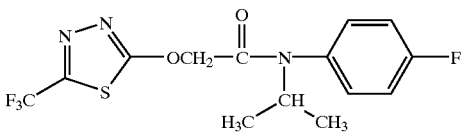

4'-fluoro-N-isopropyl-2-(5-trifluoromethyl-1,3,4-thiadiazol-2-yloxy)acetanilide Pesticide Manual, 11th Ed. 1997, pp.82–83;

B6) naproanilide

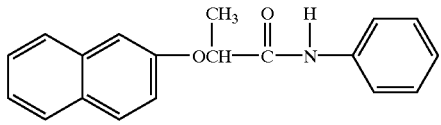

2-(2-naphthalenyloxy)-N-phenylpropanamide Pesticide Manual, 10th Ed. 1994, p.722;

B7) propanil

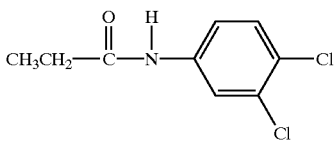

N-(3,4-dichlorophenyl)propanamide Pesticide Manual, 10th Ed. 1994, pp.845–846;

B8) etobenzanide

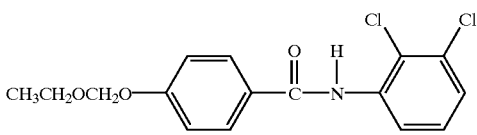

N-(2,3-dichlorophenyl)-4-(ethoxymethoxy)benzamide Pesticide Manual, 10th Ed. 1994, pp.417–418;

B9) dimepiperate

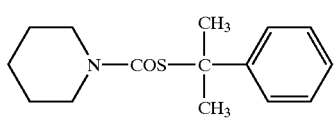

S-(1-methyl-1-phenylethyl)1-piperidincarbothioate Pesticide Manual, 10th Ed. 1994, pp.341–342;

B10) molinate

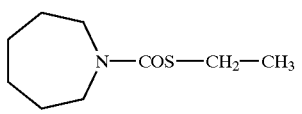

S-ethyl hexahydro-1H-azepin-1-carbothioate Pesticide Manual, 10th Ed. 1994, pp.706–707;

B11) thiobencarb

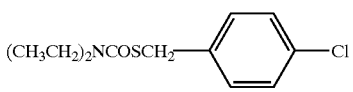

S-[(4-chlorophenyl)methyl]diethylcarbamothioate Pesticide Manual, 10th Ed. 1994, pp.979–980;

B12) pyributicarb

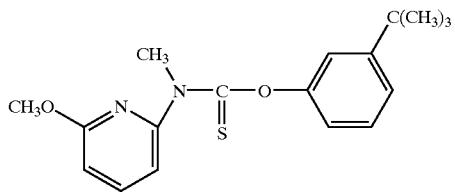

O-[3-(1,1-dimethylethyl)phenyl](6-methoxy-2-pyridinyl) methylcarbamothioate Pesticide Manual, 10th Ed. 1994, pp.878–879;

B13) quinclorac

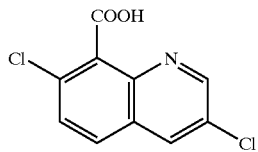

3,7-dichloro-8-quinolincarboxylic acid Pesticide Manual, 10th Ed. 1994, pp.892–893;

B14) cyclohexanediones of the formula II

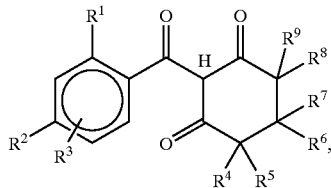

(II)

in which $R^1$ is halogen, $(C_1-C_4)$-alkoxy, $(C_1-C_4)$-alkyl, $(C_1-C_4)$-haloalkyl, —$NO_2$, —CN or $S(O)_n R^{10}$;

$R^2$ and $R^3$ independently of one another are hydrogen, halogen, $(C_1-C_4)$-alkyl, $(C_1-C_4)$-alkoxy, $(C_1-C_4)$-haloalkoxy, $(C_1-C_4)$-haloalkyl, —$NO_2$, —CN or $S(O)_m R^{11}$, —$NR^{12}R^{13}$, —$NR^{14}$—CO—$R^{15}$;

$R^4$ is hydrogen, $(C_1-C_4)$-alkyl or —CO—O—$(C_1-C_4)$-alkyl;

$R^5$, $R^6$, $R^7$, $R^8$, $R^9$ independently of one another are hydrogen or $(C_1-C_4)$-alkyl or —CO—$R^{16}$;

$R^{10}$ is $(C_1-C_4)$-alkyl, $(C_1-C_4)$-haloalkyl or $(C_1-C_4)$-alkoxy;

$R^{11}$ is $(C_1-C_4)$-alkyl, $(C_1-C_4)$-haloalkyl, phenyl, benzyl or —$NR^{17}R^{18}$;

$R^{12}$ and $R^{13}$ independently of one another are hydrogen or $(C_1-C_4)$-alkyl;

$R^{14}$ is hydrogen or $(C_1-C_4)$-alkyl:;

$R^{15}$ is $(C_1-C_4)$-alkyl;

$R^{16}$ is hydrogen, $(C_1-C_4)$-alkyl, $(C_1-C_4)$-haloalkyl or $(C_1-C_4)$-alkoxy;

$R^{17}$ and $R^{18}$ independently of one another are hydrogen or $(C_1-C_4)$-alkyl; and n and m independently of one another are 0, 1 or 2, particularly preferably B14a) ICIA0051=sulcotrione

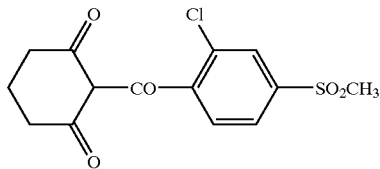

2-[2-chloro-4-(methylsulfonyl)benzoyl]-1,3-cyclohexanedione Pesticide Manual, 10th Ed. 1994, pp.577–578;

B15) cycloxydim

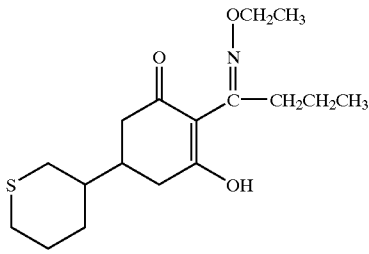

(±)-2-[1-(ethoxyimino)butyl]-3-hydroxy-5-thian-3-yl-cyclohex-2-enone Pesticide Manual, 11th Ed. 1997, pp.290–291;

B16) sethoxydim

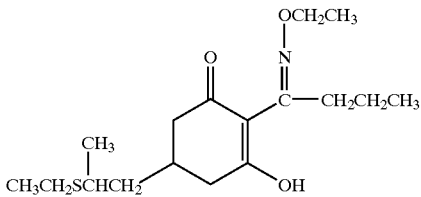

(±)-(EZ)-2-(1-ethoxyiminobutyl)-5-[2-(ethylthio)-propyl]-3-hydroxycyclohex-2-enone Pesticide Manual, 11th Ed. 1997, pp.1001–1003;

B17) NBA 061=fentrazamide or BAY YRC 2388

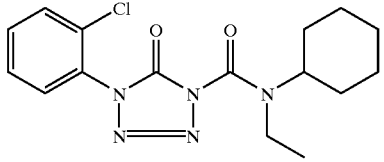

4-(2-chlorophenyl)-5-oxo-4, 5-dihydro-tetrazole-1-carboxylic acid cyclohexyl-ethyl-amide B18) piperophos

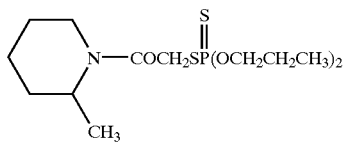

S-[2-(2-methyl-1-piperidinyl)(2-oxoethyl]O,O-dipropyl phosphorodithioate Pesticide Manual, 10th Ed. 1994, pp.818–819;

B19) anilofos

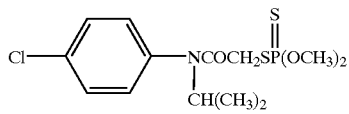

S-[2-[(4-chlorophenyl)(1-methylethyl)amino]-2-oxo-ethyl]O,O-dimethylphosphorodithioate Pesticide Manual, 10th Ed. 1994, pp.44–45;

B20) fenoxaprop, fenoxaprop-P

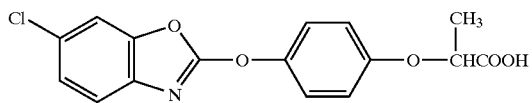

(±)-2-[4-(6-chloro-1,3-benzoxazol-2-yloxy)phenoxy]-propionic acid, including, inter alia, the use form as fenoxaprop-ethyl,

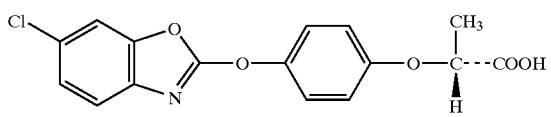

(R)-2-[4-(6-chloro-1,3-benzoxazol-2-yloxy)phenoxy]-propionic acid, including, inter alia, the most popular use form fenoxaprop-P-ethyl, where the abovementioned compounds B20) are known from Pesticide Manual, 10th Ed. 1994, pp.439–441 and 441–442;

B21) haloxyfop

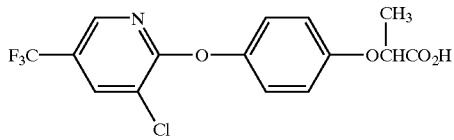

(±)-2-[4-[[3-chloro-5-(trifluoromethyl)-2-pyridinyl]-oxy]phenoxy]propionic acid, including, inter alia, the use form as haloxyfop-etotyl, haloxyfop-methyl, haloxyfop-methyl [(R)-isomer], where the abovementioned compounds B21) are known from Pesticide Manual, 10th Ed. 1994, pp.551–554;

B22) Cyhalofop-butyl=DEH 112

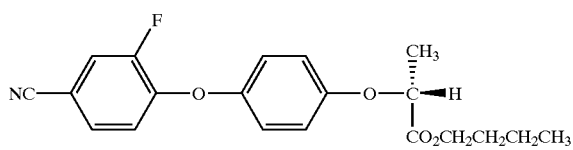

butyl(R)-2-[4-(4-cyano-2-fluorophenoxy)phenoxy]-propionate, where the abovementioned compound B22) is known from Pesticide Manual, 11th Ed. 1997, pp.297–298,

B23) JC-940

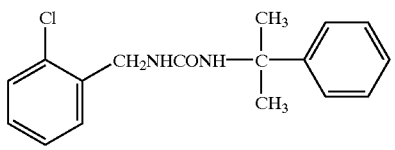

3-(2-chlorophenylmethyl)-1-(1-methyl-1-phenyl-ethyl) urea Japanese Laid-Open Application J-6 0087 254;

B24) dithiopyr

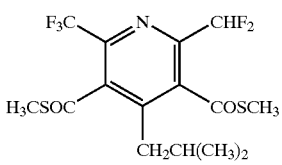

S,S'-dimethyl-2-(difluoromethyl)-4-(2-methylpropyl)-6-(trifluoromethyl)-3,5-pyridindicarbothioate Pesticide Manual, 10th Ed. 1994, pp.375–376;

B25) bromobutide

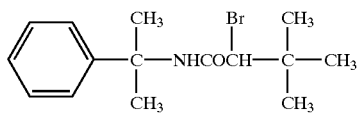

2-bromo-3,3-dimethyl-N-(1-methyl-1-phenylethyl)-butyramide Pesticide Manual, 10th Ed. 1994, pp.117–118;

B26) cinmethylin

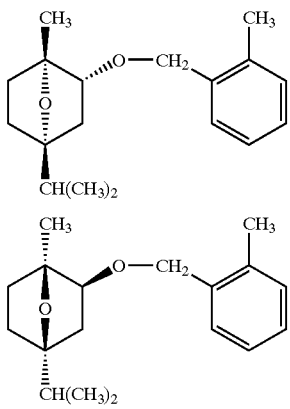

Exo-(±)-1-methyl-4-(1-methylethyl)-2-[(2-methyl-phenyl)methoxy]-7-oxabicyclo[2.2.1]heptane Pesticide Manual, 10th Ed. 1994, pp.210–211;

and

B27) CH-900

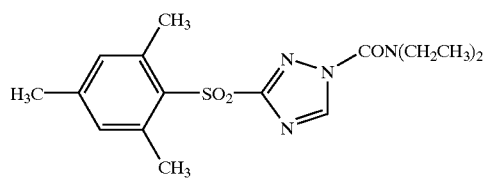

N,N-diethyl-3-mesitylsulfonyl-1H-1,2,4-triazol-1-carboxamide Pesticide Manual, 10th Ed. 1994, pp.162–163.

The abovementioned compounds B1) to B8) are anilides some of which belong to the subgroup of the chloroacetanilides (compounds B1) to B4) ). The compounds B1) to B8) of the subgroup Ba) are mainly active against harmful grasses.

Specifically, the abovementioned herbicides B1) to B8) are directed against grasses, for example annual grasses. In addition, butachlor also covers broad-leaved weeds in rice, likewise butenachlor, which can additionally be used against aquatic weeds in rice; thenylchlor controls in particular *Echinochloa* spp; whereas *Pretilachlor* is active against numerous seeds.

Mefenacet is active in particular agaginst *Echinochloa crus galli*; the activity spectrum of naproanilide, propanil and etobenzanide covers especially: broad-leaved and grass-like weeds such as *Amaranthus retroflexus, Digitaria* spp., *Echinochloa* spp., *Panicum* spp., *Setaria* spp.; Bay Foe 5043 acts against a wide spectrum of grasses.

The compounds B9) to B12) are thiocarbamates whose activity unfolds best when controlling grasses in rice, mainly *Echinochloa crus galli* in rice (B9)), broad-leaved and grass-like weeds in rice, in particular *Echinochloa* spp. (B10)), monocotyledonous and annual broad-leaved weeds in rice, in particular *Echinochloa, Leptochloa, Cyperus* spp (B11)), annual and perennial grasses in rice, in particular *Echinochloa oryzicol, Cyperus difformis, Monochoria vaginalis, Digitaria ciliaris, Setaria viridis* (B12)).

B13) is a representative of the quinolinecarboxylic acids and is preferably employed for controlling grass-like weeds (*Echinochloa* spp., *Aeschynomene* spp., *Sesbania* spp.) and other weeds in rice.

B14) and B14a) are cyclohexanediones which, in the context of the combinations according to the invention, can surprisingly also be employed in rice against broad-leaved weeds and grasses.

In the wider sense, B15) and B16) also belong to the group of the cyclohexanediones. In particular, they are cyclohexanedione oximes which are preferably used for controlling annual and perennial grasses by the post-emergence method. It is particularly surprising, especially for B15) and B16) that, in combination with type A) compounds, an excellent tolerance in rice applications is achieved, something which is generally not the case when B15) or B16) are applied alone.

The tetrazoles also belong to the group Ba), and they act especially against grasses in rice. An important representative having the abovementioned chemical structure is the compound B17).

A further interesting subgroup of the subgroup Ba) are the organophosphorus compounds. B18) is preferably employed for controlling annual grasses and seeds in rice. B19) has a comparable activity spectrum, i.e.: annual grasses and seeds in rice.

The group Ba) furthermore includes the family of the herbicidally active 2-(4-aryloxyphenoxy)propionic acids. An important representative is B20) whose preferred area of use is against grasses in rice. B21) is likewise employed in the combinations of the invention, usually for controlling annual and perennial grasses. In the context according to the invention, it may also be particularly favorable to apply B20) and/or B21) together with a compound which additionally acts as safener, such as, for example, B22). Of particularly great interest are combinations according to the invention with B22). B22) acts, as acetyl-CoA carboxylase inhibitor, mainly against grasses and is, owing to the different metabolism of rice and weed, particularly well tolerated in rice applications.

Furthermore, the group Ba) includes the family of the herbicidally active ureas. An important representative of this chemical family is the compound B23). It is preferably active against annual and perennial grasses.

Furthermore of interest are the pyridinedicarbothioates, for example the compound B23), being active mainly against annual grasses and broad-leaved weeds in rice.

Another chemical subgroup of the group Ba) relates to the butyramides; particular emphasis is given to the compound B25). Combinations with B25) have proved to be highly suitable for controlling sedges, in particular *Echinochloa* spp., *Eleocharis acicularis* and *Scirpus juncoides* and some broad-leaved weeds in paddyfield rice and upland rice.

Also a member of group Ba) is the chemical grouping of the menthyl benzyl ethers. An important element of this group is the compound B26). It shows excellent activity against weeds in rice, such as *Echinochloa* spp., *Monochoria vaginalis, Cyperus difformis*.

Triazoles likewise have proved, as members of subgroup Ba) and together with compounds of the A type, to be most suitable for suppressing undesirable plant growth, in particular of annual and perennial weeds in paddy rice, such as *Echinochloa oryzicola* and *Cyperus difformis*.

Even though the representatives of the group Ba) have relatively different chemical structures, they still form a homogeneous subgroup, owing to their activity spectrum and to the fact that they are synergists for the compounds of the formula I.

Other compositions which are embraced by the invention are those comprising herbicides of type B from the subgroup Bb) . Here, it is particularly advantageous to use one or more herbicides which are selective in rice mainly against dicotyledonous plants and in some cases also against cyperaceae from the group comprising herbicides of the type of the aryloxyalkylcarboxylic acids and dicamba, nitrodiphenyl ethers, azoles and pyrazoles, sulfonylureas, benzonitriles, pyridinecarboxylic acids and triazoles.

Of particular interest are here herbicidal compositions which, as compound of type B, contain one or more compounds which are selective in rice against dicotyledonous plants and in some cases also cyperaceae, selected from the group consisting of the herbicides

B28) 2,4-D

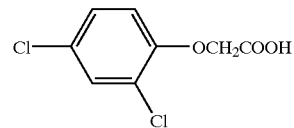

(2,4-Dichlorophenoxy)acetic acid frequently used forms: 2,4-D-butotyl, 2,4-D-butyl, 2,4-D-dimethylammonium, 2,4-D-diolamin, 2,4-D-iso-octyl, 2,4-D-isopropyl, 2,4-D-trolamin, Pesticide Manual, 10th Ed. 1994, pp.271–273,

B29) MCPA

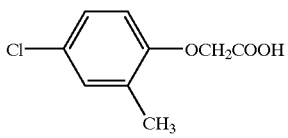

(4-chloro-2-methylphenoxy)acetic acid, frequently used forms are, inter alia, MCPA-butotyl, MCPA-dimethylammonium, MCPA-isooctyl, MCPA-potassium, MCPA-sodium, Pesticide Manual, 10th Ed. 1994, pp.638–640, B30) mecoprop, mecoprop-P

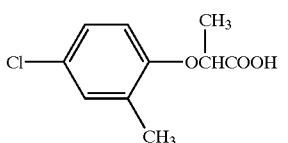

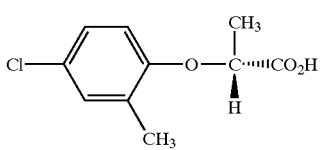

(RS)-2-(4-chloro-o-tolyloxy)propionic acid (R)-2-(4-chloro-o-tolyloxy)propionic acid Pesticide Manual, 10th Ed. 1994, pp.646–647 and 647–648, B31) dicamba

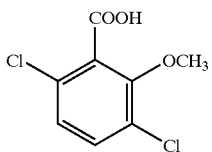

3,6-dichloro-o-anisic acid used, inter alia, as dicamba-dimethylammonium, dicamba-potassium, dicamba-sodium, dicamba-trolamine, Pesticide Manual, 10th Ed. 1994, pp.298–300, B32) acifluorfen

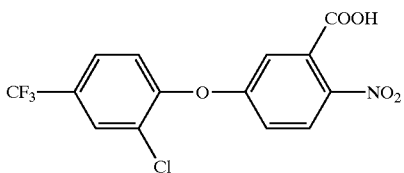

5-(2-chloro-α,α,α-trifluoro-p-tolyloxy)-2-nitrobenzoic acid, also used as acifluorfen-sodium, Pesticide Manual, 10th Ed. 1994, pp.12–13, B33) Azoles of the formula III

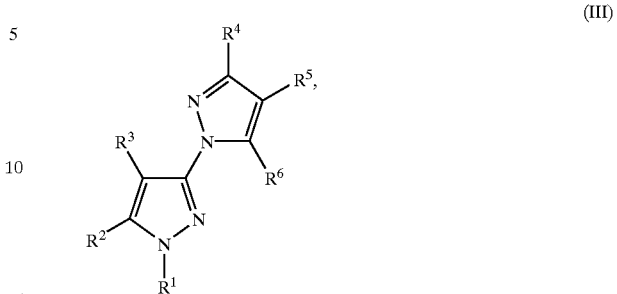

(III)

in which $R^1$ is $(C_1-C_4)$-alkyl ist, $R^2$ is $(C_1-C_4)$-alkyl, $(C_1-C_4)$-alkylthio or $(C_1-C_4)$-alkoxy, each radical of which may be substituted by one or more halogen atoms, or $R^1$ and $R^2$ together form the group $(CH_2)m$ where m=3 or 4, $R^3$ is hydrogen or halogen, $R^4$ is hydrogen or $(C_1-C_4)$-alkyl, $R^5$ is hydrogen, nitro, cyano or one of the groups —COOR$^7$, —C(=X) NR$^7$R$^8$ or —C(=X)R$^{10}$, $R^6$ is hydrogen, halogen, cyano, $(C_1-C_4)$-alkyl, $(C_1-C_4)$-alkylthio or —NR$^{11}$R$^{12}$, $R^7$ and $R^8$ are identical or different and are hydrogen or $(C_1-C_4)$-alkyl, or $R^7$ and $R^8$ together with the nitrogen to which they are attached form a saturated 5- or 6- membered carbocyclic ring, $R^{10}$ is hydrogen or $(C_1-C_4)$-alkyl, where the latter may be unsubstituted or substituted by one or more halogen atoms, and $R^{11}$ and $R^{12}$ are identical or different and are hydrogen, $(C_1-C_4)$-alkyl or $(C_1-C_4)$-alkoxycarbonyl, where $R^{11}$ and $R^{12}$ together with the nitrogen to which they are attached may form a 3-, 5- or 6-membered carbocyclic or aromatic ring in which one carbon atom may optionally be replaced by an oxygen atom, particular preference being given to B33a) a compound of the formula III in which $R^1$ and $R^2$ together form the group $(CH_2)m$ where m=4, $R^3$ is chlorine, $R^4$ is hydrogen, $R^5$ is cyano, $R^6$ is —NR$^{11}$R$^{12}$, $R^{11}$ is hydrogen and $R^{12}$ is isopropyl

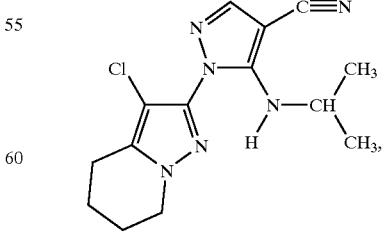

and

B33b) a compound of the formula III in which $R^1$ and $R^2$ together form the group $(CH_2)_m$ where m=4, $R^3$ is chlorine, $R^4$ is hydrogen, $R^5$ is cyano, $R^6$ is —$NR^{11}R^{12}$, $R^{11}$ is methyl and $R^{12}$ is —$CH_2$—C≡CH, where the azoles of the formula II are known, inter alia, from WO 94/08999, B34) chlorimuron 2-(4-chloro-6-methoxy,pyrimidin-2-ylcarbamoyl-sulfamoyl)benzoic acid used, inter alia, as chlorimuron-ethyl, i.e. as the ethyl ester of chlorimuron, Pesticide Manual, 11th Ed. 1997, pp.217–218, B35) triasulfuron 1-[2-(2-chloroethoxy)phenylsulfonyl]-3-(4-methoxy-6-methyl-1,3,5-triazin-2-yl)urea Pesticide Manual, 11th Ed. 1997, pp.1222–1223, B36) ioxynil 4-hydroxy-3,5-di-iodobenzonitrile used, inter alia, as ioxynil, ioxynil-octanoate, ioxynil-sodium Pesticide Manual, 11th Ed. 1997, pp.718–721, B37) picloram 4-amino-3,5,6-trichloropyridin-2-carboxylic acid used, inter alia, as picloram, picloram-potassium, mixture of picloram and picloram-potassium, Pesticide Manual, 11th Ed. 1997, pp.977–979, and B38) carfentrazon ethyl (RS)-2-chloro-3-[2-chloro-5-(4-difluoromethyl-4,5-dihydro-3-methyl-5-oxo-1H-1,2,4-,triazol-1-yl)-4-fluorophenyl]propionate used, inter alia, as carfentrazone-ethyl (as shown) or else as acid, Pesticide Manual, 11th Ed. 1997, pp.191–193.

From among the type B compounds showing selectivity in rice and being active against dicotyledonous plants and in some cases against cyperaceae {subgroup Bb) with the herbicidally active compounds B28)–B38) and their customary derivatives}, the combination partners B28) to B33), in each case on their own or else in combination with others, are extraordinarily suitable for use as component of a herbicidal composition according to the invention.

Thus, inter alia, the aryloxyalkylcarboxylic acids B28) to B31) are tolerated very well, and they also cover gaps in the weed spectrum to be controlled in an excellent manner.

Emphasis should furthermore be given to the compounds B34) and B35) which, as sulfonylurea compounds, are extraordinarily effective in the control of dicotyledonous plants/cyperaceae which are difficult to control by compounds of type A.

A third subgroup of compounds which, when admixed with compounds of type A, permit the production of herbicidal compositions having excellent properties is the subgroup Bc) of the herbicides which are selective in rice, mainly against cyperaceae. Type B substances having this activity profile are preferably found in the chemical substance classes of the ureas and benzofuranyl compounds, or they are present in the form of triclopyr or bentanzon.

Thus, a further advantageous embodiment of the invention comprises, as herbicide of type B, B39) bentazon

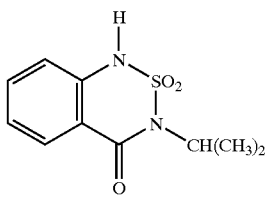

3-isopropyl-1H-2,1,3-benzothiadiazin-4(3H)-one-2,2-dioxide Pesticide Manual, 10th Ed. 1994, pp.90–91, B40) triclopyr

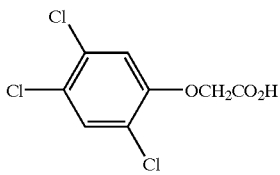

[(3,5,6-trichloro-2-pyridinyl)oxy]acetic acid, preferably as triclopyr, triclopyr-butotyl, triclopyr-triethylammonium, Pesticide Manual, 10th Ed. 1994, pp.1015–1017, B41) benfuresate

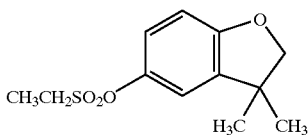

2,3-dihydro-3,3-dimethylbenzofuran-5-yl ethane-sulfonate Pesticide Manual, 10th Ed. 1994, pp.81–82
and/or
B42) daimuron

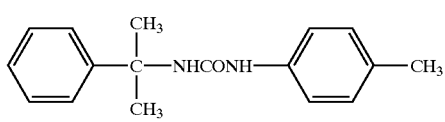

N-(4-methylphenyl)-N'-(1-methyl-1-phenylethyl) urea Pesticide Manual, 10th Ed. 1994, pp.275–276.

All the compounds B39) to B42) are herbicides which are selective in rice and which, with respect to the spectrum of the harmful plants to be controlled, meet the abovementioned profile of requirements. B41) in particular is a benzofuranyl compound having a pronounced activity against grasses and broad-leaved weeds in rice, whereas B42) is a urea having a particularly pronounced activity against cyperaceae and annual grasses in rice, but also against dicotyledonous plants Compositions with excellent activity are obtained when B39) and/or B42) are contained in the composition according to the invention as combination partners of type Bc), and it is then possible to control even particularly resistant harmful plants and even undesirable plants which are resistant against customary compositions in an excellent manner.

A fourth subgroup of compounds which, when admixed with compounds of type A, permit the production of herbicidal compositions having excellent properties is the subgroup Bd) of the herbicides which are selective in rice against grasses and dicotyledonous plants/cyperaceae. Type B substances having this activity profile are preferably found in the chemical substance classes of the 2,6-dinitroanilines, pyrazoles, pyrimidinyloxobenzoic acids, oxadiazoles, anilides, diphenyl ethers, alkylcarboxylic acids, of the sulfonylureas which are different from the sulfonylureas given in formula I, of the 1,3,5-triazines, pyridines and, surprisingly, even in the group of the organophosphorus compounds.

In another preferred embopdiment of the invention, the herbicidally active combinations comprise, as herbicides of type B, one or more herbicides which are selective in rice, mainly against grasses and dicotyledonous plants/cyperaceae, from the group consisting of B43)pendimethalin

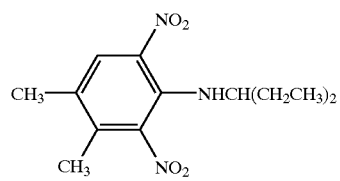

N-(1-ethylpropyl)-2,6-dinitro-3,4-xylidine Pesticide Manual, 10th Ed. 1994, pp.779–780

B44) clomazone

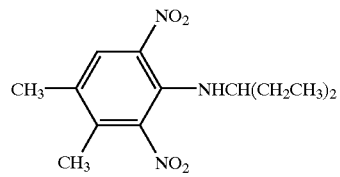

2-[(2-chlorophenyl)methyl]-4,4-dimethyl-3-isoxazolidinone; Pesticide Manual, 10th Ed. 1994, pp.220–221

B45) benzofenap

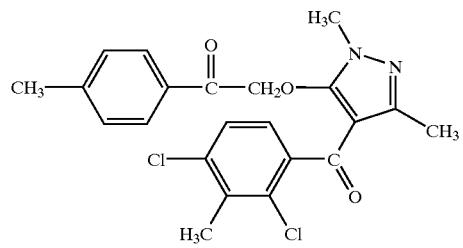

2-[[4-(2,4-dichloro-3-methylbenzoyl]-1,3-dimethyl-1H-pyrazol-5-yl]oxy]-1-(4-methylphenyl)acetophenone Pesticide Manual, 10th Ed. 1994, pp.92–93

B46) pyrazolynate,

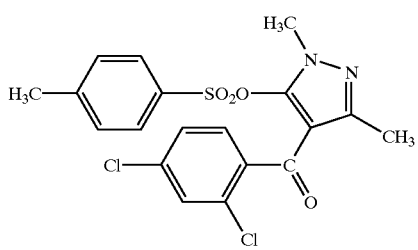

(2,4-dichlorophenyl) [1,3-dimethyl-5-[[(4-methyl-phenyl)sulfonyl]oxy]-1H-pyrazol-4-yl]methanone Pesticide Manual, 10th Ed. 1994, pp.870–871, B47) pyrazoxyfen,

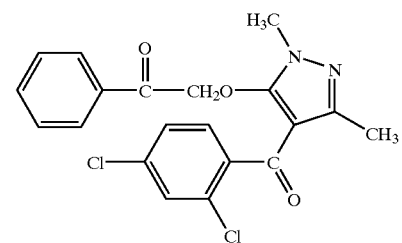

2-[[4-(2,4-dichlorobenzoyl)-1,3-dimethyl-1H-pyrazol-5-yl]oxy]-1-phenylethanone Pesticide Manual, 10th Ed. 1994, pp.874–875,

B48) KIH 2023

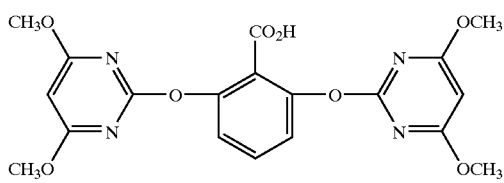

sodium 2,6-bis[(4,6-dimethoxypyrimidin-2-yl)oxy]-benzoate, preference is given to the sodium salt form Pesticide Manual, 10th Ed. 1994, p.620, B49) KIH 6127=pyriminobac-methyl

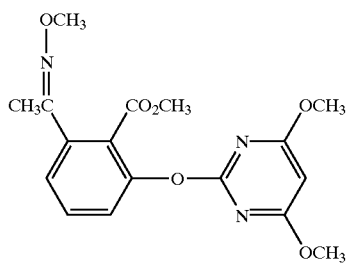

methyl 2-(4,6-dimethoxy-2-pyrimidinyloxy)-6-(1-methoxyiminoethyl)benzoate, also as acid or sodium salt Pesticide Manual, 11th Ed. 1997, pp.1071–1072, B50) oxadiazon

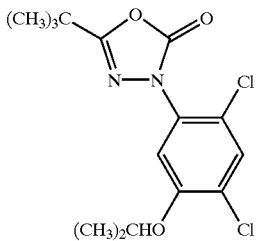

5-tert-butyl-3-(2,4-dichloro-5-isopropoxyphenyl)-1,3,4-oxadiazol-2(3H)-one, Pesticide Manual, 11th Ed. 1997, pp.905–907, B51) oxadiargyl

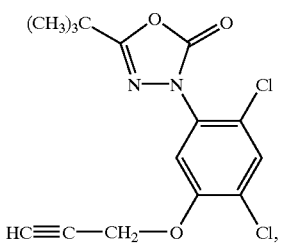

5-tert-butyl-3-[2,4-dichloro-5-(prop-2-ynyloxy)-phenyl]-1,3,4-oxadiazol-2(3H)-one, Pesticide Manual, 11th Ed. 1997, pp.904–905, B52) acetochlor

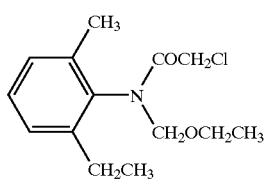

2-chloro-N-ethoxymethyl-6'-ethylaceto-o-toluidide, Pesticide Manual, 11th Ed. 1997, pp.10–12, B53) metolachlor

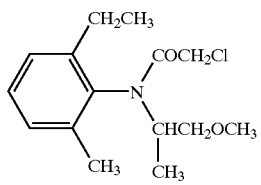

2-chloro-6'-ethyl-N-(2-methoxy-1-methylethyl)aceto-o-toluidide, Pesticide Manual, 11th Ed. 1997, pp.833–834, B54) metosulam

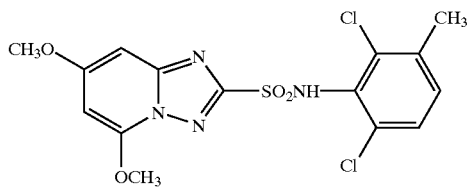

2',6'-dichloro-5,7-dimethoxy-3'-methyl[1,2,4]tria-zolo[1,5-a]pyrimidine-2-sulfoanilide Pesticide Manual, 11th Ed. 1997, pp.836–838, B55) oxyfluorfen

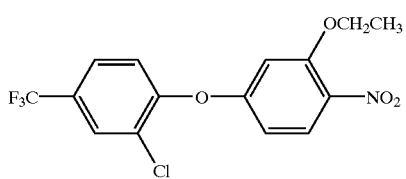

2-chloro-α,α,α-trifluoro-p-tolyl 3-ethoxy-4-nitro-phenyl ether, Pesticide Manual, 11th Ed. 1997, pp.919–921, and B56) dalapon

2,2-dichloropropionic acid, preferably also in its use form as sodium salt, i.e. as dalapon-sodium Pesticide Manual, 11th Ed. 1997, pp.331–333.

Of particular importance in the group Bd) are, inter alia, the 2,6-dinitroanilines, such as pendimethalin (B43)) and clomazone (B44)).

However, the pyrazoles (B45)-B47)) and the pyrimidinyloxobenzoic acids, for example B48) or B49) are also noteworthy here.

The pyrazoles B45) to B47) permit combinations with an excellent activity spectrum. B45) emphasizes the control of perennial broad-leaved weeds in rice, combinations with B46) have proved to be particularly useful against grasses and seeds in rice such as *Potamogeton distinctus, Sagittaria trifolium, Alisma canaliculatum* etc., and combinations which, in addition to at least one type A compound, comprise the compound B47) permit a virtually complete suppression of annual and perennial weeds in rice, both of the cyperaceae and of the dicotyledonous plants or grasses.

Combinations with B48) are also particularly advantageous for controlling *Echinochloa* spp. in "direct-seeded" rice, whereas the activity of combinations which comprise B49) as a component is noticeable, inter alia in a particularly favorable manner against *Echinochloa* spp. in paddy rice.

Of special interest are also combinations of the group Bd) with oxadiazoles, anilides, diphenyl ethers or alkylcarboxylic acids.

In the context of the invention, the combinations with oxadiazoles, such as, for example, B50) or B51) have proved to be very useful in particular against annual broad-leaved weeds and weed grasses by the pre-emergence method and of the same weeds by the post-emergence method. In particular, combinations with oxadiargyl (B51)) control in an excellent manner *Amaranthus, Bidens, Chenopodium, Malva, Monochoria, Polygonum, Portulaca, Potamogeton, Raphanus, Solanum, Sonchus* and *Rotala* among the broad-leaved weeds and *Echinochloa, Leptochloa, Brachiaria, Cenchrus, Digitaria, Eleusine, Panicum* and wild rice among the weed grasses, and also of annual seeds, both by the pre-emergence and, in some cases, by the post-emergence method.

Anilides, such as the chloroacetanilide B52) or B53), and the sulfoanilides, for example B54), also have to be emphasized as being useful combination partners for the type A compounds. Here, the anilides exhibit complementary activity among the annual grasses and broad-leaved weeds, in particular against *Gallium aparine, Stellaria media*, all kinds of *Brassicaceae* and also *Chenopodium* spp., *Amaranthus retroflexus, Solanum nigrum* and *Polygonum persicaria*, in each case in particular also by the post-emergence method.

Finally, diphenyl ethers or arylcarboxylic acids are also interesting partners for the type A sulfonylureas. The diphenyl ether B55) helps in closing activity gaps which may be present among the grasses and broad-leaved weeds. B56) has an enhancing effect in particular in the control of halophytic and semiaquatic weed grasses.

In the context of the invention, particularly advantageous mixtures result when, as type B compounds, the combination according to the invention comprises the combination partners from the group Bd) which feature in the experiments.

In a further preferred embodiment of the invention, the herbicidally active combinations comprise, as herbicides of type B, one or more herbicides which are selective in rice against grasses and dicotyledonous plants and cyperaceae from the group consisting of B57) metsulfuron

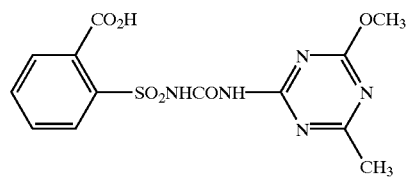

2-(4-methoxy-6-methyl-1,3,5-triazin-2-ylcarbamoyl-sulfamoyl)benzoic acid, usually employed as metsulfuron-methyl, Pesticide Manual, 10th Ed. 1994, pp.701–702, B58) bensulfuron

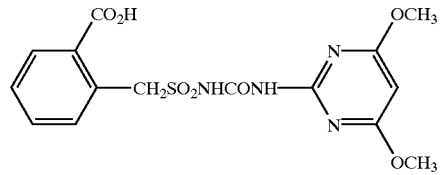

2-[[[[(4,6-dimethoxy-2-pyrimidinyl)amino]carbonyl]-amino]sulfonyl]methyl]benzoic acid, including, in particular, the use as bensulfuron-methyl, i.e. as the methyl ester of bensulfuron, where the compounds B58) are known, inter alia, from Pesticide Manual, 10th Ed. 1994, pp.85–87, B59) pyrazosulfuron

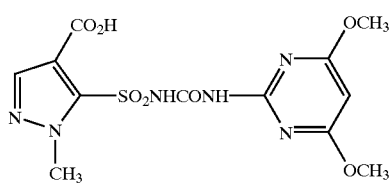

5-[[[[(4,6-dimethoxy-2-pyrimidinyl)amino]carbonyl]-amino]sulfonyl]-1-methyl-1H-pyrazol-4-carboxylic acid including, inter alia, as most important use form the ethyl ester, pyrazosulfuron-ethyl, where the compounds B59) are known, inter alia, from Pesticide Manual, 10th Ed. 1994, pp.873–874;

B60) cinosulfuron

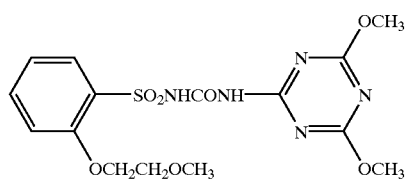

N-[[(4,6-dimethoxy-1,3,5-triazin-2-yl)amino]carbonyl]-2-(2-methoxyethoxy)benzolsulfonamide, where the compound B60) is known, inter alia, from Pesticide Manual, 10th Ed. 1994, pp.211–212, B61) imazosulfuron

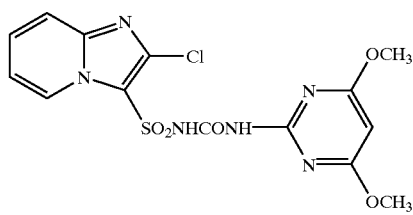

2-chloro-N-[[(4,6-dimethoxy-2-pyrimidinyl)amino]-carbonyl]imidazo[1,2-a]pyridine-3-sulfonamide, where the compound B61) is known, inter alia, from Pesticide Manual, 10th Ed. 1994, pp.589–599, B62) AC 322,140 or cyclosulfamuron

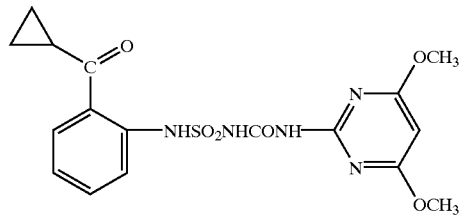

N-[[[2-(cyclopropylcarbonyl)phenyl]amino]sulfonyl]-$N^1$-(4,6-dimethoxypyrimidin-2-yl)urea, where the compound B62) is known, inter alia, from Pesticide Manual, 10th Ed. 1994, pp.8–9, B63) Phenoxysulfonylureas of the formula IV

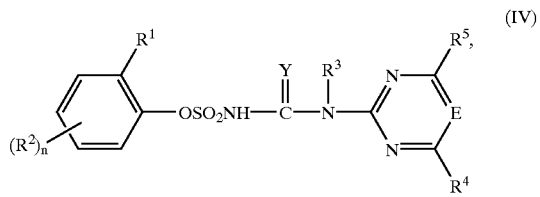

in which a) $R^1$ is ethoxy, propoxy or isopropoxy and $R^2$ is halogen, $NO_2$, $CF_3$, CN, $(C_1-C_4)$-alkyl, $(C_1-C_4)$-alkoxy, $(C_1-C_4)$-alkylthio or $((C_1-C_4)$-alkoxy)carbonyl and n is 0, 1, 2 or 3 or b) $R^1$ is saturated or unsaturated $(C_1-C_8)$-alkoxy, which is substituted by halogen, saturated or unsaturated $(C_1-C_6)$-alkoxy, a radical of the formula $((C_1-C_6)$-alkyl)-S—, $((C_1-C_6)$-alkyl)-SO—, $((C_1-C_6)$-alkyl)-$SO_2$—, $((C_1-C_6)$-alkyl)-O—CO—, $NO_2$, CN or phenyl; furthermore $(C_2-C_8)$-alkenyloxy or -alkynyloxy and $R^2$ is saturated or unsaturated $(C_1-C_8)$-alkyl, phenyl, phenoxy, $(C_1-C_4)$-alkoxy, $(C_1-C_4)$-alkylthio, $((C_1-C_4)$-alkoxy)carbonyl, where all of the abovementioned radicals $R^2$ may be substituted by halogen, $(C_1-C_4)$-alkoxy or $(C_1-C_4)$-alkylthio, or halogen, $NO_2$, $(C_1-C_4)$-alkylsulfonyl or -sulfinyl and n is 0, 1, 2 or 3 or c) $R^1$ is $(C_1-C_8)$-alkoxy and $R^2$ is $(C_2-C_8)$-alkenyl or -alkynyl, phenyl, phenoxy, where the radicals mentioned above for $R^2$ are unsubstituted or substituted by halogen, $(C_1-C_4)$-alkoxy or $(C_1-C_4)$-alkylthio, or $(C_1-C_4)$-alkylsulfonyl or -sulfinyl and n is 1, 2 or 3 or d) $R^1$ is, in each case in the 2-position on the phenyl radical, halogen, methoxy, ethyl or propyl, $R^2$ is $((C_1-C_4)$-alkoxy)carbonyl in the 6-position on the phenyl radical and n=1 and in all cases a) to d)

$R^3$ is hydrogen, saturated or unsaturated $(C_1-C_8)$-alkyl or $(C_1-C_4)$-alkoxy, $R^4,R^5$ independently of one another are hydrogen, halogen, $(C_1-C_4)$-alkyl, $(C_1-C_4)$-alkoxy, $(C_1-C_4)$-alkylthio, where the three last-mentioned radicals are unsubstituted or substituted by halogen, $(C_1-C_4)$-alkoxy or $(C_1-C_4)$-alkylthio, Y is O or S and E is CH or N, where the sulfonylureas of the formula IV are known, inter alia, from DE-A-38 16 704.2 (EP-A-0 342 569), DE-A-38 16 703.4 (EP-A-0 342 568) und DE-A-39 09 053.1 (EP-A-0 388 771), particularly preferably from among the compounds of the formula TV B63a) ethoxysulfuron (HOE 095404)

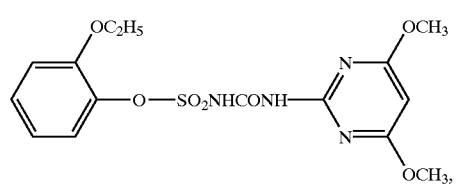

B64) azimsulfuron (DPX-A8947),

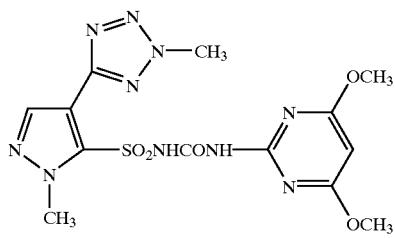

introduced at the Brighton Crop Protection Conference Weeds 1995,
and
B65) nicosulfuron

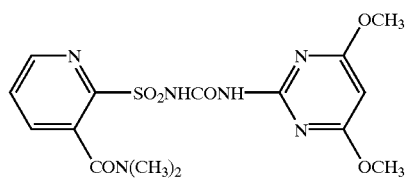

1-(4,6-dimethoxypyrimidin-2-yl)-3-(3-dimethylcarbamoyl-2-pyridylsulfonyl)urea Pesticide Manual, 10th Ed. 1994, pp.734–735.

The compounds B57) to B65) are certain sulfonylureas whose selection and suitability is critical for the combinations according to the invention. They are structurally different from the sulfonylureas of the formula I. All of them give, together with partners of type A, excellent combinations having high selectivity in rice and activity against grasses, cyperaceae and dicotyledonous harmful plants. Frequently, it is possible, by selecting a suitable type B compound, to influence the spectrum of harmful plants that is mainly controlled by the combinations according to the invention in a targeted manner.

Thus, sulfonylureas B57) or B58) give combinations having high selectivity against annual and perennial weeds in rice, such as: *Butomus umbellatus, Scirpus maritimus, Scirpus mucronatus, Alisma plantago-aquatica, Alisma lanceolatum, Sparganium erectum, Cyperus* spp., *Typha* spp.

The activity spectrum of combinations with sulfonylurea B59) includes mainly the selective control of annual and perennial broad-leaved weeds, seeds and grasses (barnyard grass) in rice, whereas B60) has its main activity against *Alisma*, annual *Cyperus, Elocharia, Marsilea, Potamogeton* and *Sagittaria* spp., *Monochoria vaginalis* and *Sphenoclea zeylanica*.

Combinations according to the invention with sulfonylurea B61) have proved to have high selectivity against annual and perennial broad-leaved weeds and seeds in rice, whereas B62) is selective against *Cyperus serotinus, Eleocharis kuroguwai, Sagittaria pygmaea* and similar weeds in rice.

Combinations according to the invention with phenoxysulfonylureas B63) can serve to close activity gaps in the range of mono- and dicotyledonous weeds in rice, similarly to mixtures with B64) and/or B65).

Of particular interest are, especially, also herbicidal compositions with sulfonylureas which are selective in rice against dicotyledonous plants, cyperaceae and grasses for which biological data are given in the Example Section.

Of relatively great importance are furthermore, from the group Bd), the 1,3,5-triazines, pyridines, organo-phosphorus compounds, and other individual representatives of certain chemical substance classes, for use in combinations according to the invention.

In another preferred embodiment of the invention, the herbicidally active combinations comprise, as herbicides of type B, one or more herbicides which are selective in rice against grasses and dicotyledonous plants and cyperaceae, from the group consisting of B66) prometryn

$N^2$, $N^4$-diisopropyl-6-methylthio-1,3,5-triazine-2,4-diamine, Pesticide Manual, 11th Ed. 1997, pp.1011–1013, B67) simetryn

$N^2$, $N^4$-diethyl-6-methylthio-1,3,5-triazine-2,4-diamine, where the compound B67) is known, inter alia, from Pesticide Manual, 11th Ed. 1997, pp.1108–1109, B68) thiazopyr

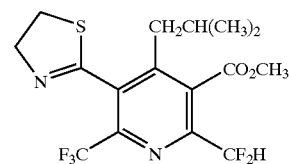

methyl 2-difluoromethyl-5-(4,5-dihydro-1,3-thiazolyl)-6-trifluoromethylnicotinate, where the compound B68) is known, inter alia, from Pesticide Manual, 11th Ed. 1997, pp.1185–1187;

B69) pyrazophos

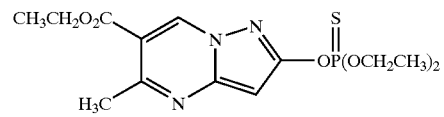

ethyl 2-diethoxyphosphinothioyloxy-5-methylpyrazolo-[1,5-a]pyrimidine-6-carboxylate, where the compound B69) is known, inter alia, from Pesticide Manual, 11th Ed. 1997, pp.1050–1052, B70) pentoxazone

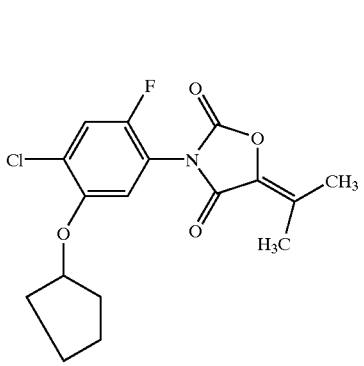

3-(4-chloro-5-cyclopentyloxy-2-fluorophenyl)-5-isopropylidene-1,3-oxazolidine-2,4-dione, where the compound B70) is known, inter alia, from Pesticide Manual, 11th Ed. 1997, pp.942–943, B71) indanofan

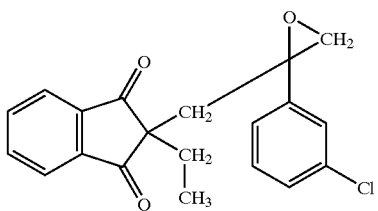

(RS)-2-[2-(3-chlorophenyl)-2,3-epoxypropyl]-2-ethyl-indane-1,3-dione, where the compound B71) is known, inter alia, from Pesticide Manual, 11th Ed. 1997, p.715, B72) LGC-40863=pyribenzoxim

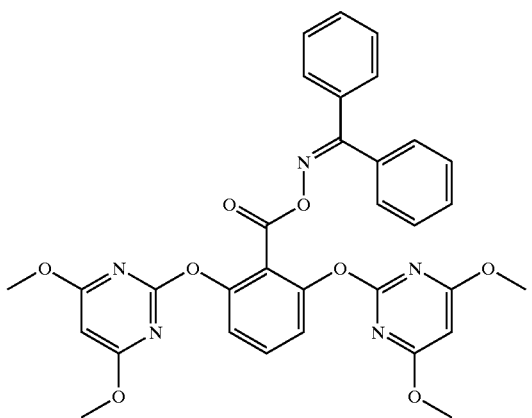

introduced at the Brighton Crop Protection Conference Weeds 1997, and

B73) MY100=oxaziclomefone

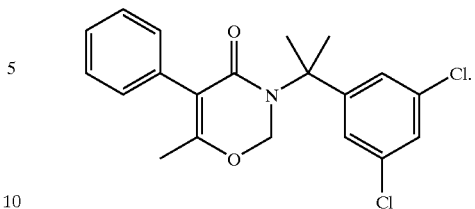

The compounds B1) to B73) are selective herbicides in rice and transgenic rice which are known, for example, from the source given at the respective compound and which are used in combination specifically with the A compounds of the invention. In addition to the parent substance, the formula of which is in each case given for clarity, modifications of the parent substances which are customarily employed are in some cases also referred to.

In particular, all modifications of the B compounds which are customarily employed are part of the present invention, even if they are not expressly mentioned individually. If optically active forms of the type B compounds are customary, these also form part of the invention, and in some cases these forms were also referred to (for example fenoxaprop-ethyl and fenoxaprop-P-ethyl etc.).

Combinations of the active compounds A+B have superadditive effects, i.e. using the herbicidal compositions according to the invention as it is possible, with the same control of the harmful plants, to reduce the application rate and/or to increase the safety margin in rice crops. Both make sense, from an economical as well as ecological point of view. The amounts of components A+B to be employed, the ratio of the components A:B and the order in which the components are applied depend, like, for example, the formulation that is to be chosen, on a whole range of factors.

In this context, the type of mixing partner, the development stage of the broad-leaved weeds or weed grasses, the weed spectrum to be controlled, environmental factors, climatic conditions, soil conditions, etc., have to be taken into consideration.

In a very particularly preferred embodiment according to the invention, the herbicidal compositions according to the invention comprise a synergistically effective amount of a combination of the compounds of the formula I or their salts (type A compounds) with compounds from group B. Here, it has to be particularly emphasized that even in combinations with application rates or ratios by weight of A:B in which a synergism cannot in all cases be detected without any problems—for example because the individual compounds are usually employed in the combination at very different application rates or because the control of the harmful plants by the individual compounds is already very good—the herbicidal compositions of the invention usually have an inherent synergistic action.

The application rates of the herbicide A are generally between 0.1 and 100 g of ai/ha (ai=active ingredients, i.e. application rate based on the active compound), preferably between 0.5 and 60 g of ai/ha, very particularly preferably between 2 and 40 g of ai/ha.

With respect to the specific subgroups Aa) and Ab), the application rates of compounds of type A are usually:

| Type A compounds | Application rates g of ai/ha | |
|---|---|---|
|  | standard | preferred |
| Aa) Sulfonylureas of the formula I in rice {e.g. A1) or A1*)} | 0.1 to 10 | 0.5 to 5 |
| Ab) Sulfonylureas of the formula I in rice {e.g. A2) or A3)} | 2 to 40 | 5 to 25 |

Particularly surprising is the extremely low application rate of the sulfonylureas of the formula I from subgroup Aa). The application rate, for example of the compound A1) or A1*), is reduced again drastically, compared with the application rate known for the use of A1) or A1*) for controlling harmful plants in cereals or maize. This particularly low application rate, with an unchanged or better control of harmful plants in the control of harmful plants in rice, was, based on the prior art, unforeseeable.

The application rates of compounds of type B are usually:

| Type B compounds | Application rates g of ai/ha | |
|---|---|---|
|  | standard | preferred |
| Ba) Grass herbicides in rice {e.g. B1)–B27)} | 10 to 4000 | 50 to 1000 |
| Bb) Herbicides against dicotyledonous plants/cyperaceae in rice {e.g. B28)–B30)} | 100 to 3000 | 200 to 2000 |
| Bb) Herbicides against dicotyledonous plants/cyperaceae in rice {e.g. B31)} | 50 to 1000 | 100 to 500 |
| Bb) Herbicides against dicotyledonous plants/cyperaceae in rice {e.g. B32)} | 5 to 1000 | 10 to 500 |
| Bb) Herbicides against dicotyledonous plants/cyperaceae in rice {e.g. B33a), B33b)} | 10 to 400 | 20 to 200 |
| Bb) Herbicides against dicotyledonous plants/cyperaceae in rice {e.g. B34)–B35)} | 1 to 50 | 4 to 20 |
| Bb) Herbicides against dicotyledonous plants/cyperaceae in rice {e.g. B36)} | 1 to 2000 | 5 to 1000 |
| Bb) Herbicides against dicotyledonous plants/cyperaceae in rice {e.g. B37)} | 1 to 2000 | 5 to 1000 |
| Bb) Herbicides against dicotyledonous plants/cyperaceae in rice {e.g. B38)} | 1 to 2000 | 5 to 1000 |
| Bc) Herbicides against cyperaceae in rice {e.g. B39) to B42)} | 50 to 2500 | 100 to 1000 |
| Bd) Herbicides against grasses and dicotyledonous plants/cyperaceae in rice {e.g. B43) to B49)} | 50 to 5000 | 100 to 2500 |
| Bd) Herbicides against grasses and dicotyledonous plants/cyperaceae in rice {e.g. B50 to B51)} | 15 to 2000 | 30 to 1000 |
| Bd) Herbicides against grasses and dicotyledonous plants/cyperaceae in rice {e.g. B52) to B56)} | 15 to 2000 | 30 to 1000 |
| Bd) Herbicides against grasses and dicotyledonous plants/cyperaceae in rice {e.g. B57) to B65)} | 2 to 80 | 4 to 40 |
| Bd) Herbicides against grasses and dicotyledonous plants/cyperaceae in rice {e.g. B66) to B67)} | 15 to 2000 | 30 to 1000 |
| Bd) Herbicides against grasses and dicotyledonous plants/cyperaceae in rice {e.g. B68)} | 15 to 2000 | 30 to 1000 |
| Bd) Herbicides against grasses and dicotyledonous plants/cyperaceae in rice {e.g. B69)} | 15 to 2000 | 30 to 1000 |
| Bd) Herbicides against grasses and dicotyledonous plants/cyperaceae in rice {e.g. B70)} | 15 to 2000 | 30 to 1000 |
| Bd) Herbicides against grasses and dicotyledonous plants/cyperaceae in rice {e.g. B71)} | 15 to 2000 | 30 to 1000 |
| Bd) Herbicides against grasses and dicotyledonous | | |

-continued

In the invention, the application rate of compounds of type A + compounds of type B are usually:

| Type B compounds | Application rates g of ai/ha | | |
|---|---|---|---|
| | A | + | B |
| Ba) Grass herbicides in rice {e.g. B1)–B27)} | A) 0.5 to 60<br>Aa) 0.5 to 5<br>Ab) 5 to 25 | | 10 to 4000 |
| Bb) Herbicides against dicotyledonous plants/cyperaceae in rice {e.g. B28)–B30)} | A) 0.5 to 60<br>Aa) 0.5 to 5<br>Ab) 5 to 25 | | 100 to 3000 |
| Bb) Herbicides against dicotyledonous plants/cyperaceae in rice {e.g. B31)} | A) 0.5 to 60<br>Aa) 0.5 to 5<br>Ab) 5 to 25 | | 50 to 1000 |
| Bb) Herbicides against dicotyledonous plants/cyperaceae in rice {e.g. B32)} | A) 0.5 to 60<br>Aa) 0.5 to 5<br>Ab) 5 to 25 | | 5 to 1000 |
| Bb) Herbicides against dicotyledonous plants/cyperaceae in rice {e.g. B33a), B33b)} | A) 0.5 to 60<br>Aa) 0.5 to 5<br>Ab) 5 to 25 | | 10 to 400 |
| Bb) Herbicides against dicotyledonous plants/cyperaceae in rice {e.g. B34)–B35)} | A) 0.5 to 60<br>Aa) 0.5 to 5<br>Ab) 5 to 25 | | 1 to 2000 |
| Bb) Herbicides against dicotyledonous plants/cyperaceae in rice {e.g. B36)} | A) 0.5 to 60<br>Aa) 0.5 to 5<br>Ab) 5 to 25 | | 1 to 2000 |
| Bb) Herbicides against dicotyledonous plants/cyperaceae in rice {e.g. B37)} | A) 0.5 to 60<br>Aa) 0.5 to 5<br>Ab) 5 to 25 | | 1 to 2000 |
| Bb) Herbicides against dicotyledonous plants/cyperaceae in rice {e.g. B38)} | A) 0.5 to 60<br>Aa) 0.5 to 5<br>Ab) 5 to 25 | | 1 to 2000 |
| Bc) Herbicides against cyperaceae in rice {e.g. B39) to B42)} | A) 0.5 to 60<br>Aa) 0.5 to 5<br>Ab) 5 to 25 | | 50 to 2500 |
| Bd) Herbicides against grasses and dicotyledonous plants/cyperaceae in rice {e.g. B43) to B49)} | A) 0.5 to 60<br>Aa) 0.5 to 5<br>Ab) 5 to 25 | | 50 to 5000 |
| Bd) Herbicides against grasses and dicotyledonous plants/cyperaceae in rice {e.g. B50) to B51)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B52) to B54)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B55)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B56)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B57) to B65)} | A) 0.5 to 60<br>Aa) 0.5 to 5<br>Ab) 5 to 25 | | 2 to 80 |
| Bd) Herbicides against grasses and dicotyledonous plants/cyperaceae in rice {e.g. B66) to B67)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B68)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B69)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B70)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B71)} | A) 0.5 to 60<br>Aa) 0.5 to 5<br>Ab) 5 to 25 | | 15 to 2000 |
| Bd) Herbicides against grasses and dicotyledonous plants/cyperaceae in rice {e.g. B72)} | | | 15 to 2000 |
| Bd) Herbicides against grasses and dicotyledonous plants/cyperaceae in rice {e.g. B73)} | 15 to 2000 | | 30 to 1000 |

-continued

| | Mixing ratios A:B | |
|---|---|---|
| Type B compounds | standard | preferred |
| {e.g. B72)}<br>Bd) Herbicides against grasses and dicotyledonous plants/cyperaceae in rice<br>{e.g. B73)} | A) 0.5 to 60<br>Aa) 0.5 to 5<br>Ab) 5 to 25 | 15 to 2000 |

The ratios by weight of A:B of the combined herbicides can, as already mentioned, vary within wide limits, like their application rates. A range of the ratios of the application rates (wt/wt) according to the invention includes, for example, A:B from 1:20,000 to about 200:1. In the context of the invention, preference is given to compositions which comprise compounds of the formula I or their salts (type A compounds) and compounds from group B in a weight ratio of about 1:8000 to 100:1. Very particularly advantageous are compositions having ratios of application rates of A:B which are between 1:4000 and 50:1. In particular, for the various subgroups, the following picture results, i.e. the following ratios by weight are preferably used:

| | Mixing ratios A:B | |
|---|---|---|
| Type B compounds | standard | preferred |
| Ba) Grass herbicides in rice {e.g. B1)–B27)} | 1:8000 to 20:1 | 1:4000 to 10:1 |
| Bb) Herbicides against dicotyledonous plants/cyperaceae in rice {e.g. B28)–B30)} | 1:6000 to 200:1 | 1:3000 to 100:1 |
| Bb) Herbicides against dicotyledonous plants/cyperaceae in rice {e.g. B31)} | 1:4000 to 100:1 | 1:1000 to 50:1 |
| Bb) Herbicides against dicotyledonous plants/cyperaceae in rice {e.g. B32)} | 1:4000 to 10:1 | 1:1000 to 5:1 |
| Bb) Herbicides against dicotyledonous plants/cyperaceae in rice {e.g. B33a), B33b)} | 1:2000 to 20:1 | 1:400 to 10:1 |
| Bb) Herbicides against dicotyledonous plants/cyperaceae in rice {e.g. B34)–B35)} | 1: to :1 | 1: to :1 |
| Bb) Herbicides against dicotyledonous plants/cyperaceae in rice {e.g. B36)} | 1: to :1 | 1: to :1 |
| Bb) Herbicides against dicotyledonous plants/cyperaceae in rice {e.g. B37)} | 1: to :1 | 1: to :1 |
| Bb) Herbicides against dicotyledonous plants/cyperaceae in rice {e.g. B38)} | | |
| Bc) Herbicides against cyperaceae in rice {e.g. B39) to B42)} | 1:10,000 to 100:1 | 1:2500 to 50:1 |
| Bd) Herbicides against grasses and dicotyledonous plants/cyperaceae in rice {e.g. B43) to B49)} | 1:20,000 to 100:1 | 1:5000 to 50:1 |
| Bd) Herbicides against grasses and dicotyledonous plants/cyperaceae in rice {e.g. B50) to B51)} | 1: to :1 | 1: to :1 |
| Bd) Herbicides against grasses and dicotyledonous plants/cyperaceae in rice {e.g. B52 to B54)} | 1: to :1 | 1: to :1 |
| Bd) Herbicides against grasses and dicotyledonous plants/cyperaceae in rice {e.g. B55)} | 1: to :1 | 1: to :1 |
| Bd) Herbicides against grasses and dicotyledonous plants/cyperaceae in rice {e.g. B56)} | 1:320 to 4:1 | 1:80 to 2:1 |
| Bd) Herbicides against grasses and dicotyledonous plants/cyperaceae in rice {e.g. B57 to B65)} | 1: to :1 | 1: to :1 |
| Bd) Herbicides against grasses and dicotyledonous plants/cyperaceae in rice {e.g. B66) to B67)} | 1: to :1 | 1: to :1 |
| Bd) Herbicides against grasses and dicotyledonous plants/cyperaceae in rice {e.g. B68)} | 1: to :1 | 1: to :1 |
| Bd) Herbicides against grasses and dicotyledonous plants/cyperaceae in rice {e.g. B69)} | | |

-continued

| Type B compounds | Mixing ratios A:B | |
|---|---|---|
| | standard | preferred |
| Bd) Herbicides against grasses and dicotyledonous plants/cyperaceae in rice {e.g. B70)} | 1: to :1 | 1: to :1 |
| Bd) Herbicides against grasses and dicotyledonous plants/cyperaceae in rice {e.g. B71) to B73)} | 1: to :1 | 1: to :1 |

With respect to the different subgroups Aa) to Ac), the following specific preferred ratios of application rates (ratios by weight) result:

Compounds of subgroup Aa), preferably compound A1) or A1*):

| Type B compounds | Mixing ratios Aa):B | |
|---|---|---|
| | standard | preferred |
| Ba) Grass herbicides in rice {e.g. B1)–B27)} | 1:20,000 to 2:1 | 1:8000 to 1:2 |
| Bb) Herbicides against dicotyledonous plants/cyperaceae in rice {e.g. B28)–B30)} | 1:10,000 to 20:1 | 1:5000 to 10:1 |
| Bb) Herbicides against dicotyledonous plants/cyperaceae in rice {e.g. B31)} | 1:4000 to 10:1 | 1:2000 to 5:1 |
| Bb) Herbicides against dicotyledonous plants/cyperaceae in rice {e.g. B32)} | 1:4000 to 1:1 | 1:2000 to 1:2 |
| Bb) Herbicides against dicotyledonous plants/cyperaceae in rice {e.g. B33a), B33b)} | 1:2000 to 2:1 | 1:800 to 1:1 |
| Bb) Herbicides against dicotyledonous plants/cyperaceae in rice {e.g. B34), B35)} | 1:5000 to 40:1 | 1:5000 to 20:1 |
| Bb) Herbicides against dicotyledonous plants/cyperaceae in rice {e.g. B36)} | 1:5000 to 40:1 | 1:5000 to 20:1 |
| Bb) Herbicides against dicotyledonous plants/cyperaceae in rice {e.g. B37)} | 1:5000 to 40:1 | 1:5000 to 20:1 |
| Bb) Herbicides against dicotyledonous plants/cyperaceae in rice {e.g. B38)} | 1:10,000 to 10:1 | 1:5000 to 5:1 |
| Bc) Herbicides against cyperaceae in rice {e.g. B39) to B42)} | 1:20,000 to 10:1 | 1:10,000 to 5:1 |
| Bd) Herbicides against grasses and dicotyledonous plants/cyperaceae in rice {e.g. B43) to B49)} | 1:5000 to 40:1 | 1:5000 to 20:1 |
| Bd) Herbicides against grasses and dicotyledonous plants/cyperaceae in rice {e.g. B50) to B51)} | 1:5000 to 40:1 | 1:5000 to 20:1 |
| Bd) Herbicides against grasses and dicotyledonous plants/cyperaceae in rice {e.g. B52) to B54)} | 1:5000 to 40:1 | 1:5000 to 20:1 |
| Bd) Herbicides against grasses and dicotyledonous plants/cyperaceae in rice {e.g. B55)} | 1:5000 to 40:1 | 1:5000 to 20:1 |
| Bd) Herbicides against grasses and dicotyledonous plants/cyperaceae in rice {e.g. B56)} | 1:320 to 1:2 | 1:160 to 1:5 |
| Bd) Herbicides against grasses and dicotyledonous plants/cyperaceae in rice {e.g. B57 to B65)} | 1:5000 to 40:1 | 1:5000 to 20:1 |
| Bd) Herbicides against grasses and dicotyledonous plants/cyperaceae in rice {e.g. B66) to B67)} | 1:5000 to 40:1 | 1:5000 to 20:1 |
| Bd) Herbicides against grasses and dicotyledonous plants/cyperaceae in rice {e.g. B68)} | 1:5000 to 40:1 | 1:5000 to 20:1 |
| Bd) Herbicides against grasses and dicotyledonous plants/cyperaceae in rice {e.g. B69)} | | |

-continued

| Type B compounds | Mixing ratios Aa):B | |
|---|---|---|
| | standard | preferred |
| Bd) Herbicides against grasses and dicotyledonous plants/cyperaceae in rice {e.g. B70)} | 1:5000 to 40:1 | 1:5000 to 20:1 |
| Bd) Herbicides against grasses and dicotyledonous plants/cyperaceae in rice {e.g. B71 to B73)} | 1:5000 to 40:1 | 1:5000 to 20:1 |

Compounds of the subgroup Ab), preferably compounds A2) or A3):

| Type B compounds | Mixing ratios Ab):B | |
|---|---|---|
| | standard | preferred |
| Ba) Grass herbicides in rice {e.g. B1)–B27)} | 1:2000 to 10:1 | 1:4000 to 5:1 |
| Bb) Herbicides against dicotyledonous plants/cyperaceae in rice {e.g. B28)–B30)} | 1:1500 to 10:1 | 1:750 to 5:1 |
| Bb) Herbicides against dicotyledonous plants/cyperaceae in rice {e.g. B31)} | 1:500 to 50:1 | 1:250 to 25:1 |
| Bb) Herbicides against dicotyledonous plants/cyperaceae in rice {e.g. B32)} | 1:500 to 2.5:1 | 1:250 to 1:1 |
| Bb) Herbicides against dicotyledonous plants/cyperaceae in rice {e.g. B33a), B33b)} | 1:200 to 10:1 | 1:100 to 5:1 |
| Bb) Herbicides against dicotyledonous plants/cyperaceae in rice {e.g. B34)–B35)} | 1: to :1 | 1: to :1 |
| Bb) Herbicides against dicotyledonous plants/cyperaceae in rice {e.g. B36)} | 1: to :1 | 1: to :1 |
| Bb) Herbicides against dicotyledonous plants/cyperaceae in rice {e.g. B37)} | 1: to :1 | 1: to :1 |
| Bb) Herbicides against dicotyledonous | | |

-continued

| Type B compounds | Mixing ratios Ab):B | |
|---|---|---|
| | standard | preferred |
| plants/cyperaceae in rice {e.g. B38)} | | |
| Bc) Herbicides against cyperaceae in rice {e.g. B39) to B42)} | 1:1250 to 50:1 | 1:725 to 25:1 |
| Bd) Herbicides against grasses and dicotyledonous plants/cyperaceae in rice {e.g. B43) to B49)} | 1:2500 to 50:1 | 1:1250 to 25:1 |
| Bd) Herbicides against grasses and dicotyledonous plants/cyperaceae in rice {e.g. B50 to B51)} | 1: to :1 | 1: to 1: |
| Bd) Herbicides against grasses and dicotyledonous plants/cyperaceae in rice {e.g. B52 to B54)} | 1: to 1: | 1: to 1: |
| Bd) Herbicides against grasses and dicotyledonous plants/cyperaceae in rice {e.g. B55)} | 1: to 1: | 1: to 1: |
| Bd) Herbicides against grasses and dicotyledonous plants/cyperaceae in rice {e.g. B56)} | 1: to 1: | 1: to 1: |
| Bd) Herbicides against grasses and dicotyledonous plants/cyperaceae in rice {e.g. B57 to B65)} | 1:40 to 1:1 | 1:20 to 1:2 |
| Bd) Herbicides against grasses and dicotyledonous plants/cyperaceae in rice {e.g. B66 to B67)} | 1: to :1 | 1: to :2 |
| Bd) Herbicides against grasses and dicotyledonous plants/cyperaceae in rice {e.g. B68)} | 1: to :1 | 1: to :2 |
| Bd) Herbicides against grasses and dicotyledonous plants/cyperaceae in rice {e.g. B69)} | 1: to :1 | 1: to :2 |
| Bd) Herbicides against grasses and dicotyledonous | | |

-continued

| Type B compounds | Mixing ratios Ab):B | |
|---|---|---|
| | standard | preferred |
| plants/cyperaceae in rice {e.g. B70)} | | |
| Bd) Herbicides against grasses and dicotyledonous plants/cyperaceae in rice {e.g. B71)} | 1: to :1 | 1: to :2 |
| Bd) Herbicides against grasses and dicotyledonous plants/cyperaceae in rice {e.g. B72)} | 1: to :1 | 1: to :2 |
| Bd) Herbicides against grasses and dicotyledonous plants/cyperaceae in rice {e.g. B73)} | 1: to :1 | 1: to :2 |

Preferred herbicidal compositions of the invention have, in a synergistically effective amount, A) at least one herbicidally active compound from the group of the substituted phenylsulfonylureas of the formula I and their agriculturally accepted, i.e. acceptable and compatible, salts

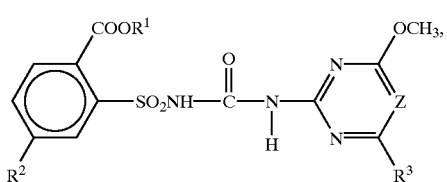

in which
R¹ is $(C_1-C_8)$-alkyl, $(C3-1-C_4)$-alkenyl, $(C3-1-C_4)$-alkynyl or $(C_1-C_4)$-alkyl, which is mono- to tetrasubstituted by radicals from the group consisting of halogen and $(C_1-C_2)$-alkoxy;
R² is I or $CH_2NHSO_2CH_3$;
R³ is methyl or methoxy; and
Z is N or CH;
in combination with
at least one herbicidally active compound from the group of the compounds B' consisting of
B1) butachlor,
B2) butenachlor,
B3) thenylchlor,
B4) pretilachlor,
B5) mefenacet,
B5a) Bay FOE 5043,
B6) naproanilid,
B7) propanil,
B8) etobenzanid,
B9) dimepiperate,
B10) molinate,
B11) thiobencarb,
B12) pyributicarb,
B13) quinclorac,
B14a) sulcotrione,
B15) cycloxydim
B16) sethoxydim
B17) NBA 061,
B18) piperophos,
B19) anilofos,
B21) haloxyfop,
B22) cyhalofop,
B23) JC-940,
B24) dithiopyr,
B25) bromobutide,
B26) cinmethylin,
B27) CH-900,
B32) acifluorfen,
B34) chlorimuron,
B37) picloram,
B38) carfentrazon
B40) triclopyr,
B41) benfuresate,
B42) daimuron,
B44) clomazon,
B45) benzofenap,
B46) pyrazolynate,
B47) pyrazoxyfen,
B49) KIH 6127,
B50) oxadiazon,
B51) oxadiargyl,
B56) dalapon,
B58) bensulfuron,
B59) pyrazosulfuron,
B60) cinosulfuron,
B61) imazosulfuron,
B62) AC 322, 140 (cyclosulfamuron),
B63a) ethoxysulfuron (HOE 095404),
B64) azimsulfuron (DPX-A8947),
B66) prometryn,
B67) simetryn,
B68) thiazopyr,
B69) pyrazophos,
B70) pentoxazone,
B71) indanofan,
B72) LGC 40863
and
B73) MY 100
or in combination with two or more herbicidally active compounds from the group of the compounds B".
B1) butachlor,
B2) butenachlor,
B3) thenylchlor,
B4) pretilachlor,
B5) mefenacet,
B5a) bay FOE 5043,
B6) naproanilid,
B7) propanil,
B8) etobenzanid,
B9) dimepiperate,
B10) molinate,
B11) thiobencarb,
B12) pyributicarb,
B13) quinclorac,
B14a) sulcotrione,
B15) cycloxydim
B16) sethoxydim
B17) NBA 061,
B18) piperophos,
B19) anilofos, B20) fenoxaprop, fenoxaprop-P,
B21) haloxyfop,
B22) cyhalofop,
B23) JC-940,
B24) dithiopyr,
B25) bromobutide,
B26) cinmethylin,
B27) CH-900,
B28) 2,4-D,
B29) mecoprop, mecoprop-P,
B30) MCPA,
B31) dicamba,
B32) acifluorfen,
B33a)

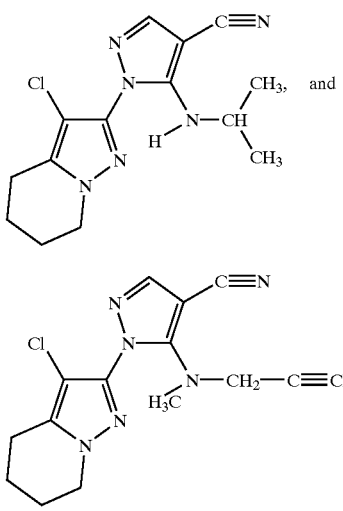

B34) chlorimuron,
B35) triasulfuron,
B36) ioxynil,
B37) picloram,
B38) carfentrazon,
B39) bentazon,
B40) triclopyr,
B41) benfuresate,
B42) daimuron,
B43) pendimethalin,
B44) clomazon,
B45) benzofenap,
B46) pyrazolynate,
B47) pyrazoxyfen,
B48) KIH 2023,
B49) KIH 6127,
B50) oxadiazon,
B51) oxadiargyl,
B52) acetochlor,
B53) metolachlor,
B54) metosulam,
B55) oxyfluorfen,
B56) dalapon,
B57) metsulfuron,
B58) bensulfuron,
B59) pyrazosulfuron,
B60) cinosulfuron,
B61) imazosulfuron,
B62) AC 322,140 (cyclosulfamuron),
B63a) ethoxysulfuron (HOE 095404),
B64) azimsulfuron (DPX-A8947),
B65) nicosulfuron, B66) prometryn,
B67) simetryn,
B68) thiazopyr,
B69) pyrazophos,
B70) pentoxazone,
B71) indanofan,
B72) LGC 40863 and
B73) MY 100
where in the case B" at least one of the compounds from group B" also has to belong to group B'.

The active compound combinations according to the invention can be present both as a mix of the two components, in which case they are applied in a customary manner diluted with water, or they can also be prepared as a so-called tank mix by joint dilution of the separately formulated components with water.

The active compounds of types A and B can be formulated in various ways, depending on the prevailing biological and/or chemicophysical parameters.

The following possibilities are suitable formulations:

Wettable powders (WP), emulsifiable concentrates (EC), water-soluble powders (SP), water-soluble concentrates (SL), concentrated emulsions (EW), such as oil in-water and water-in-oil emulsions, sprayable solutions or emulsions, capsule suspensions (CS), oil- or water-based dispersions (SC), suspoemulsions, suspension concentrates, dusts (DP), oil-miscible solutions, seed dressings, granules (GR) in the form of microgranules, spray granules, coated granules and absorption granules, granules for broadcasting and soil application, water-soluble granules (SG), water-dispersible granules (WG), ULV formulations, microcapsules and waxes.

Among these, preference is given to water-soluble wettable powders (WP), water-dispersible granules (WG), water-emulsifiable granules (EC), suspoemulsions (SE) and oil-suspension concentrates (SC).

These individual types of formulation are known in principle and are described, for example, in: Winnacker-Kuchler, "Chemische Technologie" [Chemical Technology], volume 7, C. Hauser Verlag, Munich, 4th Ed. 1986; Wade van Valkenburg, "Pesticide Formulations", Marcel Dekker N. Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N. J.; H. v. Olphen "Introduction to Clay Colloid Chemistry", 2nd Ed., J. Wiley & Sons, N. Y.; Marsden "Solvents Guide", 2nd Ed., Interscience, N. Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N. Y. 1964; Schonfeldt, "Grenzflachenaktive Athylenoxidaddukte", [Surface-active ethylene oxide adducts], Wiss. Verlagsgesellschaft, Stuttgart 1976; Winnacker-Kuchler "Chemische Technologie", [Chemical Technology], Volume 7, C. Hauser Verlag Munich, 4th Ed. 1986.

Based on these formulations, it is also possible to prepare combinations with pesticidally active compounds, herbicides, insecticides, fungicides, and also antidotes, safeners, fertilizers and/or growth regulators, for example in the form of a ready mix or a tank mix.

The herbicide combinations of the invention are prepared particularly advantageously by formulating the compounds of the formula I or salts thereof (type A compounds) with one or more compounds of type B similar to a conventional crop protection formulation from the group consisting of water-soluble wettable powders (WP), water-dispersible granules (WDG), water-emulsifiable granules (WEG), suspoemulsions (SE) and oil suspension concentrates (SC).

Wettable powders are preparations which are uniformly dispersible in water and which, besides the active compounds, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates or alkylarylsulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance.

Emulsifiable concentrates are prepared by dissolving the active compound or active compounds in an organic solvent, for example butanol, cyclohexanone, dimethylformamide, xylene, or else higher-boiling aromatics or hydrocarbons with the addition of one or more ionic and/or nonionic surfactants (emulsifiers). Examples of emulsifiers which can be used are: calcium salts of alkylarylsulfonic acids, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates (for example block copolymers), alkyl polyethers, sorbitan fatty acid esters, polyoxyethylene sorbitan fatty acid esters or other polyoxyethylene sorbitan esters.

Dusts are obtained by grinding the active compound or the active compounds with finely divided substances, for example talc, natural clays such as kaolin, bentonite and pyrophyllite, or diatomaceous earth.

Granules can be prepared either by spraying the active compound or the active compounds onto adsorptive granulated inert material or by applying active compound concentrates to the surface of carriers such as sand, kaolinites or of granulated inert material by means of binders, for example polyvinyl alcohol, sodium polyacrylate or else mineral oils.

Water-dispersible granules are generally prepared by the customary processes such as spray drying, fluidized-bed granulation, disk granulation, mixing with high-speed mixers and extrusion without solid inert material. It is also possible to granulate suitable active compounds in the manner customarily used for preparing fertilizer granules—if appropriate in a mixture with fertilizers.

Generally, the agrochemical preparations according to the invention comprise 0.1 to 99% by weight, in particular 2 to 95% by weight, very particularly 3 to 92% by weight, of active compounds of types A and B, in addition to customary formulation auxiliaries.

The concentrations of the active compounds A+B in the formulations may vary. In wettable powders, the active compound concentration is, for example, approximately 10 to 95% by weight, the remainder to 100% by weight being composed of customary formulation components. In the case of emulsifiable concentrates, the active compound concentration may amount to approximately 1 to 85% by weight, preferably 5 to 80% by weight. Formulations in the form of dusts comprise approximately 1 to 25% by weight, in most cases 5 to 20% by weight, of active compounds, and sprayable solutions comprise approximately 0.2 to 25% by weight, preferably 2 to 20% by weight, of active compounds. The active compound content of granules such as dispersible granules depends partly on whether the active compound is in liquid or solid form and on which granulation auxiliaries and fillers are being used. In general, the content of the water-dispersible granules amounts to between 10 and 90% by weight.

In addition, the abovementioned active compound formulations comprise, if appropriate, the tackifiers, wetting agents, dispersants, emulsifiers, penetrants, preservatives, antifreeze agents, solvents, fillers, colorants, carriers, antifoams, evaporation inhibitors and pH and viscosity regulators which are customary in each case.

Owing to the relatively low application rate of the combinations of A+B according to the invention, they are generally already very well tolerated. In particular, the combinations according to the invention permit a reduction of the absolute application rate, compared with the individual application of a herbicidally active compound. However, to increase the tolerability and/or selectivity of the herbicide combinations according to the invention, if desired, even more, it is advantageous to apply these jointly in a mixture or successively at different times together with safeners or antidotes. Suitable safeners or antidotes for the combinations according to the invention are the compounds known, for example, from EP-A-333 131 (ZA-89/1960), EP-A-269 806, (U.S. Pat. No. 4,891,057), EP-A-346 620 (AU-A-89/34951) and the international patent applications PCT/EP 90/01966 (WO-91/08202) and PCT/EP 90/02020 (WO-91/078474) and the literature cited therein, or they can be prepared by the methods described therein. Further suitable safeners are known from EP-A-94 349 (U.S. Pat. No. 4,902,304), EP-A-191 736 (U.S. Pat. No. 4,881,966) and EP-A-0 492 366 and the literature cited therein.

In the most favorable case, the herbicidal mixtures or use combinations of the invention additionally comprise C) one or more compounds of the formulae C1 and C2,

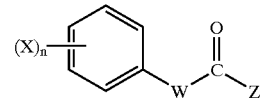

(C1)

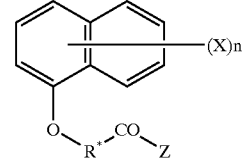

(C2)

in which

X is hydrogen, halogen, $(C_1-C_4)$-alkyl, $(C_1-C_4)$-alkoxy, nitro or $(C_1-C_4)$-haloalkyl, Z is $OR^1$, $SR^1$, $NR^1R$, where R is hydrogen, $(C_1-C_6)$-alkyl, $(C_1-C_6)$-alkoxy or unsubstituted or substituted phenyl, or is a saturated or unsaturated 3- to 7-membered heterocycle having at least one nitrogen atom and up to three hetero atoms which is linked to the carbonyl group via the nitrogen atom and which is unsubstituted or substituted by radicals selected from the group consisting of $(C_1-C_4)$-alkyl, $(C_1-C_4)$-alkoxy or unsubstituted or substituted phenyl, preferably a radical of the formula $OR^1$, $NHR^1$ or $N(CH_3)_2$, in particular $OR^1$, R* is a $(C_1-C_2)$-alkylene chain $(=(C_1-C_2)$-alkanediyl chain) which may additionally be substituted by one or two $(C_1-C_4)$-alkyl radicals or by $[(C_1-C_3)$-alkoxy] carbonyl, preferably —$CH_2$—, $R^1$ is hydrogen, $(C_1-C_{18})$-alkyl, $(C_3-C_{12})$-cycloalkyl, $(C_2-C_8)$-alkenyl or $(C_2-C_8)$-alkynyl, where the abovementioned carbon-containing radicals are unsubstituted or mono- or poly-substituted, preferably up to trisubstituted, by identical or different radicals selected from the group consisting of halogen, hydroxyl, $(C_1–C_8)$-alkoxy, $(C_1–C_8)$-alkylthio, $(C_2–C_8)$-alkenylthio, $(C_2–C_8)$-alkynylthio, $(C_2–C_8)$-alkenyloxy, $(C_2–C_8)$-alkynyloxy, $(C_3–C_7)$-cycloalkyl, $(C_3–C_7)$-cycloalkoxy, cyano, mono- and di-$(C_1–C_8)$-alkylamino, carboxy, $(C_1–C_8)$-alkoxy-carbonyl, $(C_2–C_8)$-alkenyloxy-carbonyl, $(C_1–C_8)$-alkylthio-carbonyl, $(C_2–C_8)$-alkynyloxy-carbonyl, $(C_1–C_8)$-alkyl-carbonyl, $(C_2–C_8)$-alkenyl-carbonyl, $(C_2–C_8)$-alkynyl-carbonyl, 1-(hydroxyimino)-$(C_1–C_6)$-alkyl, 1-[$(C_1–C_4)$-alkylimino)]-$(C_1–C_4)$-alkyl, 1-[$(C_1–C_4)$-alkoxyimino]-$(C_1–C_6)$-alkyl, $(C_1–C_8)$-alkyl-carbonylamino, $(C_2–C_8)$-alkenyl-carbonylamino, $(C_2–C_8)$-alkynyl-carbonylamino, aminocarbonyl, $(C_1–C_8)$-alkylaminocarbonyl, di-$(C_1–C_6)$-alkyl-aminocarbonyl, $(C_2–C_6)$-alkenyl-aminocarbonyl, $(C_2–C_6)$-alkynyl-aminocarbonyl, $(C_1–C_8)$-alkoxy-carbonylamino, $(C_1–C_8)$-alkyl-aminocarbonylamino, $(C_1–C_6)$-alkylcarbonyloxy which is unsubstituted or substituted by halogen, $NO_2$, $(C_1–C_4)$-alkoxy or unsubstituted or substituted phenyl, $(C_2–C_6)$-alkenyl-carbonyloxy, $(C_2–C_6)$-alkynyl-carbonyloxy, $(C_1–C_8)$-alkyl-sulfonyl, phenyl, phenyl-$(C_1–C_6)$-alkoxy, phenyl-$(C_1–C_6)$-alkoxy-carbonyl, phenoxy, phenoxy-$(C_1–C_6)$-alkoxy, phenoxy-$(C_1–C_6)$-alkoxy-carbonyl, phenylcarbonyloxy, phenylcarbonylamino, phenyl-$(C_1–C_6)$-alkyl-carbonylamino, where the last nine radicals are unsubstituted in the phenyl ring or mono- or polysubstituted, preferably up to trisubstituted, by identical or different radicals selected from the group consisting of halogen, $(C_1–C_4)$-alkyl, $(C_1–C_4)$-alkoxy, $(C_1–C_4)$-haloalkyl, $(C_1–C_4)$-haloalkoxy and nitro, and radicals of the formulae $SiR'_3$, —O—$SiR'_3$, $R'_3Si$—$(C_1–C_8)$-alkoxy, —CO—O—$NR'_2$, —O—N=$CR'_2$, —N=$CR'_2$, —O—$NR'_2$, $CH(OR')_2$ and —O—$(CH_2)_m$—$CH(OR'_2)_2$, where the R' in the abovementioned formulae independently of one another are each hydrogen, $(C_1–C_4)$-alkyl, phenyl which is unsubstituted or mono- or polysubstituted, preferably up to trisubstituted, by identical or different radicals selected from the group consisting of halogen, $(C_1–C_4)$-alkyl, $(C_1–C_4)$-alkoxy, $(C_1–C_4)$-haloalkyl, $(C_1–C_4)$-haloalkoxy and nitro, or, as a pair, are a $(C_2–C_6)$-alkylene chain, and m=0 to 6, and a radical of the formula R"O—CHR"' (OR")-$(C_1–C_6)$-alkoxy, where the radicals R" independently of one another are each $(C_1–C_4)$-alkyl or together a $(C_1–C_6)$-alkylene radical and R"' is hydrogen or $(C_1–C_4)$-alkyl, R is hydrogen, $(C_1–C_6)$-alkyl, $(C_1–C_6)$-alkoxy or unsubstituted or substituted phenyl, n is an integer from 1 to 5, preferably 1 to 3, W is a bivalent heterocyclic radical having 5 ring atoms of the formulae W1 to W4

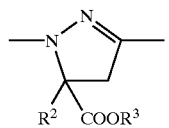

(W1)

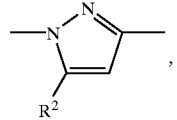

(W2)

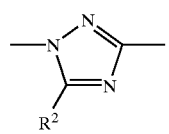

(W3)

(W4)

—CH$_2$— in which
R$^2$ is hydrogen, $(C_1–C_8)$-alkyl, $(C_1–C_8)$-haloalkyl, $(C_3–C_{12})$-cycloalkyl or unsubstituted or substituted phenyl and
R$^3$ is hydrogen, $(C_1–C_8)$-alkyl, $(C_1–C_8)$-haloalkyl, $(C_1–C_4)$-alkoxy-$(C_1–C_4)$-alkyl, $(C_1–C_6)$-hydroxyalkyl, $(C_3–C_{12})$-cycloalkyl or tri-$((C_1–C_4)$-alkyl)silyl, or the salts of the abovementioned compounds.

Unless specifically defined otherwise, the following definitions apply to the radicals both in the formulae mentioned for the safeners and the formulae mentioned elsewhere in this description, and in particular also for the compounds of the formulae I, II, III and IV:

alkyl, alkenyl and alkynyl are straight-chain or branched and have up to 8, preferably up to 4, carbon atoms; this applies correspondingly to the aliphatic moiety of substituted alkyl, alkenyl and alkynyl radicals or radicals derived therefrom such as haloalkyl, hydroxyalkyl, alkoxycarbonyl, alkoxy, alkanoyl, haloalkoxy, etc.;

alkyl is, for example, methyl, ethyl, n-propyl, isopropyl, n-butyl, i-butyl, t-butyl and 2-butyl, pentyls, in particular n-pentyl and neo-pentyl, hexyls such as n-hexyl and i-hexyl and 1,3-dimethylbutyl, heptyls such as n-heptyl, 1-methylhexyl and 1,4-dimethylpentyl, alkenyl is, for example, inter alia allyl, 1-methylprop-2-en-1-yl, but-2-en-1-yl, but-3-en-1-yl, 1-methylbut-3-ene and 1-methylbut-2-ene; alkynyl is, inter alia, propargyl, but-2-yn-1-yl, but-3-yn-1-yl, 1-methylbut-3-yne;

cycloalkyl preferably has 3 to 8 carbon atoms and is, for example, cyclobutyl, cyclopentyl, cyclohexyl or cycloheptyl. Cycloalkyl may carry up to two $(C_1–C_4)$-alkyl radicals as substituents.

Halogen is fluorine, chlorine, bromine or iodine, preferably fluorine, chlorine or bromine, in particular fluorine or chlorine; haloalkyl, -alkenyl and -alkynyl are alkyl, alkenyl and alkynyl, respectively, which are mono-, di- or polysubstituted by halogen, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, inter alia $OCF_3$, $OCHF_2$, $OCH_2F$, $CF_3CF_2O$, $CF_3CH_2O$;

aryl preferably has 6 to 12 carbon atoms and is, for example, phenyl, naphthyl or biphenyl, preferably phenyl. This applies correspondingly to radicals derived therefrom such as aryloxy, aroyl or aroylalkyl;

unsubstituted or substituted phenyl is, for example, phenyl which is unsubstituted or mono- or polysubstituted, preferably mono-, di- or trisubstituted, by identical or different radicals selected from the group consisting of halogen, $(C_1–C_4)$-alkyl, $(C_1–C_4)$-alkoxy, $(C_1–C_4)$-haloalkyl, ($C_1$–$C_4$)-haloalkoxy, ($C_1$–$C_4$)-alkylthio, ($C_2$–$C_5$)-alkoxycarbonyl, ($C_2$–$C_5$)-alkylcarbonyloxy, carbonamide, ($C_2$–$C_5$)-alkylcarbonylamino, di[($C_1$–$C_4$)-alkyl]aminocarbonyl and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl or o-, m- and p-methoxyphenyl. This applies correspondingly to unsubstituted or substituted aryl.

Of particular interest are herbicidal compositions according to the invention where in the compounds of the formula C1 and C2

$R^1$ is hydrogen, ($C_1$–$C_8$)-alkyl, ($C_3$–$C_7$)-cycloalkyl, ($C_2$–$C_8$)-alkenyl or ($C_2$–$C_8$)-alkynyl, where the abovementioned carbon-containing radicals are unsubstituted or mono- or polysubstituted by halogen or mono- or disubstituted, preferably monosubstituted, radicals selected from the group consisting of hydroxyl, ($C_1$–$C_4$)-alkoxy, ($C_1$–$C_4$)-alkylthio, ($C_2$–$C_4$)-alkenyloxy, ($C_2$–$C_6$)-alkynyloxy, mono- and di-(($C_1$–$C_2$)-alkyl)amino, ($C_1$–$C_4$)-alkoxy-carbonyl, ($C_2$–$C_4$)-alkenyloxycarbonyl, ($C_2$–$C_4$)-alkynyloxycarbonyl, ($C_1$–$C_4$)-alkyl-carbonyl, ($C_2$–$C_4$)-alkenyl-carbonyl, ($C_2$–$C_4$)-alkynyl-carbonyl, ($C_1$–$C_4$)-alkylsulfonyl, phenyl, phenyl-($C_1$–$C_4$)-alkoxycarbonyl, phenoxy, phenoxy-($C_1$–$C_4$)-alkoxy, phenoxy-($C_1$–$C_4$)-alkoxy-carbonyl, where the last six radicals are unsubstituted in the phenyl ring or mono- or polysubstituted by radicals selected from the group consisting of halogen, ($C_1$–$C_2$)-alkyl, ($C_1$–$C_2$)-alkoxy, ($C_1$–$C_2$)-haloalkyl, ($C_1$–$C_2$)-haloalkoxy and nitro, and radicals of the formulae $SiR'_3$, —O—N=$CR'_2$, —N=$CR'_2$ and —O—$NR'_2$—CH($OR'$)$_2$, where the R' in the abovementioned formulae independently of one another are each hydrogen, ($C_1$–$C_2$)-alkyl, phenyl which is unsubstituted or mono- or polysubstituted by radicals selected from the group consisting of halogen, ($C_1$–$C_2$)-alkyl, ($C_1$–$C_2$)-alkoxy, ($C_1$–$C_2$)-haloalkyl, ($C_1$–$C_2$)-haloalkoxy and nitro, or as a pair are a ($C_4$–$C_5$)-alkanediyl chain, $R^2$ is hydrogen, ($C_1$–$C_8$)-alkyl, ($C_1$–$C_6$)-haloalkyl, ($C_3$–$C_7$)-cycloalkyl or phenyl and $R^3$ is hydrogen, ($C_1$–$C_8$)-alkyl, ($C_1$–$C_8$)-haloalkyl, (($C_1$–$C_4$)-alkoxy)-($C_1$–$C_4$)-alkyl, ($C_1$–$C_6$)-hydroxyalkyl, ($C_3$–$C_7$)-cycloalkyl or tri-(($C_1$–$C_4$)-alkyl)silyl.

Also of particular interest are herbicidal compositions according to the invention where in the compounds of the formulae C1 and C2

X is hydrogen, halogen, methyl, elthyl, methoxy, ethoxy, ($C_1$–$C_2$)-haloalkyl, preferably hydrogen, halogen or ($C_1$–$C_2$)-haloalkyl.

Preference is given to herbicidal compositions according to the invention where in the compounds of the formula C1

X is hydrogen, halogen, nitro or ($C_1$–$C_4$)-haloalkyl,
Z is a radical of the formula $OR^1$,
n is an integer from 1 to 3,
$R^1$ is hydrogen, ($C_1$–$C_8$)-alkyl, ($C_3$–$C_7$)-cycloalkyl, where the abovementioned carbon-containing radicals are unsubstituted or mono- or polysubstituted by radicals from the group consisting of halogen or mono- or disubstituted, preferably unsubstituted or monosubstituted by radicals selected from the group consisting of hydroxyl, ($C_1$–$C_4$)-alkoxy, (($C_1$–$C_4$)-alkoxy)-carbonyl, ($C_2$–$C_6$)-alkenyloxy-carbonyl, (($C_2$–$C_6$)-alkynyloxy)-carbonyl and radicals of the formulae $SiR'_3$, —O—N=$CR'_2$, —N=$CR'_2$, —O—$NR'_2$, where the radicals R' in the abovementioned formulae independently of one another are each hydrogen or ($C_1$–$C_4$)-alkyl or as a pair are a ($C_4$–$C_5$)-alkylene chain, $R^2$ is hydrogen, ($C_1$–$C_8$)-alkyl, ($C_1$–$C_6$)-haloalkyl, ($C_3$–$C_7$)-cycloalkyl or phenyl and $R^3$ is hydrogen, ($C_1$–$C_8$)-alkyl, ($C_1$–$C_8$)-haloalkyl, (($C_1$–$C_4$)-alkoxy)-($C_1$–$C_4$)-alkyl, ($C_1$–$C_6$)-hydroxyalkyl, ($C_3$–$C_7$)-cycloalkyl or tri-(($C_1$–$C_4$)-alkyl)silyl.

Preference is also given to herbicidal compositions according to the invention where in the compounds of the formula C2

X is hydrogen, halogen, or ($C_1$–$C_4$)-haloalkyl and n is an integer from 1 to 3, preferably $(X)_n$=5-Cl,
Z is a radical of the formula $OR^1$,
R* is $CH_2$ and
$R^1$ is hydrogen, ($C_1$–$C_8$)-alkyl, ($C_1$–$C_8$)-halo-alkyl, (($C_1$–$C_4$)-alkoxy)-($C_1$–$C_4$)-alkyl or (($C_1$–$C_4$)-alkenyloxy)-($C_1$–$C_4$)-alkyl, preferably ($C_1$–$C_8$)-alkyl.

Particular preference is given to herbicidal compositions according to the invention comprising compounds of the formula C1 in which W is W1
X is hydrogen, halogen or ($C_1$–$C_2$)-haloalkyl and n=1–3, in particular $(X)_n$=2,4-$Cl_2$,
Z is a radical of the formula $OR^1$,
$R^1$ is hydrogen, ($C_1$–$C_8$)-alkyl, ($C_1$–$C_4$)-halo-alkyl, ($C_1$–$C_4$)-hydroxyalkyl, ($C_3$–$C_7$)-cyclo-alkyl, (($C_1$–$C_4$)-alkoxy)-($C_1$–$C_4$)-alkyl, tri-($C_1$–$C_2$)-alkyl)silyl, preferably ($C_1$–$C_4$)-alkyl,
$R^2$ is hydrogen, ($C_1$–$C_8$)-alkyl, ($C_1$–$C_4$)-haloalkyl or ($C_3$–$C_7$)-cycloalkyl, preferably hydrogen or ($C_1$–$C_4$)-alkyl and
$R^3$ is hydrogen, ($C_1$–$C_8$)-alkyl, ($C_1$–$C_4$)-halo-alkyl, ($C_1$–$C_4$)-hydroxyalkyl, ($C_3$–$C_7$)-cyclo-alkyl, (($C_1$–$C_4$)-alkoxy)-($C_1$–$C_4$)-alkyl or tri-(($C_1$–$C_2$)-alkyl)silyl, preferably H or ($C_1$–$C_4$)-alkyl.

Particular preference is also given to herbicidal compositions according to the invention comprising compounds of the formula C1 in which W is W2
X is hydrogen, halogen or ($C_1$–$C_2$)-haloalkyl and n=1–3, in particular $(X)_n$=2,4-$Cl_2$,
Z is a radical of the formula $OR^1$,
$R^1$ is hydrogen, ($C_1$–$C_8$)-alkyl, ($C_1$–$C_4$)-halo-alkyl, ($C_1$–$C_4$)-hydroxyalkyl, ($C_3$–$C_7$)-cyclo-alkyl, (($C_1$–$C_4$)-alkoxy)-($C_1$–$C_4$)-alkyl, tri-(($C_1$–$C_2$)-alkyl)silyl, preferably ($C_1$–$C_4$)-alkyl, and
$R^2$ is hydrogen, ($C_1$–$C_8$)-alkyl, ($C_1$–$C_4$)-halo-alkyl, ($C_3$–$C_7$)-cycloalkyl or phenyl, preferably hydrogen or ($C_1$–$C_4$)-alkyl.

Particular preference is also given to herbicidal compositions according to the invention comprising compounds of the formula C1 in which W is W3
X is hydrogen, halogen or ($C_1$–$C_2$)-haloalkyl and n=1–3, in particular $(X)_n$=2,4-$Cl_2$,
Z is a radical of the formula $OR^1$,
$R^1$ is hydrogen, ($C_1$–$C_8$)-alkyl, ($C_1$–$C_4$)-halo-alkyl, ($C_1$–$C_4$)-hydroxyalkyl, ($C_3$–$C_7$)-cyclo-alkyl, (($C_1$–$C_4$)-alkoxy)-($C_1$–$C_4$)-alkyl, tri-(($C_1$–$C_2$)-alkyl)silyl, preferably ($C_1$–$C_4$)-alkyl, and
$R^2$ is ($C_1$–$C_8$)-alkyl or ($C_1$–$C_4$)-haloalkyl, preferably $C_1$-haloalkyl.

Particular preference is also given to herbicidal compositions according to the invention comprising compounds of the formula C1 in which W is W4

X is hydrogen, halogen, nitro, $(C_1-C_4)$-alkyl, $(C_1-C_4)$-alkoxy or $(C_1-C_2)$-haloalkyl and n=1–3, preferably $CF_3$ or $(C_1-C_4)$-alkoxy, Z is a radical of the formula $OR^1$ and $R^1$ is hydrogen, $(C_1-C_4)$-alkyl or $((C_1-C_4)$-alkoxy)-carbonyl-$((C_1-C_4)$-alkyl, preferably $((C_1-C_4)$-alkoxy)-CO—$CH_2$—, $((C_1-C_4)$-alkoxy)-CO—C$(CH_3)$H—, HO—CO—$CH_2$— or HO—CO—C$(CH_3)$H—.

The compounds of the formula C1 are known from EP-A-0 333 131, EP-A-0 269 806, EP-A-0 346 620, International Patent Application PCT/EP 90/01966 and International Patent Application PCT/EP 90/02020 and the literature cited therein, or they can be prepared by or similar to the methods described therein. The compounds of the formula C2 are known from EP-A-0 086 750, EP-A-0 094 349 and EP-A-0 191 736 and the literature cited therein, or they can be prepared by or similar to the methods described therein. Furthermore, they are proposed in DE-A-40 41 121.4.

Particularly preferred antidotes or safeners or groups of compounds which have proved themselves suitable as safeners or antidotes for the product combinations of the invention described above are, inter alia:

a) compounds of the type of the dichlorophenylpyrazolin-3-carboxylic acid (i.e. the formula C1 where W=W1 and $(X)_n$=2,4-$Cl_2$), preferably compounds such as ethyl 1-(2,4-dichlorophenyl)-5-(ethoxycarbonyl)-5-methyl-2-pyrazolin-3-carboxylate (compound C1-1) and related compounds as described in the International Application WO 91/07874 (PCT/EP 90/02020);

b) derivatives of dichlorophenylpyrazolecarboxylic acid (i.e. the formula C1 where W=W2 and $(X)_n$=2,4-$Cl_2$), preferably compounds such as ethyl 1-(2,4-dichlorophenyl)-5-methylpyrazole-3-carboxylate (compound C1-2), ethyl 1-(2,4-dichlorophenyl)-5-isopropylpyrazole-3-carboxylate (compound C1-3), ethyl 1-(2,4-dichlorophenyl)-5-(1,1-dimethylethyl)pyrazole-3-carboxylate (compound C1-4), ethyl 1-(2,4-dichlorophenyl)-5-phenylpyrazole-3-carboxylate (compound C1-5) and related compounds as described in EP-A-0 333 131 and EP-A-0 269 806;

c) compounds of the type of the triazolecarboxylic acids (i.e. the formula C1 where W=W3 and $(X)_n$=2,4-$Cl_2$), preferably compounds such as ethyl 1-(2,4-dichlorophenyl)-5-(trichloromethyl-(1H)-1,2,4-triazole-3-carboxylate (compound C1-6, fenchlorazole) and related compounds (see EP-A-0 174 562 and EP-A-0 436 620);

d) compounds of the type of the dichlorobenzyl-2-isoxazolin-3-carboxylic acid, (i.e. the formula C1 where W=W4 and $(X)_n$=2,4-$Cl_2$), compounds of the type of the 5-benzyl- or 5-phenyl-2-isoxazolin-3-carboxylic acid, preferably compounds such as ethyl 5-(2,4-dichlorobenzyl)-2-isoxazolin-3-carboxylate (compound C1-7) or ethyl 5-phenyl-2-isoxazolin-3-carboxylate (compound (C1-8) and related compounds as described in the International Patent Application WO 91/08202 (PCT/EP 90/01966);

e) compounds of the type of the 8-quinolinoxyacetic acid (i.e. of the formula C2 where $(X)_n$=5-Cl, hydrogen, Z=$OR^1$, $R^*$=$CH_2$), preferably compounds such as 1-methylhex-1-yl(5-chloro-8-quinolinoxy)acetate (C2-1), 1,3-dimethylbut-1-yl(5-chloro-8-quinolinoxy)acetate (C2-2), 4-allyloxybutyl(5-chloro-8-quinolinoxy)acetate (C2-3), 1-allyloxyprop-2-yl(5-chloro-8-quinolinoxy) acetate (C2-4), ethyl(5-chloro-8-quinolinoxy)acetate (C2-5), methyl(5-chloro-8-quinolinoxy)acetate (C2-6), allyl (5-chloro-8-quinolinoxy)acetate (C2-7), 2-(2-propylideneiminoxy)-1-ethyl 5-chloro-8-quinolinoxy) acetate (C2-8), 2-oxoprop-1-yl(5-chloro-8-quinolinoxy) acetate (C2-9) and related compounds as described in EP-A-0 086 750, EP-A-0 094 349 and EP-A-0 191 736 or EP-A-0 492 366;

f) compounds of the type of the (5-chloro-8-quinolinoxy) malonic acid, i.e. the formula C2 where $(X)_n$=5-Cl, hydrogen, Z=$OR^1$, $R^*$=—CH(COO-alkyl)-, preferably compounds such as diethyl(5-chloro-8-quinolinoxy) malonate, diallyl(5-chloro-8-quinolinoxy)malonate, methyl ethyl(5-chloro-8-quinolinoxy)malonate and related compounds as described and proposed in the German Patent Application P 40 41 121.4 or the European Patent Application EP-A-0 582 198;

g) active compounds of the type of the phenoxyacetic or phenoxypropionic acid derivatives or of the aromatic carboxylic acids such as, for example, 2,4-dichlorophenoxyacetic acid(ester) (2,4-D), 4-chloro-2-methylphenoxypropionic ester (mecoprop), MCPA or 3,6-dichloro-2-methoxybenzoic acid(ester) (dicamba);

h) compounds of the type of the 5,5-diphenyl-2-isoxazoline-3-carboxylic acid, preferably ethyl 5,5-diphenyl-2-isoxazoline-3-carboxylate (C3-1);

i) compounds which are known as safeners for rice, such as, for example, fenchlorim(=4,6-dichloro-2-phenylpyrimidine, Pesticide Manual, 11. Ed., 1997, pp. 511–512), dimepiperate(=S-1-methyl-1-phenyl piperidine-1-thiocarboxylate, Pesticide Manual, 11. Ed., 1997, pp. 404–405), daimuron(=1-(1-methyl-1-phenylethyl)-3-p-tolylurea, Pesticide Manual, 11. Edition, 1997, p. 330), cumyluron(=3-(2-chlorophenylmethyl)-1-(1-methyl-1-phenylethyl)urea, JP-A-60/087254), methoxyphenone(=3,3'-dimethyl-4-methoxybenzophenone), CSB(=1-bromo-4-(chloromethylsulfonyl) benzene, CAS Reg. No. 54091-06-4); where at least some of the compounds mentioned under a) to i) are furthermore described in EP-A-0 640 587, which is herewith referred to for disclosure purposes;

j) safeners and antidotes are known from WO 95/07897.

In a very particularly preferred embodiment according to the invention, the herbicidal compositions of the invention additionally comprise C) one or more isoxazolin(s) of the formula C3 and salts thereof

(C3)

in which $R^1$ is carboxyl, formyl or another acyl radical or a derivative of the three last-mentioned groups, $R^2$ is hydrogen, halogen, $C_1-C_{18}$-alkyl, $C_3-C_8$-cycloalkyl, $C_2-C_8$-alkenyl, $C_2-C_8$-alkynyl, $C_1-C_{18}$-alkenyloxy, $C_2-C_6$-alkynyloxy, $C_1-C_{18}$-alkylthio, $C_2-C_8$-alkenylthio, where each of the nine last-mentioned radicals is in each case unsubstituted or substituted by one or more radicals from the group consisting of halogen, nitro, cyano, $C_1-C_4$-alkoxy or $(C_1-C_8$-alkoxy)carbonyl, or $(C_1-C_8$-alkoxy)carbonyl, $R_3$ and $R_4$ independently of one another are an aliphatic, araliphatic or heteroaraliphatic radical having 1 to 30 carbon atoms which is unsubstituted or substituted by one or more functional groups, or is an aromatic or heteroaromatic radical which is unsubstituted or substituted.

From among these, compositions which, in addition to A and B compound(s) contain a compound of type C3 are of particular interest, where in the formula C3

$R^1$ is a radical of the formula

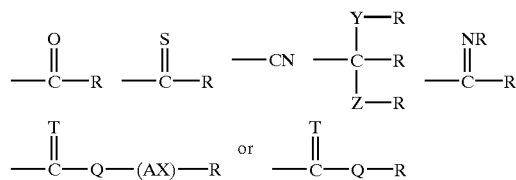

in which R, $R^T$, $R^5$, $R^6$, $R^7$, Y, T, Z, Q, $A_1$, $X_1$ and q are as defined below, R is hydrogen or an aliphatic, aromatic, heteroaromatic, araliphatic or heteroaraliphatic radical having 1 to 30 carbon atoms which is unsubstituted or substituted by one or more functional groups, $R^T$ is a radical of the formula —CO—R, —CS—R, —$NR^f R^g$, —N=$CR^h R^1$ or $SiR^a R^b R^c$, where R is as mentioned above and $R^f$, $R^g$, $R^h$ and $R^1$ independently of one another are hydrogen, $C_1$–$C_4$-alkyl, $C_2$–$C_4$-alkenyl, $C_2$–$C_4$-alkynyl, benzyl, phenyl or substituted phenyl or $R^f$ and $R^g$ together with the nitrogen atom are a 5- or 6-membered heterocycle which may contain up to two more heteroatoms from the group consisting of N, O and S and which may be substituted by $C_1$–$C_4$-alkyl and $R^a$, $R^b$ and $R^c$ independently of one anther are $C_1$–$C_4$-alkyl, $C_2$–$C_4$-alkenyl, $C_2$–$C_4$-alkynyl, phenyl or substituted phenyl, Y, Z independently of one another are oxygen, sulfur in its various oxidation stages, or —$NR^e$, where $R^e$ is defined analogously to $R^5$ or $R^6$, $R^5$, $R^6$ are identical or different and independently of one another are hydrogen, $C_1$–$C_6$-alkyl, $C_2$–$C_6$-alkenyl, $C_2$–$C_6$-alkynyl, ($C_1$–$C_4$-alkyl)carbonyl, where each of the four last-mentioned radicals may be unsubstituted or substituted by one or more substituents from the group consisting of halogen, $C_1$–$C_8$-haloalkoxy, nitro, cyano, hydroxyl, $C_1$–$C_8$-alkoxy and a $C_1$–$C_8$-alkoxy group in which one or more $CH_2$ groups are replaced by oxygen, and $C_1$–$C_8$-alkylthio, $C_1$–$C_6$-alkylsulfonyl $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy and amino, mono- and di-($C_1$–$C_4$-alkyl)amino, or are formyl or $SiR^a R^b R^c$, in which $R^a$, $R^b$ and $R^c$ independently of one another are $C_1$–$C_4$-alkyl, $C_2$–$C_4$-alkenyl, $C_2$–$C_4$-alkynyl or unsubstituted or substituted phenyl, or are $C_3$–$C_8$-cycloalkyl, $C_3$–$C_8$-cycloalkenyl, heterocyclyl having 3 to 7 ring atoms, aryl, heteroaryl or arylcarbonyl, where each of the six last-mentioned radicals is unsubstituted or substituted by one or more radicals from the group consisting of $C_1$–$C_8$-alkyl, halogen, $C_1$–$C_8$-haloalkoxy, nitro, cyano, hydroxyl, $C_1$–$C_8$-alkoxy and a $C_1$–$C_8$-alkoxy group in which one or more not directly adjacent $CH_2$ groups are replaced by oxygen, and $C_1$–$C_8$-alkylthio, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy and amino, mono- and di-($C_1$–$C_4$-alkyl)amino, or $R^5$, $R^6$ together are a $C_2$–$C_4$-alkylene chain or $C_2$–$C_4$-alkenylene chain which is unsubstituted or substituted by one or two radicals from the group consisting of methyl, ethyl, methoxy, ethoxy and halogen, and $R^7$ is hydrogen, $C_1$–$C_4$-alkyl, $C_2$–$C_4$-alkenyl, $C_2$–$C_4$-alkynyl, unsubstituted or substituted $C_6$–$C_{12}$-aryl or heteroaryl, benzyl, $C_1$–$C_4$-alkoxy, acyloxy, hydroxyl, —NH—CO—$NH_2$, —NH—CS—$NH_2$, mono- and di-($C_1$–$C_4$-alkyl)amino, acylamino, ($C_1$–$C_4$-alkyl)sulfonylamino, $C_6$–$C_{12}$-aryloxy, heteroaryloxy, arylsulfonylamino or arylamino, in which aryl or heteroaryl in the four last-mentioned radicals are unsubstituted or substituted by one or more radicals from the group consisting of halogen, nitro, ($C_1$–$C_4$)-alkyl, ($C_1$–$C_4$)-alkoxy, ($C_1$–$C_4$)-haloalkyl and ($C_1$–$C_4$)-haloalkoxy, T is O, S, $NR^8$, N—$OR^8$ or N—O-acyl, Q is O or S, q is an integer from 0 to 4, i is a running number which, if q is not 0, adopts the value of all integers from 1 to q, q being defined as above, $X_1$ independently of one another are O, S, $NR^9$, N—$(A_1 X_1)_q$—R $A_1$ independently of one another are unsubstituted or substituted $C_1$–$C_6$-alkylene, $C_2$–$C_6$-alkenylene, $C_2$–$C_6$-alkynyl, $C_3$–$C_6$-cycloalkenylene, heterocyclylene, arylene or heteroarylene and $R^8$, $R^9$ independently of one another are H, $C_1$–$C_4$-alkyl, $C_2$–$C_4$-alkenyl, $C_2$–$C_4$-alkynyl, $C_3$–$C_6$-cycloalkyl, $C_3$–$C_6$-cycloalkenyl, heterocyclyl, aryl or heteroaryl.

Furthermore of most particular interest are compositions according to the invention which comprise one or more compounds of type C3, where in the formula C3 at least one of the radicals $R^3$ and $R^4$ independently of one another is a radical of the formula

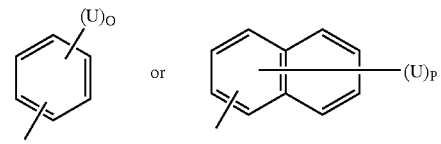

in which (U) represents identical or different radicals which, independently of one another, are hydrogen, cyano, nitro, amino or $C_1$–$C_8$-haloalkyl, $C_1$–$C_8$-haloalkoxy, $C_1$–$C_8$-alkyl, $C_1$–$C_8$-alkoxy, mono-($C_1$–$C_4$-alkyl) amino, di-($C_1$–$C_4$-alkyl)amino, $C_1$–$C_8$-alkylthio or $C_1$–$C_8$-alkylsulfonyl, where each of the eight last-mentioned radicals is unsubstituted or substituted by one or more identical or different substituents from the group consisting of halogen, $C_1$–$C_8$-haloalkoxy, nitro, cyano, hydroxyl, $C_1$–$C_8$-alkoxy and a $C_1$–$C_8$-alkoxy group in which one or more $CH_2$ groups are replaced by oxygen, $C_1$–$C_8$-alkylthio, $C_1$–$C_6$-alkylsulfinyl, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, mono- and di-($C_1$–$C_4$-alkyl)amino and ($C_1$–$C_8$-alkoxy)carbonyl, and o is an integer from 1 to 5 and p is an integer from 1 to 7, or a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyradizinyl and quinolinyl which is in each case unsubstituted or substituted by one or more of the abovementioned radicals U and R is H, $C_1$–$C_{18}$-alkyl, $C_3$–$C_{12}$-cycloalkyl, $C_2$–$C_8$-alkenyl or $C_2$–$C_8$-alkynyl, heterocyclyl, phenyl or heteroaryl, where each of the seven last-mentioned radicals independently of one another is unsubstituted or substituted by one or more radicals from the group consisting of halogen, cyano, thio, nitro, hydroxyl, $C_1$–$C_8$-alkyl, the latter only in the case of cyclic radicals, $C_1$–$C_8$-haloalkyl, $C_1$–$C_8$-alkoxy, $C_2$–$C_8$-alkenyloxy, $C_2$–$C_8$-alkynyloxy, $C_1$–$C_8$-haloalkoxy, $C_2$–$C_8$-alkenylthio, $C_2$–$C_8$-alkynylthio, $C_3$–$C_7$-cycloalkyl, $C_3$–$C_7$-cycloalkoxy, radicals of the formulae —NR*R** and —CO—NR*R** and —O—CO—NR*R** where R* and R** in the last-mentioned radicals independently of one another are hydrogen, $C_1$–$C_8$-alkyl, $C_2$–$C_8$-alkenyl, $C_2$–$C_8$-alkynyl, benzyl, phenyl or substituted phenyl and together with the nitrogen atom are a 3- to 8-membered heterocycle which may contain up to two more heteroatoms from the group consisting of N, O and S and which may be substituted by $C_1$–$C_4$-alkyl, and ($C_1$–$C_8$-alkoxy)carbonyl, ($C_1$–$C_8$-alkoxy)thiocarbonyl, ($C_2$–$C_8$-alkenyl)carbonyl, ($C_1$–$C_8$-alkoxy)thiocarbonyl, ($C_2$–$C_8$-alkenyloxy)carbonyl, ($C_1$–$C_8$-alkylthio)carbonyl, ($C_2$–$C_8$-alkenylthio)carbonyl, ($C_2$–$C_8$-alkynylthio)carbonyl, ($C_2$–$C_8$-alkynyloxy)carbonyl, formyl, ($C_1$–$C_8$-alkyl)carbonyl, ($C_2$–$C_8$-alkenyl)carbonyl, ($C_2$–$C_8$-alkynyl)carbonyl, $C_1$–$C_4$-alkylimino, $C_1$–$C_4$-alkoxyimino, ($C_1$–$C_8$-alkyl)carbonylamino, ($C_2$–$C_8$-alkenyl)carbonylamino, ($C_2$–$C_8$-alkynyl)carbonylamino, ($C_1$–$C_8$-alkoxy)carbonylamino, ($C_2$–$C_8$-alkenyloxy)carbonylamino, ($C_2$–$C_8$-alkynyloxy)carbonylamino, ($C_1$–$C_8$-alkyl)aminocarbonylamino, ($C_1$–$C_6$-alkyl)carbonyloxy which is unsubstituted or substituted by halogen, $NO_2$, $C_1$–$C_4$-alkoxy or optionally substituted phenyl, and ($C_2$–$C_6$-alkenyl)carbonyloxy, ($C_2$–$C_6$-alkynyl)carbonyloxy, ($C_1$–$C_8$-alkoxy)carbonyloxy, ($C_2$–$C_8$-alkenyloxy)carbonyloxy, ($C_2$–$C_8$-alkynyloxy)carbonyloxy, $C_1$–$C_8$-alkylsulfonyl, phenyl, phenyl-$C_1$–$C_6$-alkoxy, phenyl-($C_1$–$C_6$-alkoxy)carbonyl, phenoxy, phenoxy-$C_1$–$C_6$-alkoxy, phenoxy-($C_1$–$C_6$-alkoxy)-carbonyl, phenoxycarbonyl, phenylcarbonyloxy, phenylcarbonylamino, phenyl-($C_1$–$C_6$-alkyl)carbonylamino and phenyl-($C_1$–$C_6$-alkyl)carbonyloxy, where the 11 last-mentioned radicals are unsubstituted in the phenyl ring or substituted by one or more radicals from the group consisting of halogen, $C_1$–$C_4$-alkyl, $C_1$–$C_4$-alkoxy, $C_1$–$C_4$-haloalkyl, $C_1$–$C_4$-haloalkoxy, and radicals of the formulae —$SiR'_3$, —O—$SiR'_3$, $(R')_3Si$—$C_1$–$C_6$-alkoxy, —CO—$ONR'_2$, —N=$CR'_2$, —O—$NR'_2$ (—CH(OR')$_2$ and —O—(CH$_2$)$_m$—CH(OR')$_2$, in which the R' in the abovementioned formulae independently of one another are hydrogen, $C_1$–$C_4$-alkyl or phenyl which is unsubstituted or mono- or polysubstituted by radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, or in pairs are a $C_2$–$C_6$-alkylene chain and m=0 to 6, and a substituted alkoxy radical of the formula R"O—CHR'"CH(OR)—$C_1$–$C_6$-alkoxy, in which the R" independently of one another are $C_1$–$C_4$-alkyl or together are a $C_1$–$C_6$-alkylene group and R'" is hydrogen or $C_1$–$C_4$-alkyl.

Important and interesting are also compositions which comprise a compound C3 where in the formula C3 $R^2$ is hydrogen, $C_1$–$C_4$-alkyl, $C_1$–$C_4$-alkoxy or $C_5$–$C_6$-cycloalkyl and at least one of the radicals $R^3$, $R^4$ is a radical of the formula

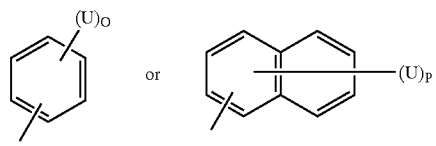

in which (U) represents identical or different radicals which, independently of one another, are hydrogen, halogen, such as fluorine, chlorine, bromine and iodine, cyano, nitro, amino, $C_1$–$C_4$-alkoxy, mono-($C_1$–$C_4$-alkyl)amino, di-($C_1$–$C_4$-alkyl)amino, $C_1$–$C_4$-alkylthio or $C_1$–$C_4$-alkylsulfonyl o is an integer from 1 to 3 and p is an integer from 1 to 3, or one of the radicals $R^3$, $R^4$ independently of one another is a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyridazinyl and quinolinyl which is unsubstituted or substituted by one to three of the abovementioned radicals used.

Extremely interesting are compositions which comprise one or more C3-like compounds of the general formula C3 in which $R^3$, $R^4$ independently of one another are identical or different radicals of the formula

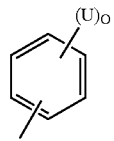

and

R is hydrogen, $C_1$–$C_8$-alkyl, $C_4$–$C_7$-cycloalkyl, $C_2$–$C_8$-alkynyl, heterocyclyl, phenyl or heteroaryl, where each of the seven last-mentioned radicals independently of one another is unsubstituted or substituted by one or more radicals from the group consisting of halogen, cyano, thio, nitro, hydroxyl, $C_1$–$C_4$-alkyl, the latter only in the case of cyclic radicals, $C_1$–$C_4$-haloalkyl, $C_1$–$C_4$-alkoxy, $C_2$–$C_4$-alkenyloxy, $C_2$–$C_4$-alkynyloxy, $C_1$–$C_4$-haloalkoxy, $C_1$–$C_4$-alkylthio, $C_2$–$C_4$-alkenylthio, $C_2$–$C_4$-alkynylthio, $C_5$–$C_6$-cycloalkyl, $C_5$–$C_6$-cycloalkoxy, amino, mono- and di-($C_1$–$C_4$-alkyl)amino, ($C_1$–$C_6$-alkoxy)carbonyl, radicals of the formulae —$SiR'_3$, —O—$NR'_2$, —O—N=$CR'_2$, —N=$CR'_2$, in which the R' in the abovementioned formulae independently of one another are hydrogen, $C_1$–$C_2$-alkyl or phenyl or in pairs are a $C_2$–$C_5$-alkylene chain, and $R^T$ is a radical of the formula —CO—R, —$NR^fR^g$ or —N=$CR^hR^1$.

Special representatives of type C3 which may be mentioned are compounds of the formula C3 in which

| | | | |
|---|---|---|---|
| $R^1$ = —COOCH$_3$ | $R^2$ = H | $R^3$ = $R^4$ = $C_6H_5$ | (C3-1) |
| $R^1$ = —COO-n-$C_3H_7$ | $R^2$ = H | $R^3$ = $R^4$ = $C_6H_5$ | (C3-2) |
| $R^1$ = —COO-n-$C_4H_9$ | $R^2$ = H | $R^3$ = $R^4$ = $C_6H_5$ | (C3-3) |
| $R^1$ = —COO-n-$C_5H_{11}$ | $R^2$ = H | $R^3$ = $R^4$ = $C_6H_5$ | (C3-4) |
| $R^1$ = —COO$^-$Na$^+$ | $R^2$ = H | $R^3$ = $R^4$ = $C_6H_5$ | (C3-5) |
| $R^1$ = —COO—N(CH$_3$)$_4^+$ | $R^2$ = H | $R^3$ = $R^4$ | (C3-6) |
| $R^1$ = —COOCH$_2$CH$_2$Cl | $R^2$ = H | $R^3$ = $R^4$ | (C3-7) |
| $R^1$ = —COOCH$_2$CH$_2$OCH$_3$ | $R^2$ = H | $R^3$ = $R^4$ | (C3-8) |
| $R^1$ = —COOCH$_2$SCH$_3$ | $R^2$ = H | $R^3$ = $R^4$ | (C3-9) |

| | | | |
|---|---|---|---|
| $R^1 = —COOCH_2—CH=CH_2$ | $R^2 = H$ | $R^3 = R^4$ | (C3-10) |
| $R^1 = —COOH$ | $R^2 = H$ | $R^3 = R^4$ | (C3-11) |

$R^5$, $R^6$ together are a $C_2$–$C_4$-alkylene chain or $C_2$–$C_4$-alkenyl chain which is unsubstituted or substituted by one to two radicals from the group consisting of methyl, ethyl, methoxy, ethoxy and halogen.

The safeners (antidotes) of the above groups a) to j) (in particular compounds of the formulae C1, C2 and C3) reduce or neutralize phytotoxic effects which can occur when using the product combinations according to the invention in crops of useful plants, without adversely affecting the activity of the herbicides against harmful plants. Thus, it is possible to increase the area of use of the herbicide mixtures according to the invention considerably. In particular, the use of safeners permits the use of combinations which hitherto could be used only with limitations or without sufficient success, i.e. of combinations which, without safener, at low application rates with a narrow spectrum of activity did not provide sufficient control of the harmful plants.

The herbicidal mixtures according to the invention and said safeners can be applied together (in the form of a finished formulation or by the tank mix method) or in any desired sequence one after the other. The weight ratio safener:herbicide (group A, i.e. compounds of the formula I) can vary within wide limits and is preferably in the range from 1:100 to 100:1, in particular from 1:100 to 50:1. The amounts of herbicides (type A and type B compounds) and safener which are optimal in each case depend on the type of herbicide mixture used and/or on the safener used and on the nature of the plants to be treated.

Depending on their properties, the safeners of type C) can be used for pretreating the seed of the crop plant (seed dressing) or be incorporated into the seed furrows before seeding or used together with the herbicide mixture before or after the plants have emerged. Pre-emergence treatment includes treatment of the area under cultivation before seeding and also treatment of those areas under cultivation which have been seeded but where growth has not yet taken place. Application together with the herbicide mixture is preferred. Tank mixtures or finish formulations can be used for this purpose.

The required application rates of safeners can vary within wide limits, depending on the indication and the herbicide used, and are generally in the range from 0.001 to 1 kg, preferably 0.005 to 0.2 kg, of active compound per hectare.

Particularly favorable herbicidal compositions which are extremely suitable for use in rice are obtained in the context of the invention when herbicides from group Aa) are used in combination with type B compounds and the safener ethyl 5,5-diphenyl-2-isoxazoline-3-carboxylate (=compound C3-1)).

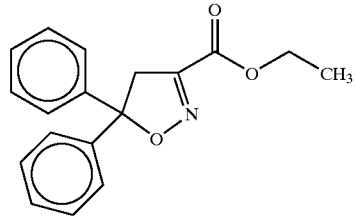

(C3-1)

For this case, it has surprisingly been found that combinations of type A compounds and the safener C3-1) exhibit superadditive, quasi-synergistic activity in rice even without the addition of another standard herbicide from group B. This highly favorable effect permits a further decrease of the application rates, at an unchanged high and broadly effective control. This is preferably true for combinations of compounds of group Aa).

A particularly favorable combination is the joint use of A1) or A1*) and C3-1 with at least one type B compound.

In this case, the safener C3), in particular C3-1, acts particularly advantageously in two ways, both by protecting the rice crops against undesirable damage by the type A herbicides and by the synergistic increase of the activity of the individual herbicides from group A.

Of particular interest for the invention are herbicidal compositions which comprise the type A compounds in an amount of 0.5 to 60 g of ai/ha in combination with the safener C3) in an amount of 10 to 200 g of ai/ha.

Herbicidal compositions which have a weight ratio of type A compounds:C3) in the range from 1:400 to 20:1, preferably 1:200 to 10:1, are likewise favorable.

A particular embodiment of the invention also relates to herbicidal compositions which comprise a type A compound, preferably the compound A1) or A1*), in an amount of 0.1 to 10 g of ai/ha in combination with C3) in an amount of 10–100 g of ai/ha.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are usually not diluted further with additional inert substances prior to use.

The invention also relates to a method for controlling undesirable plants which comprises applying a herbicidally effective amount of a combination of active compounds A+B according to the invention to these plants or to the area under cultivation. The active compounds can be applied to the plants, to parts of plants, plant seeds or to the area under cultivation.

In a preferred variant of the method, the compounds of the formula (I) or salts thereof (type A compounds) are applied at application rates of from 0.1 to 100 g of ai/ha, preferably from 0.5 to 60 g of ai/ha, very particularly preferably between 2 and 40 g of ai/ha, while the application rates for the compounds of type B are from 1 to 5000 g of ai/ha. Preference is given to applying the active compounds of types A and B simultaneously or at different times at a weight ratio of 1:20,000 to 200:1. Furthermore, particular preference is given to the joint application of the active compounds in the form of tank mixtures, the optimally formulated concentrated formulations of the individual active compounds being mixed together in the tank with water and the resulting spray liquor being applied.

Since the combinations according to the invention provide extremely good crop safety and at the same time very efficient control of harmful plants, they can be considered to be selective. In a preferred variation of the method, herbicidal compositions comprising the active compound combinations according to the invention are therefore employed for selective control of undesirable plants.

The method for the selective control of harmful plants using the combination partners of type B) from subgroups Ba) to Bd) is particularly advantageous when the herbicidal compositions of the invention are employed in rice.

The combination partners of type A, applied on their own in rice already control a relatively wide range of annual and perennial broad-leaved weeds, weed grasses and Cyperaceae.

Combination with the type B partners mentioned in the invention improves the activity spectrum of the type A compounds even further.

Thus, the compounds B1) to B27) from group Ba) complement and enhance, inter alia, the activity in the control of grass weeds in rice.

Most of the combination partners B28) to B33) from the group Bb) belong to the growth-regulating herbicides which complement and enhance the activity of the type A compounds in rice, in particular when controlling weeds from the spectrum of the dicotyledonous plants, but also considerably against cyperaceae.

The compounds from the subgroup Bc) (for example B39) to B42)) are widely used active compounds which can be employed for increasing the activity of the type A compounds when controlling mainly cyperaceae especially in rice.

The azoles and pyrazoles from the subgroup Bd) (for example B46) and B47)) can be used particularly advantageously at comparatively low application rates for controlling dicotyledonous weeds in rice. However, they are also particularly effective against a broad spectrum of harmful grasses, just as they control cyperaceae.

A comparable spectrum of harmful plants is controlled by the compounds from the group of the sulfonylureas (compounds B57) to B65)), but the application rates are lower by about another order of magnitude.

Depending on the nature of the combination partner B, the herbicidal combinations according to the invention can be used advantageously for controlling undesirable plants even in transgenic rice crops.

Transgenic crops are those in which the plants have been made resistant to herbicides or pesticides by genetic manipulation. Such modified rice crop plants then allow a selective use.

Overall, the invention thus also relates to the use of herbicidal compositions comprising
A) at least one herbicidally active compound from the group of the substituted phenylsulfonylureas of the formula I and their agriculturally accepted, i.e. acceptable and compatible, salts

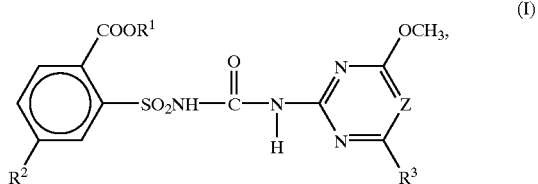
(I)

in which
R$^1$ is (C$_1$–C$_8$)-alkyl, (C$_3$–C$_4$)-alkenyl, (C$_3$–C$_4$)-alkynyl or (C$_1$–C$_4$)-alkyl, which is mono- to tetrasubstituted by radicals from the group consisting of halogen and/or (C$_1$–C$_2$)-alkoxy;
R$^2$ is I or CH$_2$NHSO$_2$CH$_3$;
R$^3$ is methyl or methoxy; and
Z is N or CH;
and
B) at least one herbicidally active compound from the group of the compounds consisting of
Ba) herbicides which are selective in rice, mainly against grasses, selected from the group consisting of B1)butachlor, B2)butenachlor, B3)thenylchlor, B4)pretilachlor, B5)mefenacet, B5a)Bay FOE 5043, B6)naproanilid, B7)propanil, B8)etobenzanid, B9)dimepiperate, B10)molinate, B11)thiobencarb, B12) pyributicarb, B13)quinclorac, B14a)sulcotrione, B15) cycloxydim, B16)sethoxydim, B17)NBA 061 fentrazamid, B18)piperophos, B19)anilofos, B20) fenoxaprop, fenoxaprop-P, B21)haloxyfop, B22) cyhalofop, B23)JC-940, B24)dithiopyr, B25) bromobutide, B26)cinmethylin and B27)CH-900,
Bb) herbicides which are selective in rice, mainly against dicotyledonous harmful plants and cyperaceae, selected from the group consisting of B28)2,4-D, B29)mecoprop, mecoprop-P, B30)MCPA, B31)dicamba, B32)acifluorfen, B33a)

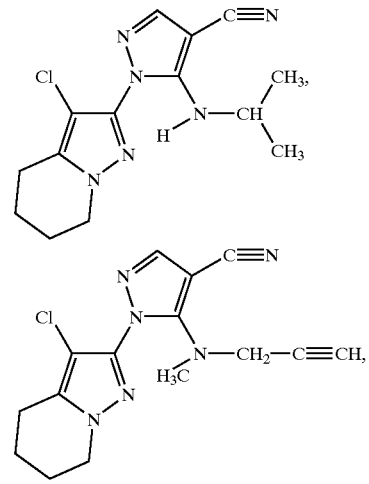
B33b)

B34)chlorimuron, B35)triasulfuron, B36)ioxynil, B37) picloram and B38)carfentrazon,
Bc) herbicides which are selective in rice, mainly against cyperaceae selected from the group consisting of B39) bentazon, B40)triclopyr, B41)benfuresate and B42) daimuron, and
Bd) herbicides which are selective in rice, mainly against grasses and dicotyledonous harmful plants and harmful cyperaceae plants, selected from the group consisting of B43)pendimethalin, B44)clomazon, B45)benzofenap, B46)pyrazolynate, B47)pyrazoxyfen, B48)KIH 2023, B49)KIH 6127, B50)oxadiazon, B51)oxadiargyl, B52) acetochlor, B53)metolachlor, B54)metosulam, B55) oxyfluorfen B56)dalapon, B57)metsulfuron, B58) bensulfuron, B59)pyrazosulfuron, B60)cinosulfuron, B61)imazosulfuron, B62)AC 322,140 (cyclosulfamuron), B63a)ethoxysulfuron (HOE 095404), B64)azimsulfuron (DPX-A8947), B65)nicosulfuron, B66)prometryn, B67) simetryn, B68)thiazopyr, B69)pyrazophos, B70) pentoxazone, B71)indanofan, B72)LGC 40863 and B73) MY 100, in a weight ratio of compounds of the formula I or salts thereof (type A compounds) and compounds from group B in the range from 1:20,000 to 200:1, preferably 1:8000 to 100:1, particularly preferably 1:4000 to 50:1, for controlling undesirable harmful plants in crops of rice.

A preferred use relates to the use of the combinations which comprise A and B compounds in a synergistically effective amount.

Moreover, preference is given to using mixtures with combinations of A) and Ba) for the selective control of grasses in rice.

Preference is also given to the use of mixtures with combinations of A) and Bb) for the selective control of dicotyledonous plants and cyperaceae in rice.

Preference is likewise given to using mixtures of combinations of A) and Bc) for the selective control of cyperaceae in rice.

It is furthermore advantageous to use mixtures with combinations of A) and Bd) for the selective control of grasses, dicotyledonous plants and cyperaceae in rice.

The invention also embraces, in particular, mixtures having more than one combination partner A) and/or more than one combination partner B).

Specific examples which may be mentioned for the claimed active compound mixtures having more than two active compounds from groups A and B are those below, without thereby imposing a limitation to only those combinations which have been mentioned explicitly:

A1 and/or A1*+B19 (anilofos)+B1 (butachlor);
A1 and/or A1*+B19 (anilofos)+B2 (butenachlor);
A1 and/or A1*+B19 (anilofos)+B3 (thenylchlor);
A1 and/or A1*+B19 (anilofos)+B4 (pretilachlor);
A1 and/or A1*+B19 (anilofos)+B5 (mefenacet);
A1 and/or A1*+B19 (anilofos)+B6 (naproanilid);
A1 and/or A1*+B19 (anilofos)+B7 (propanil);
A1 and/or A1*+B19 (anilofos)+B8 (etobenzanid);
A1 and/or A1*+B19 (anilofos)+B9 (dimepiperate);
A1 and/or A1*+B19 (anilofos)+B10 (molinate);
A1 and/or A1*+B19 (anilofos)+B11 (thiobencarb);
A1 and/or A1*+B19 (anilofos)+B12 (pyributicarb);
A1 and/or A1*+B19 (anilofos)+B13 (quinclorac);
A1 and/or A1*+B19 (anilofos)+B14a (sulcotrione);
A1 and/or A1*+B19 (anilofos)+B17 (Bayer NBA 061);
A1 and/or A1*+B19 (anilofos)+B18 (piperophos);
A1 and/or A1*+B19 (anilofos)+B20 (fenoxaprop and/or fenoxaprop-P);
A1 and/or A1*+B19 (anilofos)+B21 (haloxyfop);
A1 and/or A1*+B19 (anilofos)+B22 (DEH-112);
A1 and/or A1*+B19 (anilofos)+B23 (JC-940);
A1 and/or A1*+B19 (anilofos)+B24 (dithiopyr);
A1 and/or A1*+B19 (anilofos)+B25 (bromobutide);
A1 and/or A1*+B19 (anilofos)+B26 (cinmethylin);
A1 and/or A1*+B19 (anilofos)+B27 (CH-900);
A1 and/or A1*+B19 (anilofos)+B28 (2,4-D);
A1 and/or A1*+B19 (anilofos)+B29 (mecoprop and/or mecoprop-P);
A1 and/or A1*+B19 (anilofos)+B30 (MCPA);
A1 and/or A1*+B19 (anilofos)+B31 (dicamba);
A1 and/or A1*+B19 (anilofos)+B32 (acifluorfen);
A1 and/or A1*+B19 (anilofos)+B33a and/or B33b;
A1 and/or A1*+B19 (anilofos)+B39 (bentazon);
A1 and/or A1*+B19 (anilofos)+B40 (triclopyr);
A1 and/or A1*+B19 (anilofos)+B41 (benfuresate);
A1 and/or A1*+B19 (anilofos)+B42 (daimuron);
A1 and/or A1*+B19 (anilofos)+B43 (pendimethalin);
A1 and/or A1*+B19 (anilofos)+B44 (clomazon);
A1 and/or A1*+B19 (anilofos)+B45 (benzofenap);
A1 and/or A1*+B19 (anilofos)+B46 (pyrazolynate);
A1 and/or A1*+B19 (anilofos)+B47 (pyrazoxyfen);
A1 and/or A1*+B19 (anilofos)+B48 (KIH 2023);
A1 and/or A1*+B19 (anilofos)+B57 (metsulfuron);
A1 and/or A1*+B19 (anilofos)+B58 (bensulfuron);
A1 and/or A1*+B19 (anilofos)+B59 (pyrazosulfuron);
A1 and/or A1*+B19 (anilofos)+B60 (cinosulfuron);
A1 and/or A1*+B19 (anilofos)+B61 (imazosulfuron);
A1 and/or A1*+B19 (anilofos)+B62 (AC 322,140 (cyclosulfamuron));
A1 and/or A1*+B19 (anilofos)+B63a (ethoxysulfuron (HOE 095404));
A1 and/or A1*+B19 (anilofos)+B64 (azimsulfuron (DPX-A8947));
A1 and/or A1*+B19 (anilofos)+B65 (nicosulfuron);
A2 and/or A3+B19 (anilofos)+B1 (butachlor);
A2 and/or A3+B19 (anilofos)+B2 (butenachlor);
A2 and/or A3+B19 (anilofos)+B3 (thenylchlor);
A2 and/or A3+B19 (anilofos)+B4 (pretilachlor);
A2 and/or A3+B19 (anilofos)+B5 (mefenacet);
A2 and/or A3+B19 (anilofos)+B6 (naproanilid);
A2 and/or A3+B19 (anilofos)+B7 (propanil);
A2 and/or A3+B19 (anilofos)+B8 (etobenzanid);
A2 and/or A3+B19 (anilofos)+B9 (dimepiperate);
A2 and/or A3+B19 (anilofos)+B10 (molinate);
A2 and/or A3+B19 (anilofos)+B11 (thiobencarb);
A2 and/or A3+B19 (anilofos)+B12 (pyributicarb);
A2 and/or A3+B19 (anilofos)+B13 (quinclorac);
A2 and/or A3+B19 (anilofos)+B14a (sulcotrione);
A2 and/or A3+B19 (anilofos)+B17 (Bayer NBA 061);
A2 and/or A3+B19 (anilofos)+B18 (piperophos);
A2 and/or A3+B19 (anilofos)+B20 (fenoxaprop and/or fenoxaprop-P);
A2 and/or A3+B19 (anilofos)+B21 (haloxyfop);
A2 and/or A3+B19 (anilofos)+B22 (DEH-112);
A2 and/or A3+B19 (anilofos)+B23 (JC-940);
A2 and/or A3+B19 (anilofos)+B24 (dithiopyr);
A2 and/or A3+B19 (anilofos)+B25 (bromobutide);
A2 and/or A3+B19 (anilofos)+B26 (cinmethylin);
A2 and/or A3+B19 (anilofos)+B27 (CH-900);
A2 and/or A3+B19 (anilofos)+B28 (2,4-D);
A2 and/or A3+B19 (anilofos)+B29 (mecoprop and/or mecoprop-P);
A2 and/or A3+B19 (anilofos)+B30 (MCPA);
A2 and/or A3+B19 (anilofos)+B31 (dicamba);
A2 and/or A3+B19 (anilofos)+B32 (acifluorfen);
A2 and/or A3+B19 (anilofos)+B33a and/or B33b;
A2 and/or A3+B19 (anilofos)+B39 (bentazon);
A2 and/or A3+B19 (anilofos)+B40 (triclopyr);
A2 and/or A3+B19 (anilofos)+B41 (benfuresate);
A2 and/or A3+B19 (anilofos)+B42 (daimuron);
A2 and/or A3+B19 (anilofos)+B43 (pendimethalin);
A2 and/or A3+B19 (anilofos)+B44 (clomazon);
A2 and/or A3+B19 (anilofos)+B45 (benzofenap);
A2 and/or A3+B19 (anilofos)+B46 (pyrazolynate);
A2 and/or A3+B19 (anilofos)+B47 (pyrazoxyfen);
A2 and/or A3+B19 (anilofos)+B48 (KIH 2023);
A2 and/or A3+B19 (anilofos)+B57 (metsulfuron);
A2 and/or A3+B19 (anilofos)+B58 (bensulfuron);
A2 and/or A3+B19 (anilofos)+B59 (pyrazosulfuron);
A2 and/or A3+B19 (anilofos)+B60 (cinosulfuron);
A2 and/or A3+B19 (anilofos)+B61 (imazosulfuron);
A2 and/or A3+B19 (anilofos)+B62 (AC 322,140 (cyclosulfamuron));
A2 and/or A3+B19 (anilofos)+B63a (ethoxysulfuron (HOE 095404));

A2 and/or A3+B19 (anilofos)+B64 (azimsulfuron (DPX-A8947));
A2 and/or A3+B19 (anilofos)+B65 (nicosulfuron);
A1 and/or A1* and/or A2 and/or A3+B63a (ethoxysulfuron)+B1 (butachlor);
A1 and/or A1* and/or A2 and/or A3+B63a (ethoxysulfuron)+B2 (butenachlor);
A1 and/or A1* and/or A2 and/or A3+B63a (ethoxysulfuron)+B3 (thenylchlor);
A1 and/or A1* and/or A2 and/or A3+B63a (ethoxysulfuron)+B4 (pretilachlor);
A1 and/or A1* and/or A2 and/or A3+B63a (ethoxysulfuron)+B5 (mefenacet);
A1 and/or A1* and/or A2 and/or A3+B63a (ethoxysulfuron)+B6 (naproanilid);
A1 and/or A1* and/or A2 and/or A3+B63a (ethoxysulfuron)+B7 (propanil);
A1 and/or A1* and/or A2 and/or A3+B63a (ethoxysulfuron)+B8 (etobenzanid);
A1 and/or A1* and/or A2 and/or A3+B63a (ethoxysulfuron)+B9 (dimepiperate);
A1 and/or A1* and/or A2 and/or A3+B63a (ethoxysulfuron)+B10 (molinate);
A1 and/or A1* and/or A2 and/or A3+B63a (ethoxysulfuron)+B11 (thiobencarb);
A1 and/or A1* and/or A2 and/or A3+B63a (ethoxysulfuron)+B12 (pyributicarb);
A1 and/or A1* and/or A2 and/or A3+B63a (ethoxysulfuron)+B13 (quinclorac);
A1 and/or A1* and/or A2 and/or A3+B63a (ethoxysulfuron)+B14a (sulcotrione);
A1 and/or A1* and/or A2 and/or A3+B63a (ethoxysulfuron)+B17 (Bayer NBA 061);
A1 and/or A1* and/or A2 and/or A3+B63a (ethoxysulfuron)+B18 (piperophos);
A1 and/or A1* and/or A2 and/or A3+B63a (ethoxysulfuron)+B20 (fenoxaprop and/or fenoxaprop-P);
A1 and/or A1* and/or A2 and/or A3+B63a (ethoxysulfuron)+B21 (haloxyfop);
A1 and/or A1* and/or A2 and/or A3+B63a (ethoxysulfuron)+B22 (DEH-112);
A1 and/or A1* and/or A2 and/or A3+B63a (ethoxysulfuron)+B23 (JC-940);
A1 and/or A1* and/or A2 and/or A3+B63a (ethoxysulfuron)+B24 (dithiopyr);
A1 and/or A1* and/or A2 and/or A3+B63a (ethoxysulfuron)+B25 (bromobutide);
A1 and/or A1* and/or A2 and/or A3+B63a (ethoxysulfuron)+B26 (cinmethylin);
A1 and/or A1* and/or A2 and/or A3+B63a (ethoxysulfuron)+B27 (CH-900);
A1 and/or A1* and/or A2 and/or A3+B63a (ethoxysulfuron)+B28 (2,4-D);
A1 and/or A1* and/or A2 and/or A3+B63a (ethoxysulfuron)+B29 (mecoprop and/or mecoprop-P);
A1 and/or A1* and/or A2 and/or A3+B63a (ethoxysulfuron)+B30 (MCPA);
A1 and/or A1* and/or A2 and/or A3+B63a (ethoxysulfuron)+B31 (dicamba);
A1 and/or A1* and/or A2 and/or A3+B63a (ethoxysulfuron)+B32 (acifluorfen);
A1 and/or A1* and/or A2 and/or A3+B63a (ethoxysulfuron)+B33a and/or B33b;
A1 and/or A1* and/or A2 and/or A3+B63a (ethoxysulfuron)+B39 (bentazon);
A1 and/or A1* and/or A2 and/or A3+B63a (ethoxysulfuron)+B40 (triclopyr);
A1 and/or A1* and/or A2 and/or A3+B63a (ethoxysulfuron)+B41 (benfuresate);
A1 and/or A1* and/or A2 and/or A3+B63a (ethoxysulfuron)+B42 (daimuron);
A1 and/or A1* and/or A2 and/or A3+B63a (ethoxysulfuron)+B43 (pendimethalin);
A1 and/or A1* and/or A2 and/or A3+B63a (ethoxysulfuron)+B44 (clomazon);
A1 and/or A1* and/or A2 and/or A3+B63a (ethoxysulfuron)+B45 (benzofenap);
A1 and/or A1* and/or A2 and/or A3+B63a (ethoxysulfuron)+B46 (pyrazolynate);
A1 and/or A1* and/or A2 and/or A3+B63a (ethoxysulfuron)+B47 (pyrazoxyfen);
A1 and/or A1* and/or A2 and/or A3+B63a (ethoxysulfuron)+B48 (KIH 2023);
A1 and/or A1* and/or A2 and/or A3+B63a (ethoxysulfuron)+B57 (metsulfuron);
A1 and/or A1* and/or A2 and/or A3+B63a (ethoxysulfuron)+B58 (bensulfuron);
A1 and/or A1* and/or A2 and/or A3+B63a (ethoxysulfuron)+B59 (pyrazosulfuron);
A1 and/or A1* and/or A2 and/or A3+B63a (ethoxysulfuron)+B60 (cinosulfuron);
A1 and/or A1* and/or A2 and/or A3+B63a (ethoxysulfuron)+B61 (imazosulfuron);
A1 and/or A1* and/or A2 and/or A3+B63a (ethoxysulfuron)+B62 (AC 322,140 (cyclosulfamuron));
A1 and/or A1* and/or A2 and/or A3+B63a (ethoxysulfuron)+B64 (azimsulfuron (DPX-A8947));
A1 and/or A1* and/or A2 and/or A3+B63a (ethoxysulfuron)+B65 (nicosulfuron);
A1 and/or A1* and/or A2 and/or A3+B20 (fenoxaprop and/or fenoxaprop-P)+B1 (butachlor);
A1 and/or A1* and/or A2 and/or A3+B20 (fenoxaprop and/or fenoxaprop-P)+B2 (butenachlor);
A1 and/or A1* and/or A2 and/or A3+B20 (fenoxaprop and/or fenoxaprop-P)+B3 (thenylchlor);
A1 and/or A1* and/or A2 and/or A3+B20 (fenoxaprop and/or fenoxaprop-P)+B4 (pretilachlor);
A1 and/or A1* and/or A2 and/or A3+B20 (fenoxaprop and/or fenoxaprop-P)+B5 (mefenacet);
A1 and/or A1* and/or A2 and/or A3+B20 (fenoxaprop and/or fenoxaprop-P)+B6 (naproanilid);
A1 and/or A1* and/or A2 and/or A3+B20 (fenoxaprop and/or fenoxaprop-P)+B7 (propanil);
A1 and/or A1* and/or A2 and/or A3+B20 (fenoxaprop and/or fenoxaprop-P)+B8 (etobenzanid);
A1 and/or A1* and/or A2 and/or A3+B20 (fenoxaprop and/or fenoxaprop-P)+B9 (dimepiperate);
A1 and/or A1* and/or A2 and/or A3+B20 (fenoxaprop and/or fenoxaprop-P)+B10 (molinate);
A1 and/or A1* and/or A2 and/or A3+B20 (fenoxaprop and/or fenoxaprop-P)+B11 (thiobencarb);
A1 and/or A1* and/or A2 and/or A3+B20 (fenoxaprop and/or fenoxaprop-P)+B12 (pyributicarb);
A1 and/or A1* and/or A2 and/or A3+B20 (fenoxaprop and/or fenoxaprop-P)+B13 (quinclorac);
A1 and/or A1* and/or A2 and/or A3+B20 (fenoxaprop and/or fenoxaprop-P)+B14a (sulcotrione);
A1 and/or A1* and/or A2 and/or A3+B20 (fenoxaprop and/or fenoxaprop-P)+B17 (Bayer NBA 061);
A1 and/or A1* and/or A2 and/or A3+B20 (fenoxaprop and/or fenoxaprop-P)+B18 (piperophos);
A1 and/or A1* and/or A2 and/or A3+B20 (fenoxaprop and/or fenoxaprop-P)+B21 (haloxyfop);
A1 and/or A1* and/or A2 and/or A3+B20 (fenoxaprop and/or fenoxaprop-P)+B22 (DEH-112);

A1 and/or A1* and/or A2 and/or A3+B20 (fenoxaprop and/or fenoxaprop-P)+B23 (JC-940);
A1 and/or A1* and/or A2 and/or A3+B20 (fenoxaprop and/or fenoxaprop-P)+B24 (dithiopyr);
A1 and/or A1* and/or A2 and/or A3+B20 (fenoxaprop and/or fenoxaprop-P)+B25 (bromobutide);
A1 and/or A1* and/or A2 and/or A3+B20 (fenoxaprop and/or fenoxaprop-P)+B26 (cinmethylin);
A1 and/or A1* and/or A2 and/or A3+B20 (fenoxaprop and/or fenoxaprop-P)+B27 (CH-900);
A1 and/or A1* and/or A2 and/or A3+B20 (fenoxaprop and/or fenoxaprop-P)+B28 (2,4-D);
A1 and/or A1* and/or A2 and/or A3+B20 (fenoxaprop and/or fenoxaprop-P)+B29 (mecoprop and/or mecoprop-P);
A1 and/or A1* and/or A2 and/or A3+B20 (fenoxaprop and/or fenoxaprop-P)+B30 (MCPA);
A1 and/or A1* and/or A2 and/or A3+B20 (fenoxaprop and/or fenoxaprop-P)+B31 (dicamba);
A1 and/or A1* and/or A2 and/or A3+B20 t(fenoxaprop and/or fenoxaprop-P)+B32 (acifluorfen);
A1 and/or A1* and/or A2 and/or A3+B20 (fenoxaprop and/or fenoxaprop-P)+B33a and/or B33b;
A1 and/or A1* and/or A2 and/or A3+B20 (fenoxaprop and/or fenoxaprop-P)+B39 (bentazon);
A1 and/or A1* and/or A2 and/or A3+B20 (fenoxaprop and/or fenoxaprop-P)+B40 (triclopyr);
A1 and/or A1* and/or A2 and/or A3+B20 (fenoxaprop and/or fenoxaprop-P)+B41 (benfuresate);
A1 and/or A1* and/or A2 and/or A3+B20 (fenoxaprop and/or fenoxaprop-P)+B42 (daimuron);
A1 and/or A1* and/or A2 and/or A3+B20 (fenoxaprop and/or fenoxaprop-P)+B43 (pendimethalin);
A1 and/or A1* and/or A2 and/or A3+B20 (fenoxaprop and/or fenoxaprop-P)+B44 (clomazon);
A1 and/or A1* and/or A2 and/or A3+B20 (fenoxaprop and/or fenoxaprop-P)+B45 (benzofenap);
A1 and/or A1* and/or A2 and/or A3+B20 (fenoxaprop and/or fenoxaprop-P)+B46 (pyrazolynate);
A1 and/or A1* and/or A2 and/or A3+B20 (fenoxaprop and/or fenoxaprop-P)+B47 (pyrazoxyfen);
A1 and/or A1* and/or A2 and/or A3+B20 (fenoxaprop and/or fenoxaprop-P)+B48 (KIH 2023);
A1 and/or A1* and/or A2 and/or A3+B20 (fenoxaprop and/or fenoxaprop-P)+B57 (metsulfuron);
A1 and/or A1* and/or A2 and/or A3+B20 (fenoxaprop and/or fenoxaprop-P)+B58 (bensulfuron);
A1 and/or A1* and/or A2 and/or A3+B20 (fenoxaprop and/or fenoxaprop-P)+B59 (pyrazosulfuron);
A1 and/or A1* and/or A2 and/or A3+B20 (fenoxaprop and/or fenoxaprop-P)+B60 (cinosulfuron);
A1 and/or A1* and/or A2 and/or A3+B20 (fenoxaprop and/or fenoxaprop-P)+B61 (imazosulfuron);
A1 and/or A1* and/or A2 and/or A3+B20 (fenoxaprop and/or fenoxaprop-P)+B62 (AC 322,140 (cyclosulfamuron));
A1 and/or A1* and/or A2 and/or A3+B20 (fenoxaprop and/or fenoxaprop-P)+B64 (azimsulfuron (DPX-A8947));
A1 and/or A1* and/or A2 and/or A3+B20 (fenoxaprop and/or fenoxaprop-P)+B65 (nicosulfuron);

The mixtures with more than two components described above can advantageously be employed together with one or more safeners. An example of a preferred safener is 1-methylhexyl (5-chloroquinolin-8-yloxy)acetate (C2-1); this gives, for example, the following mixtures:

A1 and/or A1* and/or A2 and/or A3+B19 (anilofos)+B1 (butachlor)+(C2-1);
A1 and/or A1* and/or A2 and/or A3+B19 (anilofos)+B2 (butenachlor)+(C2-1);
A1 and/or A1* and/or A2 and/or A3+B19 (anilofos)+B3 (thenylchlor)+(C2-1);
A1 and/or A1* and/or A2 and/or A3+B19 (anilofos)+B4 (pretilachlor)+(C2-1);
A1 and/or A1* and/or A2 and/or A3+B19 (anilofos)+B5 (mefenacet)+(C2-1);
A1 and/or A1* and/or A2 and/or A3+B19 (anilofos)+B6 (naproanilid)+(C2-1);
A1 and/or A1* and/or A2 and/or A3+B19 (anilofos)+B7 (propanil)+(C2-1);
A1 and/or A1* and/or A2 and/or A3+B19 (anilofos)+B8 (etobenzanid)+(C2-1);
A1 and/or A1* and/or A2 and/or A3+B19 (anilofos)+B9 (dimepiperate)+(C2-1);
A1 and/or A1* and/or A2 and/or A3+B19 (anilofos)+B10 (molinate)+(C2-1);
A1 and/or A1* and/or A2 and/or A3+B19 (anilofos)+B11 (thiobencarb)+(C2-1);
A1 and/or A1* and/or A2 and/or A3+B19 (anilofos)+B12 (pyributicarb)+(C2-1);
A1 and/or A1* and/or A2 and/or A3+B19 (anilofos)+B13 (quinclorac)+(C2-1);
A1 and/or A1* and/or A2 and/or A3+B19 (anilofos)+B14a (sulcotrione)+(C2-1);
A1 and/or A1* and/or A2 and/or A3+B19 (anilofos)+B17 (Bayer NBA 061)+(C2-1);
A1 and/or A1* and/or A2 and/or A3+B19 (anilofos)+B18 (piperophos)+(C2-1);
A1 and/or A1* and/or A2 and/or A3+B19 (anilofos)+B20 (fenoxaprop and/or fenoxaprop-P)+(C2-1);
A1 and/or A1* and/or A2 and/or A3+B19 (anilofos)+B21 (haloxyfop)+(C2-1);
A1 and/or A1* and/or A2 and/or A3+B19 (anilofos)+B22 (DEH-112)+(C2-1);
A1 and/or A1* and/or A2 and/or A3+B19 (anilofos)+B23 (JC-940)+(C2-1);
A1 and/or A1* and/or A2 and/or A3+B19 (anilofos)+B24 (dithiopyr)+(C2-1);
A1 and/or A1* and/or A2 and/or A3+B19 (anilofos)+B25 (bromobutide)+(C2-1);
A1 and/or A1* and/or A2 and/or A3+B19 (anilofos)+B26 (cinmethylin)+(C2-1);
A1 and/or A1* and/or A2 and/or A3+B19 (anilofos)+B27 (CH-900)+(C2-1);
A1 and/or A1* and/or A2 and/or A3+B19 (anilofos)+B28 (2,4-D)+(C2-1)
A1 and/or A1* and/or A2 and/or A3+B19 (anilofos)+B29 (mecoprop and/or mecoprop-P)+(C2-1);
A1 and/or A1* and/or A2 and/or A3+B19 (anilofos)+B30 (MCPA)+(C2-1);
A1 and/or A1* and/or A2 and/or A3+B19 (anilofos)+B31 (dicamba)+(C2-1);
A1 and/or A1* and/or A2 and/or A3+B19 (anilofos)+B32 (acifluorfen)+(C2-1);
A1 and/or A1* and/or A2 and/or A3+B19 (anilofos)+B33a and/or B33b +(C2-1);
A1 and/or A1* and/or A2 and/or A3+B19 (anilofos)+B39 (bentazon)+(C2-1);
A1 and/or A1* and/or A2 and/or A3+B19 (anilofos)+B40 (triclopyr)+(C2-1);
A1 and/or A1* and/or A2 and/or A3+B19 (anilofos)+B41 (benfuresate)+(C2-1);
A1 and/or A1* and/or A2 and/or A3+B19 (anilofos)+B42 (daimuron)+(C2-1);
A1 and/or A1* and/or A2 and/or A3+B19 (anilofos)+B43 (pendimethalin)+(C2-1);

A1 and/or A1* and/or A2 and/or A3+B19 (anilofos)+B44 (clomazon)+(C2-1);
A1 and/or A1* and/or A2 and/or A3+B19 (anilofos)+B45 (benzofenap)+(C2-1);
A1 and/or A1* and/or A2 and/or A3+B19 (anilofos)+B46 (pyrazolynate)+(C2-1);
A1 and/or A1* and/or A2 and/or A3+B19 (anilofos)+B47 (pyrazoxyfen)+(C2-1);
A1 and/or A1* and/or A2 and/or A3+B19 (anilofos)+B48 (KIH 2023)+(C2-1);
A1 and/or A1* and/or A2 and/or A3+B19 (anilofos)+B57 (metsulfuron)+(C2-1);
A1 and/or A1* and/or A2 and/or A3+B19 (anilofos)+B58 (bensulfuron)+(C2-1);
A1 and/or A1* and/or A2 and/or A3+B19 (anilofos)+B59 (pyrazosulfuron)+(C2-1);
A1 and/or A1* and/or A2 and/or A3+B19 (anilofos)+B60 (cinosulfuron)+(C2-1);
A1 and/or A1* and/or A2 and/or A3+B19 (anilofos)+B61 (imazosulfuron)+(C2-1);
A1 and/or A1* and/or A2 and/or A3+B19 (anilofos)+B62 (AC 322,140 (cyclosulfamuron))+(C2-1);
A1 and/or A1* and/or A2 and/or A3+B19 (anilofos)+B63a (ethoxysulfuron (HOE 095404))+(C2-1);
A1 and/or A1* and/or A2 and/or A3+B19 (anilofos)+B64 (azimsulfuron (DPX-A8947))+(C2-1);
A1 and/or A1* and/or A2 and/or A3+B19 (anilofos)+B65 (nicosulfuron)+(C2-1);
A1 and/or A1* and/or A2 and/or A3+B63a (ethoxysulfuron)+B1 (butachlor)+(C2-1);
A1 and/or A1* and/or A2 and/or A3+B63a (ethoxysulfuron)+B2 (butenachlor)+(C2-1);
A1 and/or A1* and/or A2 and/or A3+B63a (ethoxysulfuron)+B3 (thenylchlor)+(C2-1);
A1 and/or A1* and/or A2 and/or A3+B63a (ethoxysulfuron)+B4 (pretilachlor)+(C2-1);
A1 and/or A1* and/or A2 and/or A3+B63a (ethoxysulfuron)+B5 (mefenacet)+(C2-1);
A1 and/or A1* and/or A2 and/or A3+B63a (ethoxysulfuron)+B6 (naproanilid)+(C2-1);
A1 and/or A1* and/or A2 and/or A3+B63a (ethoxysulfuron)+B7 (propanil)+(C2-1);
A1 and/or A1* and/or A2 and/or A3+B63a (ethoxysulfuron)+B8 (etobenzanid)+(C2-1);
A1 and/or A1* and/or A2 and/or A3+B63a (ethoxysulfuron)+B9 (dimepiperate)+(C2-1);
A1 and/or A1* and/or A2 and/or A3+B63a (ethoxysulfuron)+B10 (molinate)+(C2-1);
A1 and/or A1* and/or A2 and/or A3+B63a (ethoxysulfuron)+B11 (thiobencarb)+(C2-1);
A1 and/or A1* and/or A2 and/or A3+B63a (ethoxysulfuron)+B12 (pyributicarb)+(C2-1);
A1 and/or A1* and/or A2 and/or A3+B63a (ethoxysulfuron)+B13 (quinclorac)+(C2-1);
A1 and/or A1* and/or A2 and/or A3+B63a (ethoxysulfuron)+B14a (sulcotrione)+(C2-1);
A1 and/or A1* and/or A2 and/or A3+B63a (ethoxysulfuron)+B17 (Bayer NBA 061)+(C2-1);
A1 and/or A1* and/or A2 and/or A3+B63a (ethoxysulfuron)+B18 (piperophos)+(C2-1);
A1 and/or A1* and/or A2 and/or A3+B63a (ethoxysulfuron)+B20 (fenoxaprop and/or fenoxaprop-P)+(C2-1);
A1 and/or A1* and/or A2 and/or A3+B63a (ethoxysulfuron)+B21 (haloxyfop)+(C2-1);
A1 and/or A1* and/or A2 and/or A3+B63a (ethoxysulfuron)+B22 (DEH-112)+(C2-1);
A1 and/or A1* and/or A2 and/or A3+B63a (ethoxysulfuron)+B23 (JC-940)+(C2-1);
A1 and/or A1* and/or A2 and/or A3+B63a (ethoxysulfuron)+B24 (dithiopyr)+(C2-1);
A1 and/or A1* and/or A2 and/or A3+B63a (ethoxysulfuron)+B25 (bromobutide)+(C2-1);
A1 and/or A1* and/or A2 and/or A3+B63a (ethoxysulfuron)+B26 (cinmethylin)+(C2-1);
A1 and/or A1* and/or A2 and/or A3+B63a (ethoxysulfuron)+B27 (CH-900)+(C2-1);
A1 and/or A1* and/or A2 and/or A3+B63a (ethoxysulfuron)+B28 (2,4-D)+(C2-1);
A1 and/or A1* and/or A2 and/or A3+B63a (ethoxysulfuron)+B29 (mecoprop and/or mecoprop-P)+(C2-1);
A1 and/or A1* and/or A2 and/or A3+B63a (ethoxysulfuron)+B30 (MCPA)+(C2-1);
A1 and/or A1* and/or A2 and/or A3+B63a (ethoxysulfuron)+B31 (dicamba)+(C2-1);
A1 and/or A1* and/or A2 and/or A3+B63a (ethoxysulfuron)+B32 (acifluorfen)+(C2-1);
A1 and/or A1* and/or A2 and/or A3+B63a (ethoxysulfuron)+B33a and/or B33b+(C2-1);
A1 and/or A1* and/or A2 and/or A3+B63a (ethoxysulfuron)+B39 (bentazon)+(C2-1);
A1 and/or A1* and/or A2 and/or A3+B63a (ethoxysulfuron)+B40 (triclopyr)+(C2-1);
A1 and/or A1* and/or A2 and/or A3+B63a (ethoxysulfuron)+B41 (benfuresate)+(C2-1);
A1 and/or A1* and/or A2 and/or A3+B63a (ethoxysulfuron)+B42 (daimuron)+(C2-1);
A1 and/or A1* and/or A2 and/or A3+B63a (ethoxysulfuron)+B43 (pendimethalin)+(C2-1);
A1 and/or A1* and/or A2 and/or A3+B63a (ethoxysulfuron)+B44 (clomazon)+(C2-1);
A1 and/or A1* and/or A2 and/or A3+B63a (ethoxysulfuron)+B45 (benzofenap)+(C2-1);
A1 and/or A1* and/or A2 and/or A3+B63a (ethoxysulfuron)+B46 (pyrazolynate)+(C2-1);
A1 and/or A1* and/or A2 and/or A3+B63a (ethoxysulfuron)+B47 (pyrazoxyfen)+(C2-1);
A1 and/or A1* and/or A2 and/or A3+B63a (ethoxysulfuron)+B48 (KIH 2023)+(C2-1);
A1 and/or A1* and/or A2 and/or A3+B63a (ethoxysulfuron)+B57 (metsulfuron)+(C2-1);
A1 and/or A1* and/or A2 and/or A3+B63a (ethoxysulfuron)+B58 (bensulfuron)+(C2-1);
A1 and/or A1* and/or A2 and/or A3+B63a (ethoxysulfuron)+B59 (pyrazosulfuron)+(C2-1);
A1 and/or A1* and/or A2 and/or A3+B63a (ethoxysulfuron)+B60 (cinosulfuron)+(C2-1);
A1 and/or A1* and/or A2 and/or A3+B63a (ethoxysulfuron)+B61 (imazosulfuron)+(C2-1);
A1 and/or A1* and/or A2 and/or A3+B63a (ethoxysulfuron)+B62 (AC 322,140 (cyclosulfamuron))+(C2-1);
A1 and/or A1* and/or A2 and/or A3+B63a (ethoxysulfuron)+B64 (azimsulfuron (DPX-A8947))+(C2-1);
A1 and/or A1* and/or A2 and/or A3+B63a (ethoxysulfuron)+B65 (nicosulfuron)+(C2-1);
A1 and/or A1* and/or A2 and/or A3+B20 (fenoxaprop and/or fenoxaprop-P)+B1 (butachlor)+(C2-1);
A1 and/or A1* and/or A2 and/or A3+B20 (fenoxaprop and/or fenoxaprop-P)+B2 (butenachlor)+(C2-1);
A1 and/or A1* and/or A2 and/or A3+B20 (fenoxaprop and/or fenoxaprop-P)+B3 (thenylchlor)+(C2-1);

A1 and/or A1* and/or A2 and/or A3+B20 (fenoxaprop and/or fenoxaprop-P)+B4 (pretilachlor)+(C2-1);
A1 and/or A1* and/or A2 and/or A3+B20 (fenoxaprop and/or fenoxaprop-P)+B5 (mefenacet)+(C2-1);
A1 and/or A1* and/or A2 and/or A3+B20 (fenoxaprop and/or fenoxaprop-P)+B6 (naproanilid)+(C2-1);
A1 and/or A1* and/or A2 and/or A3+B20 (fenoxaprop and/or fenoxaprop-P)+B7 (propanil)+(C2-1);
A1 and/or A1* and/or A2 and/or A3+B20 (fenoxaprop and/or fenoxaprop-P)+B8 (etobenzanid)+(C2-1);
A1 and/or A1* and/or A2 and/or A3+B20 (fenoxaprop and/or fenoxaprop-P)+B9 (dimepiperate)+(C2-1);
A1 and/or A1* and/or A2 and/or A3+B20 (fenoxaprop and/or fenoxaprop-P)+B10 (molinate)+(C2-1);
A1 and/or A1* and/or A2 and/or A3+B20 (fenoxaprop and/or fenoxaprop-P)+B11 (thiobencarb)+(C2-1);
A1 and/or A1* and/or A2 and/or A3+B20 (fenoxaprop and/or fenoxaprop-P)+B12 (pyributicarb)+(C2-1);
A1 and/or A1* and/or A2 and/or A3+B20 (fenoxaprop and/or fenoxaprop-P)+B13 (quinclorac)+(C2-1);
A1 and/or A1* and/or A2 and/or A3+B20 (fenoxaprop and/or fenoxaprop-P)+B14a (sulcotrione)+(C2-1);
A1 and/or A1* and/or A2 and/or A3+B20 (fenoxaprop and/or fenoxaprop-P)+B17 (Bayer NBA 061)+(C2-1);
A1 and/or A1* and/or A2 and/or A3+B20 (fenoxaprop and/or fenoxaprop-P)+B18 (piperophos)+(C2-1);
A1 and/or A1* and/or A2 and/or A3+B20 (fenoxaprop and/or fenoxaprop-P)+B21 (haloxyfop)+(C2-1);
A1 and/or A1* and/or A2 and/or A3+B20 (fenoxaprop and/or fenoxaprop-P)+B22 (DEH-112)+(C2-1);
A1 and/or A1* and/or A2 and/or A3+B20 (fenoxaprop and/or fenoxaprop-P)+B23 (JC-940)+(C2-1);
A1 and/or A1* and/or A2 and/or A3+B20 (fenoxaprop and/or fenoxaprop-P)+B24 (dithiopyr)+(C2-1);
A1 and/or A1* and/or A2 and/or A3+B20 (fenoxaprop and/or fenoxaprop-P)+B25 (bromobutide)+(C2-1);
A1 and/or A1* and/or A2 and/or A3+B20 (fenoxaprop and/or fenoxaprop-P)+B26 (cinmethylin)+(C2-1);
A1 and/or A1* and/or A2 and/or A3+B20 (fenoxaprop and/or fenoxaprop-P)+B27 (CH-900)+(C2-1);
A1 and/or A1* and/or A2 and/or A3+B20 (fenoxaprop and/or fenoxaprop-P)+B28 (2,4-D)+(C2-1);
A1 and/or A1* and/or A2 and/or A3+B20 (fenoxaprop and/or fenoxaprop-P)+B29 (mecoprop and/or mecoprop-P)+(C2-1);
A1 and/or A1* and/or A2 and/or A3+B20 (fenoxaprop and/or fenoxaprop-P)+B30 (MCPA)+(C2-1);
A1 and/or A1* and/or A2 and/or A3+B20 (fenoxaprop and/or fenoxaprop-P)+B31 (dicamba)+(C2-1);
A1 and/or A1* and/or A2 and/or A3+B20 (fenoxaprop and/or fenoxaprop-P)+B32 (acifluorfen)+(C2-1);
A1 and/or A1* and/or A2 and/or A3+B20 (fenoxaprop and/or fenoxaprop-P)+B33a and/or B33b+(C2-1);
A1 and/or A1* and/or A2 and/or A3+B20 (fenoxaprop and/or fenoxaprop-P)+B39 (bentazon)+(C2-1);
A1 and/or A1* and/or A2 and/or A3+B20 (fenoxaprop and/or fenoxaprop-P)+B40 (triclopyr)+(C2-1);
A1 and/or A1* and/or A2 and/or A3+B20 (fenoxaprop and/or fenoxaprop-P)+B41 (benfuresate)+(C2-1);
A1 and/or A1* and/or A2 and/or A3+B20 (fenoxaprop and/or fenoxaprop-P)+B42 (daimuron)+(C2-1);
A1 and/or A1* and/or A2 and/or A3+B20 (fenoxaprop and/or fenoxaprop-P)+B43 (pendimethalin)+(C2-1);
A1 and/or A1* and/or A2 and/or A3+B20 (fenoxaprop and/or fenoxaprop-P)+B44 (clomazon)+(C2-1);
A1 and/or A1* and/or A2 and/or A3+B20 (fenoxaprop and/or fenoxaprop-P)+B45 (benzofenap)+(C2-1);
A1 and/or A1* and/or A2 and/or A3+B20 (fenoxaprop and/or fenoxaprop-P)+B46 (pyrazolynate)+(C2-1);
A1 and/or A1* and/or A2 and/or A3+B20 (fenoxaprop and/or fenoxaprop-P)+B47 (pyrazoxyfen)+(C2-1);
A1 and/or A1* and/or A2 and/or A3+B20 (fenoxaprop and/or fenoxaprop-P)+B48 (KIH 2023)+(C2-1);
A1 and/or A1* and/or A2 and/or A3+B20 (fenoxaprop and/or fenoxaprop-P)+B57 (metsulfuron)+(C2-1);
A1 and/or A1* and/or A2 and/or A3+B20 (fenoxaprop and/or fenoxaprop-P)+B58 (bensulfuron)+(C2-1);
A1 and/or A1* and/or A2 and/or A3+B20 (fenoxaprop and/or fenoxaprop-P)+B59 (pyrazosulfuron)+(C2-1);
A1 and/or A1* and/or A2 and/or A3+B20 (fenoxaprop and/or fenoxaprop-P)+B60 (cinosulfuron)+(C2-1);
A1 and/or A1* and/or A2 and/or A3+B20 (fenoxaprop and/or fenoxaprop-P)+B61 (imazosulfuron)+(C2-1);
A1 and/or A1* and/or A2 and/or A3+B20 (fenoxaprop and/or fenoxaprop-P)+B62 (AC 322,140 (cyclosulfamuron))+(C2-1);
A1 and/or A1* and/or A2 and/or A3+B20 (fenoxaprop and/or fenoxaprop-P)+B64 (azimsulfuron (DPX-A8947))+(C2-1);
A1 and/or A1* and/or A2 and/or A3+B20 (fenoxaprop and/or fenoxaprop-P)+B65 (nicosulfuron)+(C2-1);

Most preference is also given to mixtures of the safener (C3-1):

A1 and/or A1* and/or A2 and/or A3+B19 (anilofos)+B1 (butachlor)+(C3-1);
A1 and/or A1* and/or A2 and/or A3+B19 (anilofos)+B2 (butenachlor)+(C3-1);
A1 and/or A1* and/or A2 and/or A3+B19 (anilofos)+B3 (thenylchlor)+(C3-1);
A1 and/or A1* and/or A2 and/or A3+B19 (anilofos)+B4 (pretilachlor)+(C3-1);
A1 and/or A1* and/or A2 and/or A3+B19 (anilofos)+B5 (mefenacet)+(C3-1);
A1 and/or A1* and/or A2 and/or A3+B19 (anilofos)+B6 (naproanilid)+(C3-1);
A1 and/or A1* and/or A2 and/or A3+B19 (anilofos)+B7 (propanil)+(C3-1);
A1 and/or A1* and/or A2 and/or A3+B19 (anilofos)+B8 (etobenzanid)+(C3-1);
A1 and/or A1* and/or A2 and/or A3+B19 (anilofos)+B9 (dimepiperate)+(C3-1);
A1 and/or A1* and/or A2 and/or A3+B19 (anilofos)+B10 (molinate)+(C3-1);
A1 and/or A1* and/or A2 and/or A3+B19 (anilofos)+B11 (thiobencarb)+(C3-1);
A1 and/or A1* and/or A2 and/or A3+B19 (anilofos)+B12 (pyributicarb)+(C3-1);
A1 and/or A1* and/or A2 and/or A3+B19 (anilofos)+B13 (quinclorac)+(C3-1);
A1 and/or A1* and/or A2 and/or A3+B19 (anilofos)+B14a (sulcotrione)+(C3-1);
A1 and/or A1* and/or A2 and/or A3+B19 (anilofos)+B17 (Bayer NBA 061)+(C3-1);
A1 and/or A1* and/or A2 and/or A3+B19 (anilofos)+B18 (piperophos)+(C3-1);
A1 and/or A1* and/or A2 and/or A3+B19 (anilofos)+B20 (fenoxaprop and/or fenoxaprop-P)+(C3-1);
A1 and/or A1* and/or A2 and/or A3+B19 (anilofos)+B21 (haloxyfop)+(C3-1);
A1 and/or A1* and/or A2 and/or A3+B19 (anilofos)+B22 (DEH-112)+(C3-1);
A1 and/or A1* and/or A2 and/or A3+B19 (anilofos)+B23 (JC-940)+(C3-1);
A1 and/or A1* and/or A2 and/or A3+B19 (anilofos)+B24 (dithiopyr)+(C3-1);

A1 and/or A1* and/or A2 and/or A3+B19 (anilofos)+B25 (bromobutide)+(C3-1);
A1 and/or A1* and/or A2 and/or A3+B19 (anilofos)+B26 (cinmethylin)+(C3-1);
A1 and/or A1* and/or A2 and/or A3+B19 (anilofos)+B27 (CH-900)+(C3-1);
A1 and/or A1* and/or A2 and/or A3+B19 (anilofos)+B28 (2,4-D)+(C3-1);
A1 and/or A1* and/or A2 and/or A3+B19 (anilofos)+B29 (mecoprop and/or mecoprop-P)+(C3-1);
A1 and/or A1* and/or A2 and/or A3+B19 (anilofos)+B30 (MCPA)+(C3-1);
A1 and/or A1* and/or A2 and/or A3+B19 (anilofos)+B31 (dicamba)+(C3-1);
A1 and/or A1* and/or A2 and/or A3+B19 (anilofos)+B32 (acifluorfen)+(C3-1);
A1 and/or A1* and/or A2 and/or A3+B19 (anilofos)+B33a and/or B33b +(C3-1);
A1 and/or A1* and/or A2 and/or A3+B19 (anilofos)+B39 (bentazon)+(C3-1);
A1 and/or A1* and/or A2 and/or A3+B19 (anilofos)+B40 (triclopyr)+(C3-1);
A1 and/or A1* and/or A2 and/or A3+B19 (anilofos)+B41 (benfuresate)+(C3-1);
A1 and/or A1* and/or A2 and/or A3+B19 (anilofos)+B42 (daimuron)+(C3-1);
A1 and/or A1* and/or A2 and/or A3+B19 (anilofos)+B43 (pendimethalin)+(C3-1);
A1 and/or A1* and/or A2 and/or A3+B19 (anilofos)+B44 (clomazon)+(C3-1);
A1 and/or A1* and/or A2 and/or A3+B19 (anilofos)+B45 (benzofenap)+(C3-1);
A1 and/or A1* and/or A2 and/or A3+B19 (anilofos)+B46 (pyrazolynate)+(C3-1);
A1 and/or A1* and/or A2 and/or A3+B19 (anilofos)+B47 (pyrazoxyfen)+(C3-1);
A1 and/or A1* and/or A2 and/or A3+B19 (anilofos)+B48 (KIH 2023)+(C3-1);
A1 and/or A1* and/or A2 and/or A3+B19 (anilofos)+B57 (metsulfuron)+(C3-1);
A1 and/or A1* and/or A2 and/or A3+B19 (anilofos)+B58 (bensulfuron)+(C3-1);
A1 and/or A1* and/or A2 and/or A3+B19 (anilofos)+B59 (pyrazosulfuron)+(C3-1);
A1 and/or A1* and/or A2 and/or A3+B19 (anilofos)+B60 (cinosulfuron)+(C3-1);
A1 and/or A1* and/or A2 and/or A3+B19 (anilofos)+B61 (imazosulfuron)+(C3-1);
A1 and/or A1* and/or A2 and/or A3+B19 (anilofos)+B62 (AC 322,140 (cyclosulfamuron))+(C3-1);
A1 and/or A1* and/or A2 and/or A3+B19 (anilofos)+B63a (ethoxysulfuron (HOE 095404))+(C3-1);
A1 and/or A1* and/or A2 and/or A3+B19 (anilofos)+B64 (azimsulfuron (DPX-A8947))+(C3-1);
A1 and/or A1* and/or A2 and/or A3+B19 (anilofos)+B65 (Nicosulfuron)+(C3-1);
A1 and/or A1* and/or A2 and/or A3+B63a (ethoxysulfuron)+B1 (butachlor)+(C3-1);
A1 and/or A1* and/or A2 and/or A3+B63a (ethoxysulfuron)+B2 (butenachlor)+(C3-1);
A1 and/or A1* and/or A2 and/or A3+B63a (ethoxysulfuron)+B3 (thenylchlor)+(C3-1);
A1 and/or A1* and/or A2 and/or A3+B63a (ethoxysulfuron)+B4 (pretilachlor)+(C3-1);
A1 and/or A1* and/or A2 and/or A3+B63a (ethoxysulfuron)+B5 (mefenacet)+(C3-1);
A1 and/or A1* and/or A2 and/or A3+B63a (ethoxysulfuron)+B6 (naproanilid)+(C3-1);
A1 and/or A1* and/or A2 and/or A3+B63a (ethoxysulfuron)+B7 (propanil)+(C3-1);
A1 and/or A1* and/or A2 and/or A3+B63a (ethoxysulfuron)+B8 (etobenzanid)+(C3-1);
A1 and/or A1* and/or A2 and/or A3+B63a (ethoxysulfuron)+B9 (dimepiperate)+(C3-1);
A1 and/or A1* and/or A2 and/or A3+B63a (ethoxysulfuron)+B10 (molinate)+(C3-1);
A1 and/or A1* and/or A2 and/or A3+B63a (ethoxysulfuron)+B11 (thiobencarb)+(C3-1);
A1 and/or A1* and/or A2 and/or A3+B63a (ethoxysulfuron)+B12 (pyributicarb)+(C3-1);
A1 and/or A1* and/or A2 and/or A3+B63a (ethoxysulfuron)+B13 (quinclorac)+(C3-1);
A1 and/or A1* and/or A2 and/or A3+B63a (ethoxysulfuron)+B14a (sulcotrione)+(C3-1);
A1 and/or A1* and/or A2 and/or A3+B63a (ethoxysulfuron)+B17 (Bayer NBA 061)+(C3-1);
A1 and/or A1* and/or A2 and/or A3+B63a (ethoxysulfuron)+B18 (piperophos)+(C3-1);
A1 and/or A1* and/or A2 and/or A3+B63a (ethoxysulfuron)+B20 (fenoxaprop and/or fenoxaprop-P)+(C3-1);
A1 and/or A1* and/or A2 and/or A3+B63a (ethoxysulfuron)+B21 (haloxyfop)+(C3-1);
A1 and/or A1* and/or A2 and/or A3+B63a (ethoxysulfuron)+B22 (DEH-112)+(C3-1);
A1 and/or A1* and/or A2 and/or A3+B63a (ethoxysulfuron)+B23 (JC-940)+(C3-1);
A1 and/or A1* and/or A2 and/or A3+B63a (ethoxysulfuron)+B24 (dithiopyr)+(C3-1);
A1 and/or A1* and/or A2 and/or A3+B63a (ethoxysulfuron)+B25 (bromobutide)+(C3-1);
A1 and/or A1* and/or A2 and/or A3+B63a (ethoxysulfuron)+B26 (cinmethylin)+(C3-1);
A1 and/or A1* and/or A2 and/or A3+B63a (ethoxysulfuron)+B27 (CH-900)+(C3-1);
A1 and/or A1* and/or A2 and/or A3+B63a (ethoxysulfuron)+B28 (2,4-D)+(C3-1);
A1 and/or A1* and/or A2 and/or A3+B63a (ethoxysulfuron)+B29 (mecoprop and/or mecoprop-P)+(C3-1);
A1 and/or A1* and/or A2 and/or A3+B63a (ethoxysulfuron)+B30 (MCPA)+(C3-1);
A1 and/or A1* and/or A2 and/or A3+B63a (ethoxysulfuron)+B31 (dicamba)+(C3-1);
A1 and/or A1* and/or A2 and/or A3+B63a (ethoxysulfuron)+B32 (acifluorfen)+(C3-1);
A1 and/or A1* and/or A2 and/or A3+B63a (ethoxysulfuron)+B33a and/or B33b+(C3-1);
A1 and/or A1* and/or A2 and/or A3+B63a (ethoxysulfuron)+B39 (bentazon)+(C3-1);
A1 and/or A1* and/or A2 and/or A3+B63a (ethoxysulfuron)+B40 (triclopyr)+(C3-1);
A1 and/or A1* and/or A2 and/or A3+B63a (ethoxysulfuron)+B41 (benfuresate)+(C3-1);
A1 and/or A1* and/or A2 and/or A3+B63a (ethoxysulfuron)+B42 (daimuron)+(C3-1);
A1 and/or A1* and/or A2 and/or A3+B63a (ethoxysulfuron)+B43 (pendimethalin)+(C3-1);
A1 and/or A1* and/or A2 and/or A3+B63a (ethoxysulfuron)+B44 (clomazon)+(C3-1);
A1 and/or A1* and/or A2 and/or A3+B63a (ethoxysulfuron)+B45 (benzofenap)+(C3-1);
A1 and/or A1* and/or A2 and/or A3+B63a (ethoxysulfuron)+B46 (pyrazolynate)+(C3-1);
A1 and/or A1* and/or A2 and/or A3+B63a (ethoxysulfuron)+B47 (pyrazoxyfen)+(C3-1);

A1 and/or A1* and/or A2 and/or A3+B63a (ethoxysulfuron)+B48 (KIH 2023)+(C3-1);
A1 and/or A1* and/or A2 and/or A3+B63a (ethoxysulfuron)+B57 (metsulfuron)+(C3-1);
A1 and/or A1* and/or A2 and/or A3+B63a (ethoxysulfuron)+B58 (bensulfuron)+(C3-1);
A1 and/or A1* and/or A2 and/or A3+B63a (ethoxysulfuron)+B59 (pyrazosulfuron)+(C3-1);
A1 and/or A1* and/or A2 and/or A3+B63a (ethoxysulfuron)+B60 (cinosulfuron)+(C3-1);
A1 and/or A1* and/or A2 and/or A3+B63a (ethoxysulfuron)+B61 (imazosulfuron)+(C3-1);
A1 and/or A1* and/or A2 and/or A3+B63a (ethoxysulfuron)+B62 (AC 322,140 (cyclosulfamuron))+(C3-1);
A1 and/or A1* and/or A2 and/or A3+B63a (ethoxysulfuron)+B64 (azimsulfuron (DPX-A8947))+(C3-1);
A1 and/or A1* and/or A2 and/or A3+B63a (ethoxysulfuron)+B65 (nicosulfuron)+(C3-1);
A1 and/or A1* and/or A2 and/or A3+B20 (fenoxaprop and/or fenoxaprop-P)+B1 (butachlor)+(C3-1);
A1 and/or A1* and/or A2 and/or A3+B20 (fenoxaprop and/or fenoxaprop-P)+B2 (butenachlor)+(C3-1);
A1 and/or A1* and/or A2 and/or A3+B20 (fenoxaprop and/or fenoxaprop-P)+B3 (thenylchlor)+(C3-1);
A1 and/or A1* and/or A2 and/or A3+B20 (fenoxaprop and/or fenoxaprop-P)+B4 (pretilachlor)+(C3-1);
A1 and/or A1* and/or A2 and/or A3+B20 (fenoxaprop and/or fenoxaprop-P)+B5 (mefenacet)+(C3-1);
A1 and/or A1* and/or A2 and/or A3+B20 (fenoxaprop and/or fenoxaprop-P)+B6 (naproanilid)+(C3-1);
A1 and/or A1* and/or A2 and/or A3+B20 (fenoxaprop and/or fenoxaprop-P)+B7 (propanil)+(C3-1);
A1 and/or A1* and/or A2 and/or A3+B20 (fenoxaprop and/or fenoxaprop-P)+B8 (etobenzanid)+(C3-1);
A1 and/or A1* and/or A2 and/or A3+B20 (fenoxaprop and/or fenoxaprop-P)+B9 (dimepiperate)+(C3-1);
A1 and/or A1* and/or A2 and/or A3+B20 (fenoxaprop and/or fenoxaprop-P)+B10 (molinate)+(C3-1);
A1 and/or A1* and/or A2 and/or A3+B20 (fenoxaprop and/or fenoxaprop-P)+B11 (thiobencarb)+(C3-1);
A1 and/or A1* and/or A2 and/or A3+B20 (fenoxaprop and/or fenoxaprop-P)+B12 (pyributicarb)+(C3-1);
A1 and/or A1* and/or A2 and/or A3+B20 (fenoxaprop and/or fenoxaprop-P)+B13 (quinclorac)+(C3-1);
A1 and/or A1* and/or A2 and/or A3+B20 (fenoxaprop and/or fenoxaprop-P)+B14a (sulcotrione)+(C3-1);
A1 and/or A1* and/or A2 and/or A3+B20 (fenoxaprop and/or fenoxaprop-P)+B17 (Bayer NBA 061)+(C3-1);
A1 and/or A1* and/or A2 and/or A3+B20 (fenoxaprop and/or fenoxaprop-P)+B18 (piperophos)+(C3-1);
A1 and/or A1* and/or A2 and/or A3+B20 (fenoxaprop and/or fenoxaprop-P)+B21 (haloxyfop)+(C3-1);
A1 and/or A1* and/or A2 and/or A3+B20 (fenoxaprop and/or fenoxaprop-P)+B22 (DEH-112)+(C3-1);
A1 and/or A1* and/or A2 and/or A3+B20 (fenoxaprop and/or fenoxaprop-P)+B23 (JC-940)+(C3-1);
A1 and/or A1* and/or A2 and/or A3+B20 (fenoxaprop and/or fenoxaprop-P)+B24 (dithiopyr)+(C3-1);
A1 and/or A1* and/or A2 and/or A3+B20 (fenoxaprop and/or fenoxaprop-P)+B25 (bromobutide)+(C3-1);
A1 and/or A1* and/or A2 and/or A3+B20 (fenoxaprop and/or fenoxaprop-P)+B26 (cinmethylin)+(C3-1);
A1 and/or A1* and/or A2 and/or A3+B20 (fenoxaprop and/or fenoxaprop-P)+B27 (CH-900)+(C3-1);
A1 and/or A1* and/or A2 and/or A3+B20 (fenoxaprop and/or fenoxaprop-P)+B28 (2,4-D)+(C3-1);
A1 and/or A1* and/or A2 and/or A3+B20 (fenoxaprop and/or fenoxaprop-P)+B29 (mecoprop and/or mecoprop-P)+(C3-1);
A1 and/or A1* and/or A2 and/or A3+B20 (fenoxaprop and/or fenoxaprop-P)+B30 (MCPA)+(C3-l);
A1 and/or A1* and/or A2 and/or A3+B20 (fenoxaprop and/or fenoxaprop-P)+B31 (dicamba)+(C3-1);
A1 and/or A1* and/or A2 and/or A3+B20 (fenoxaprop and/or fenoxaprop-P)+B32 (acifluorfen)+(C3-1);
A1 and/or A1* and/or A2 and/or A3+B20 (fenoxaprop and/or fenoxaprop-P)+B33a and/or B33b +(C3-1);
A1 and/or A1* and/or A2 and/or A3+B20 (fenoxaprop and/or fenoxaprop-P)+B39 (bentazon)+(C3-1);
A1 and/or A1* and/or A2 and/or A3+B20 (fenoxaprop and/or fenoxaprop-P)+B40 (triclopyr)+(C3-1);
A1 and/or A1* and/or A2 and/or A3+B20 (fenoxaprop and/or fenoxaprop-P)+B41 (benfuresate)+(C3-1);
A1 and/or A1* and/or A2 and/or A3+B20 (fenoxaprop and/or fenoxaprop-P)+B42 (daimuron)+(C3-1);
A1 and/or A1* and/or A2 and/or A3+B20 (fenoxaprop and/or fenoxaprop-P)+B43 (pendimethalin)+(C3-1);
A1 and/or A1* and/or A2 and/or A3+B20 (fenoxaprop and/or fenoxaprop-P)+B44 (clomazon)+(C3-l);
A1 and/or A1* and/or A2 and/or A3+B20 (fenoxaprop and/or fenoxaprop-P)+B45 (benzofenap)+(C3-1);
A1 and/or A1* and/or A2 and/or A3+B20 (fenoxaprop and/or fenoxaprop-P)+B46 (pyrazolynate)+(C3-1);
A1 and/or A1* and/or A2 and/or A3+B20 (fenoxaprop and/or fenoxaprop-P)+B47 (pyrazoxyfen)+(C3-1);
A1 and/or A1* and/or A2 and/or A3+B20 (fenoxaprop and/or fenoxaprop-P)+B48 (KIH 2023)+(C3-1);
A1 and/or A1* and/or A2 and/or A3+B20 (fenoxaprop and/or fenoxaprop-P)+B57 (metsulfuron)+(C3-1);
A1 and/or A1* and/or A2 and/or A3+B20 (fenoxaprop and/or fenoxaprop-P)+B58 (bensulfuron)+(C3-1);
A1 and/or A1* and/or A2 and/or A3+B20 (fenoxaprop and/or fenoxaprop-P)+B59 (pyrazosulfuron)+(C3-1);
A1 and/or A1* and/or A2 and/or A3+B20 (fenoxaprop and/or fenoxaprop-P)+B60 (cinosulfuron)+(C3-1);
A1 and/or A1* and/or A2 and/or A3+B20 (fenoxaprop and/or fenoxaprop-P)+B61 (imazosulfuron)+(C3-1);
A1 and/or A1* and/or A2 and/or A3+B20 (fenoxaprop and/or fenoxaprop-P)+B62 (AC 322,140 (cyclosulfamuron))+(C3-1);
A1 and/or A1* and/or A2 and/or A3+B20 (fenoxaprop and/or fenoxaprop-P)+B64 (azimsulfuron (DPX-A8947))+(C3-1);
A1 and/or A1* and/or A2 and/or A3+B20 (fenoxaprop and/or fenoxaprop-P)+B65 (nicosulfuron)+(C3-1);

The use of a safener in the abovementioned combinations offers considerable advantages, since it reduces possible damage to the crop plant rice which may be caused by sulfonylurea derivatives or other herbicidally active compounds.

The abovementioned active compound combinations can easily be varied.

On the one hand, the compounds of the formulae A1 and/or A1 *, A2 or A3 can be replaced by other compounds of the formula I, without the resulting combinations being considerably worse. Rather, the substance mixture present is still essentially synergistically active.

On the other hand, it is likewise possible to replace the sulfonylurea B63a (ethoxysulfuron) in the listed combinations by one or more of the following sulfonylureas:
B57) metsulfuron;
B58) bensulfuron;
B59) pyrazosulfuron;

B60) cinosulfuron;
B61) imazosulfuron;
B62) cyclosulfamuron;
B64) azimsulfuron;
B65) nicosulfuron.

Particularly preferred multicomponent combinations comprise two or more of the sulfonylureas of type B. These include, inter alia:

A1 and/or A1* and/or A2 and/or A3+B34 (chlorimuron)+B35 (triasulfuron);
A1 and/or A1* and/or A2 and/or A3+B34 (chlorimuron)+B57 (metsulfuron);
A1 and/or A1* and/or A2 and/or A3+B34 (chlorimuron)+B58 (bensulfuron);
A1 and/or A1* and/or A2 and/or A3+B34 (chlorimuron)+B59 (pyrazosulfuron);
A1 and/or A1* and/or A2 and/or A3+B34 (chlorimuron)+B60 (cinosulfuron);
A1 and/or A1* and/or A2 and/or A3+B34 (chlorimuron)+B61 (imazosulfuron);
A1 and/or A1* and/or A2 and/or A3+B34 (chlorimuron)+B62 (AC 322,140 (cyclosulfamuron));
A1 and/or A1* and/or A2 and/or A3+B34 (chlorimuron)+B64 (azimsulfuron (DPX-A8947));
A1 and/or A1* and/or A2 and/or A3+B34 (chlorimuron)+B65 (nicosulfuron);
A1 and/or A1* and/or A2 and/or A3+B34 (chlorimuron)+B35 (triasulfuron)+(C3-1);
A1 and/or A1* and/or A2 and/or A3+B34 (chlorimuron)+B57 (metsulfuron)+(C3-1);
A1 and/or A1* and/or A2 and/or A3+B34 (chlorimuron)+B58 (bensulfuron)+(C3-1);
A1 and/or A1* and/or A2 and/or A3+B34 (chlorimuron)+B59 (pyrazosulfuron)+(C3-1);
A1 and/or A1* and/or A2 and/or A3+B34 (chlorimuron)+B60 (cinosulfuron)+(C3-l);
A1 and/or A1* and/or A2 and/or A3+B34 (chlorimuron)+B61 (imazosulfuron)+(C3-1);
A1 and/or A1* and/or A2 and/or A3+B34 (chlorimuron)+B62 (AC 322,140 (cyclosulfamuron))+(C3-1);
A1 and/or A1* and/or A2 and/or A3+B34 (chlorimuron)+B64 (azimsulfuron (DPX-A8947))+(C3-1);
A1 and/or A1* and/or A2 and/or A3+B34 (chlorimuron)+B65 (nicosulfuron)+(C3-1);
A1 and/or A1* and/or A2 and/or A3+B35 (triasulfuron)+B57 (metsulfuron);
A1 and/or A1* and/or A2 and/or A3+B35 (triasulfuron)+B58 (bensulfuron);
A1 and/or A1* and/or A2 and/or A3+B35 (triasulfuron)+B59 (pyrazosulfuron);
A1 and/or A1* and/or A2 and/or A3+B35 (triasulfuron)+B60 (cinosulfuron);
A1 and/or A1* and/or A2 and/or A3+B35 (triasulfuron)+B61 (imazosulfuron);
A1 and/or A1* and/or A2 and/or A3+B35 (triasulfuron)+B62 (AC 322,140 (cyclosulfamuron));
A1 and/or A1* and/or A2 and/or A3+B35 (triasulfuron)+B64 (azimsulfuron (DPX-A8947));
A1 and/or A1* and/or A2 and/or A3+B35 (triasulfuron)+B65 (nicosulfuron);
A1 and/or A1* and/or A2 and/or A3+B35 (triasulfuron)+B57 (metsulfuron)+(C3-1);
A1 and/or A1* and/or A2 and/or A3+B35 (triasulfuron)+B58 (bensulfuron)+(C3-1);
A1 and/or A1* and/or A2 and/or A3+B35 (triasulfuron)+B59 (pyrazosulfuron)+(C3-1);
A1 and/or A1* and/or A2 and/or A3+B35 (triasulfuron)+B60 (cinosulfuron)+(C3-1);
A1 and/or A1* and/or A2 and/or A3+B35 (triasulfuron)+B61 (imazosulfuron)+(C3-1);
A1 and/or A1* and/or A2 and/or A3+B35 (triasulfuron)+B62 (AC 322,140 (cyclosulfamuron))+(C3-1);
A1 and/or A1* and/or A2 and/or A3+B35 (triasulfuron)+B64 (azimsulfuron (DPX-A8947))+(C3-1);
A1 and/or A1* and/or A2 and/or A3+B35 (triasulfuron)+B65 (nicosulfuron)+(C3-1);
A1 and/or A1* and/or A2 and/or A3+B57 (metsulfuron)+B58 (bensulfuron);
A1 and/or A1* and/or A2 and/or A3+B57 (metsulfuron)+B59 (pyrazosulfuron);
A1 and/or A1* and/or A2 and/or A3+B57 (metsulfuron)+B60 (cinosulfuron);
A1 and/or A1* and/or A2 and/or A3+B57 (metsulfuron)+B61 (imazosulfuron);
A1 and/or A1* and/or A2 and/or A3+B57 (metsulfuron)+B62 (AC 322,140 (cyclosulfamuron));
A1 and/or A1* and/or A2 and/or A3+B57 (metsulfuron)+B64 (azimsulfuron (DPX-A8947));
A1 and/or A1* and/or A2 and/or A3+B57 (metsulfuron)+B65 (nicosulfuron);
A1 and/or A1* and/or A2 and/or A3+B57 (metsulfuron)+B58 (bensulfuron)+(C3-1);
A1 and/or A1* and/or A2 and/or A3+B57 (metsulfuron)+B59 (pyrazosulfuron)+(C3-1);
A1 and/or A1* and/or A2 and/or A3+B57 (metsulfuron)+B60 (cinosulfuron)+(C3-1);
A1 and/or A1* and/or A2 and/or A3+B57 (metsulfuron)+B61 (imazosulfuron)+(C3-1);
A1 and/or A1* and/or A2 and/or A3+B57 (metsulfuron)+B62 (AC 322,140 (cyclosulfamuron))+(C3-1);
A1 and/or A1* and/or A2 and/or A3+B57 (metsulfuron)+B64 (azimsulfuron (DPX-A8947))+(C3-1);
A1 and/or A1* and/or A2 and/or A3+B57 (metsulfuron)+B65 (nicosulfuron)+(C3-1);
A1 and/or A1* and/or A2 and/or A3+B58 (bensulfuron)+B59 (pyrazosulfuron);
A1 and/or A1* and/or A2 and/or A3+B58 (bensulfuron)+B60 (cinosulfuron);
A1 and/or A1* and/or A2 and/or A3+B58 (bensulfuron)+B61 (imazosulfuron);
A1 and/or A1* and/or A2 and/or A3+B58 (bensulfuron)+B62 (AC 322,140 (cyclosulfamuron));
A1 and/or A1* and/or A2 and/or A3+B58 (bensulfuron)+B64 (azimsulfuron (DPX-A8947));
A1 and/or A1* and/or A2 and/or A3+B58 (bensulfuron)+B65 (nicosulfuron);
A1 and/or A1* and/or A2 and/or A3+B58 (bensulfuron)+B59 (pyrazosulfuron)+(C3-1);
A1 and/or A1* and/or A2 and/or A3+B58 (bensulfuron)+B60 (cinosulfuron)+(C3-1);
A1 and/or A1* and/or A2 and/or A3+B58 (bensulfuron)+B61 (imazosulfuron)+(C3-1);
A1 and/or A1* and/or A2 and/or A3+B58 (bensulfuron)+B62 (AC 322,140 (cyclosulfamuron))+(C3-1);
A1 and/or A1* and/or A2 and/or A3+B58 (bensulfuron)+B64 (azimsulfuron (DPX-A8947))+(C3-1);
A1 and/or A1* and/or A2 and/or A3+B58 (bensulfuron)+B65 (nicosulfuron)+(C3-1);
A1 and/or A1* and/or A2 and/or A3+B59 (pyrazosulfuron)+B60 (cinosulfuron);
A1 and/or A1* and/or A2 and/or A3+B59 (pyrazosulfuron)+B61 (imazosulfuron);
A1 and/or A1* and/or A2 and/or A3+B59 (pyrazosulfuron)+B62 (AC 322,140 (cyclosulfamuron));
A1 and/or A1* and/or A2 and/or A3+B59 (pyrazosulfuron)+B64 (azimsulfuron (DPX-A8947));

A1 and/or A1* and/or A2 and/or A3+B59 (pyrazosulfuron)+B65 (nicosulfuron);
A1 and/or A1* and/or A2 and/or A3+B59 (pyrazosulfuron)+B60 (cinosulfuron)+(C3-1);
A1 and/or A1* and/or A2 and/or A3+B59 (pyrazosulfuron)+B61 (imazosulfuron)+(C3-1);
A1 and/or A1* and/or A2 and/or A3+B59 (pyrazosulfuron)+B62 (AC 322,140 (cyclosulfamuron))+(C3-1);
A1 and/or A1* and/or A2 and/or A3+B59 (pyrazosulfuron)+B64 (Azimsulfuron (DPX-A8947))+(C3-1);
A1 and/or A1* and/or A2 and/or A3+B59 (pyrazosulfuron)+B65 (nicosulfuron)+(C3-1);
A1 and/or A1* and/or A2 and/or A3+B60 (cinosulfuron)+B61 (imazosulfuron);
A1 and/or A1* and/or A2 and/or A3+B60 (cinosulfuron)+B62 (AC 322,140 (cyclosulfamuron));
A1 and/or A1* and/or A2 and/or A3+B60 (cinosulfuron)+B64 (azimsulfuron (DPX-A8947));
A1 and/or A1* and/or A2 and/or A3+B60 (cinosulfuron)+B65 (nicosulfuron);
A1 and/or A1* and/or A2 and/or A3+B60 (cinosulfuron)+B61 (imazosulfuron)+(C3-1);
A1 and/or A1* and/or A2 and/or A3+B60 (cinosulfuron)+B62 (AC 322,140 (cyclosulfamuron))+(C3-1);
A1 and/or A1* and/or A2 and/or A3+B60 (cinosulfuron)+B64 (azimsulfuron (DPX-A8947))+(C3-1);
A1 and/or A1* and/or A2 and/or A3+B60 (cinosulfuron)+B65 (nicosulfuron)+(C3-1);
A1 and/or A1* and/or A2 and/or A3+B61 (imazosulfuron)+B62 (AC 322,140 (cyclosulfamuron));
A1 and/or A1* and/or A2 and/or A3+B61 (imazosulfuron)+B64 (azimsulfuron (DPX-A8947));
A1 and/or A1* and/or A2 and/or A3+B61 (imazosulfuron)+B65 (nicosulfuron);
A1 and/or A1* and/or A2 and/or A3+B61 (imazosulfuron)+B62 (AC 322,140 (cyclosulfamuron))+(C3-1);
A1 and/or A1* and/or A2 and/or A3+B61 (imazosulfuron)+B64 (azimsulfuron (DPX-A8947))+(C3-1);
A1 and/or A1* and/or A2 and/or A3+B61 (imazosulfuron)+B65 (nicosulfuron)+(C3-1);
A1 and/or A1* and/or A2 and/or A3+B62 (cyclosulfamuron)+B64 (azimsulfuron (DPX-A8947));
A1 and/or A1* and/or A2 and/or A3+B62 (cyclosulfamuron)+B65 (nicosulfuron);
A1 and/or A1* and/or A2 and/or A3+B62 (cyclosulfamuron)+B64 (azimsulfuron (DPX-A8947))+(C3-1);
A1 and/or A1* and/or A2 and/or A3+B62 (cyclosulfamuron)+B65 (nicosulfuron)+(C3-1);
A1 and/or A1* and/or A2 and/or A3+B64 (azimsulfuron)+B65 (nicosulfuron);
A1 and/or A1* and/or A2 and/or A3+B64 (azimsulfuron)+B65 (nicosulfuron)+(C3-1);

Also of particular interest for the invention are mixtures of one or more type A compounds with at least two group B compounds, where at least one of the type B compounds is a sulfonylurea compound and at least one of the type B compounds is a grass herbicide. These mixtures include, for example, inter alia:

A1 and/or A1* and/or A2 and/or A3+B57 (metsulfuron)+B1 (butachlor);
A1 and/or A1* and/or A2 and/or A3+B57 (metsulfuron)+B2 (butenachlor);
A1 and/or A1* and/or A2 and/or A3+B57 (metsulfuron)+B3 (thenylchlor);
A1 and/or A1* and/or A2 and/or A3+B57 (metsulfuron)+B4 (pretilachlor);
A1 and/or A1* and/or A2 and/or A3+B57 (metsulfuron)+B5 (mefenacet);
A1 and/or A1* and/or A2 and/or A3+B57 (metsulfuron)+B6 (naproanilid);
A1 and/or A1* and/or A2 and/or A3+B57 (metsulfuron)+B7 (propanil);
A1 and/or A1* and/or A2 and/or A3+B57 (metsulfuron)+B8 (etobenzanid);
A1 and/or A1* and/or A2 and/or A3+B57 (metsulfuron)+B9 (dimepiperate);
A1 and/or A1* and/or A2 and/or A3+B57 (metsulfuron)+B10 (molinate);
A1 and/or A1* and/or A2 and/or A3+B57 (metsulfuron)+B11 (thiobencarb);
A1 and/or A1* and/or A2 and/or A3+B57 (metsulfuron)+B12 (pyributicarb);
A1 and/or A1* and/or A2 and/or A3+B57 (metsulfuron)+B13 (quinclorac);
A1 and/or A1* and/or A2 and/or A3+B57 (metsulfuron)+B14a (sulcotrione);
A1 and/or A1* and/or A2 and/or A3+B57 (metsulfuron)+B15 (cycloxydim);
A1 and/or A1* and/or A2 and/or A3+B57 (metsulfuron)+B16 (sethoxydim);
A1 and/or A1* and/or A2 and/or A3+B57 (metsulfuron)+B17 (NBA 061);
A1 and/or A1* and/or A2 and/or A3+B57 (metsulfuron)+B18 (piperophos);
A1 and/or A1* and/or A2 and/or A3+B57 (metsulfuron)+B19 (anilofos);
A1 and/or A1* and/or A2 and/or A3+B57 (metsulfuron)+B20 (fenoxaprop and/or fenoxaprop-P);
A1 and/or A1* and/or A2 and/or A3+B57 (metsulfuron)+B21 (haloxyfop);
A1 and/or A1* and/or A2 and/or A3+B57 (metsulfuron)+B22 (DEH-112);
A1 and/or A1* and/or A2 and/or A3+B57 (metsulfuron)+B23 (JC-940);
A1 and/or A1* and/or A2 and/or A3+B57 (metsulfuron)+B24 (dithiopyr);
A1 and/or A1* and/or A2 and/or A3+B57 (metsulfuron)+B25 (bromobutide);
A1 and/or A1* and/or A2 and/or A3+B57 (metsulfuron)+B26 (cinmethylin);
A1 and/or A1* and/or A2 and/or A3+B57 (metsulfuron)+B27 (CH-900);
A1 and/or A1* and/or A2 and/or A3+B58 (bensulfuron)+B1 (butachlor);
A1 and/or A1* and/or A2 and/or A3+B58 (bensulfuron)+B2 (Butenachlor);
A1 and/or A1* and/or A2 and/or A3+B58 (bensulfuron)+B3 (thenylchlor);
A1 and/or A1* and/or A2 and/or A3+B58 (bensulfuron)+B4 (pretilachlor);
A1 and/or A1* and/or A2 and/or A3+B58 (bensulfuron)+B5 (mefenacet);
A1 and/or A1* and/or A2 and/or A3+B58 (bensulfuron)+B6 (naproanilid);
A1 and/or A1* and/or A2 and/or A3+B58 (bensulfuron)+B7 (propanil);
A1 and/or A1* and/or A2 and/or A3+B58 (bensulfuron)+B8 (etobenzanid);
A1 and/or A1* and/or A2 and/or A3+B58 (bensulfuron)+B9 (dimepiperate);
A1 and/or A1* and/or A2 and/or A3+B58 (bensulfuron)+B10 (molinate);
A1 and/or A1* and/or A2 and/or A3+B58 (bensulfuron)+B11 (thiobencarb);

A1 and/or A1* and/or A2 and/or A3+B58 (bensulfuron)+B12 (pyributicarb);
A1 and/or A1* and/or A2 and/or A3+B58 (bensulfuron)+B13 (quinclorac);
A1 and/or A1* and/or A2 and/or A3+B58 (bensulfuron)+B14a (sulcotrione);
A1 and/or A1* and/or A2 and/or A3+B58 (bensulfuron)+B15 (cycloxydim);
A1 and/or A1* and/or A2 and/or A3+B58 (bensulfuron)+B16 (sethoxydim);
A1 and/or A1* and/or A2 and/or A3+B58 (bensulfuron)+B17 (NBA 061);
A1 and/or A1* and/or A2 and/or A3+B58 (bensulfuron)+B18 (piperophos);
A1 and/or A1* and/or A2 and/or A3+B58 (bensulfuron)+B19 (anilofos);
A1 and/or A1* and/or A2 and/or A3+B58 (bensulfuron)+B20 (fenoxaprop and/or fenoxaprop-P);
A1 and/or A1* and/or A2 and/or A3+B58 (bensulfuron)+B21 (haloxyfop);
A1 and/or A1* and/or A2 and/or A3+B58 (bensulfuron)+B22 (DEH-112);
A1 and/or A1* and/or A2 and/or A3+B58 (bensulfuron)+B23 (JC-940);
A1 and/or A1* and/or A2 and/or A3+B58 (bensulfuron)+B24 (dithiopyr);
A1 and/or A1* and/or A2 and/or A3+B58 (bensulfuron)+B25 (bromobutide);
A1 and/or A1* and/or A2 and/or A3+B58 (bensulfuron)+B26 (cinmethylin);
A1 and/or A1* and/or A2 and/or A3+B58 (bensulfuron)+B27 (CH-900);
A1 and/or A1* and/or A2 and/or A3+B59 (pyrazosulfuron)+B1 (butachlor);
A1 and/or A1* and/or A2 and/or A3+B59 (pyrazosulfuron)+B2 (butenachlor);
A1 and/or A1* and/or A2 and/or A3+B59 (pyrazosulfuron)+B3 (thenylchlor);
A1 and/or A1* and/or A2 and/or A3+B59 (pyrazosulfuron)+B4 (pretilachlor);
A1 and/or A1* and/or A2 and/or A3+B59 (pyrazosulfuron)+B5 (mefenacet);
A1 and/or A1* and/or A2 and/or A3+B59 (pyrazosulfuron)+B6 (naproanilid);
A1 and/or A1* and/or A2 and/or A3+B59 (pyrazosulfuron)+B7 (propanil);
A1 and/or A1* and/or A2 and/or A3+B59 (pyrazosulfuron)+B8 (etobenzanid);
A1 and/or A1* and/or A2 and/or A3+B59 (pyrazosulfuron)+B9 (dimepiperate);
A1 and/or A1* and/or A2 and/or A3+B59 (pyrazosulfuron)+B10 (molinate);
A1 and/or A1* and/or A2 and/or A3+B59 (pyrazosulfuron)+B11 (thiobencarb);
A1 and/or A1* and/or A2 and/or A3+B59 (pyrazosulfuron)+B12 (pyributicarb);
A1 and/or A1* and/or A2 and/or A3+B59 (pyrazosulfuron)+B13 (quinclorac);
A1 and/or A1* and/or A2 and/or A3+B59 (pyrazosulfuron)+B14a (sulcotrione);
A1 and/or A1* and/or A2 and/or A3+B59 (pyrazosulfuron)+B15 (cycloxydim);
A1 and/or A1* and/or A2 and/or A3+B59 (pyrazosulfuron)+B16 (sethoxydim);
A1 and/or A1* and/or A2 and/or A3+B59 (pyrazosulfuron)+B17 (NBA 061);
A1 and/or A1* and/or A2 and/or A3+B59 (pyrazosulfuron)+B18 (piperophos);
A1 and/or A1* and/or A2 and/or A3+B59 (pyrazosulfuron)+B19 (anilofos);
A1 and/or A1* and/or A2 and/or A3+B59 (pyrazosulfuron)+B20 (fenoxaprop and/or fenoxaprop-P);
A1 and/or A1* and/or A2 and/or A3+B59 (pyrazosulfuron)+B21 (haloxyfop);
A1 and/or A1* and/or A2 and/or A3+B59 (pyrazosulfuron)+B22 (DEH-112);
A1 and/or A1* and/or A2 and/or A3+B59 (pyrazosulfuron)+B23 (JC-940);
A1 and/or A1* and/or A2 and/or A3+B59 (pyrazosulfuron)+B24 (dithiopyr);
A1 and/or A1* and/or A2 and/or A3+B59 (pyrazosulfuron)+B25 (bromobutide);
A1 and/or A1* and/or A2 and/or A3+B59 (pyrazosulfuron)+B26 (cinmethylin);
A1 and/or A1* and/or A2 and/or A3+B59 (pyrazosulfuron)+B27 (CH-900);
A1 and/or A1* and/or A2 and/or A3+B60 (cinosulfuron)+B1 (butachlor);
A1 and/or A1* and/or A2 and/or A3+B60 (cinosulfuron)+B2 (butenachlor);
A1 and/or A1* and/or A2 and/or A3+B60 (cinosulfuron)+B3 (thenylchlor);
A1 and/or A1* and/or A2 and/or A3+B60 (cinosulfuron)+B4 (pretilachlor);
A1 and/or A1* and/or A2 and/or A3+B60 (cinosulfuron)+B5 (mefenacet);
A1 and/or A1* and/or A2 and/or A3+B60 (cinosulfuron)+B6 (naproanilid);
A1 and/or A1* and/or A2 and/or A3+B60 (cinosulfuron)+B7 (propanil);
A1 and/or A1* and/or A2 and/or A3+B60 (cinosulfuron)+B8 (etobenzanid);
A1 and/or A1* and/or A2 and/or A3+B60 (cinosulfuron)+B9 (dimepiperate);
A1 and/or A1* and/or A2 and/or A3+B60 (cinosulfuron)+B10 (molinate);
A1 and/or A1* and/or A2 and/or A3+B60 (cinosulfuron)+B11 (thiobencarb);
A1 and/or A1* and/or A2 and/or A3+B60 (cinosulfuron)+B12 (pyributicarb);
A1 and/or A1* and/or A2 and/or A3+B60 (cinosulfuron)+B13 (quinclorac);
A1 and/or A1* and/or A2 and/or A3+B60 (cinosulfuron)+B14a (sulcotrione);
A1 and/or A1* and/or A2 and/or A3+B60 (cinosulfuron)+B15 (cycloxydim);
A1 and/or A1* and/or A2 and/or A3+B60 (cinosulfuron)+B16 (sethoxydim);
A1 and/or A1* and/or A2 and/or A3+B60 (cinosulfuron)+B17 (NBA 061);
A1 and/or A1* and/or A2 and/or A3+B60 (cinosulfuron)+B18 (piperophos);
A1 and/or A1* and/or A2 and/or A3+B60 (cinosulfuron)+B19 (anilofos);
A1 and/or A1* and/or A2 and/or A3+B60 (cinosulfuron)+B20 (fenoxaprop and/or fenoxaprop-P);
A1 and/or A1* and/or A2 and/or A3+B60 (cinosulfuron)+B21 (haloxyfop);
A1 and/or A1* and/or A2 and/or A3+B60 (cinosulfuron)+B22 (DEH-112);
A1 and/or A1* and/or A2 and/or A3+B60 (cinosulfuron)+B23 (JC-940);
A1 and/or A1* and/or A2 and/or A3+B60 (cinosulfuron)+B24 (dithiopyr);
A1 and/or A1* and/or A2 and/or A3+B60 (cinosulfuron)+B25 (bromobutide);

A1 and/or A1* and/or A2 and/or A3+B60 (cinosulfuron)+B26 (cinmethylin);
A1 and/or A1* and/or A2 and/or A3+B60 (cinosulfuron)+B27 (CH-900);
A1 and/or A1* and/or A2 and/or A3+B61 (imazosulfuron)+B1 (butachlor);
A1 and/or A1* and/or A2 and/or A3+B61 (imazosulfuron)+B2 (butenachlor);
A1 and/or A1* and/or A2 and/or A3+B61 (imazosulfuron)+B3 (thenylchlor);
A1 and/or A1* and/or A2 and/or A3+B61 (imazosulfuron)+B4 (pretilachlor);
A1 and/or A1* and/or A2 and/or A3+B61 (imazosulfuron)+B5 (mefenacet);
A1 and/or A1* and/or A2 and/or A3+B61 (imazosulfuron)+B6 (naproanilid);
A1 and/or A1* and/or A2 and/or A3+B61 (imazosulfuron)+B7 (propanil);
A1 and/or A1* and/or A2 and/or A3+B61 (imazosulfuron)+B8 (etobenzanid);
A1 and/or A1* and/or A2 and/or A3+B61 (imazosulfuron)+B9 (dimepiperate);
A1 and/or A1* and/or A2 and/or A3+B61 (imazosulfuron)+B10 (molinate);
A1 and/or A1* and/or A2 and/or A3+B61 (imazosulfuron)+B11 (thiobencarb);
A1 and/or A1* and/or A2 and/or A3+B61 (imazosulfuron)+B12 (pyributicarb);
A1 and/or A1* and/or A2 and/or A3+B61 (imazosulfuron)+B13 (quinclorac);
A1 and/or A1* and/or A2 and/or A3+B61 (imazosulfuron)+B14a (sulcotrione);
A1 and/or A1* and/or A2 and/or A3+B61 (imazosulfuron)+B15 (cycloxydim);
A1 and/or A1* and/or A2 and/or A3+B61 (imazosulfuron)+B16 (sethoxydim);
A1 and/or A1* and/or A2 and/or A3+B61 (imazosulfuron)+B17 (NBA 061);
A1 and/or A1* and/or A2 and/or A3+B61 (imazosulfuron)+B18 (piperophos);
A1 and/or A1* and/or A2 and/or A3+B61 (imazosulfuron)+B19 (anilofos);
A1 and/or A1* and/or A2 and/or A3+B61 (imazosulfuron)+B20 (fenoxaprop and/or fenoxaprop-P);
A1 and/or A1* and/or A2 and/or A3+B61 (imazosulfuron)+B21 (haloxyfop);
A1 and/or A1* and/or A2 and/or A3+B61 (imazosulfuron)+B22 (DEH-112);
A1 and/or A1* and/or A2 and/or A3+B61 (imazosulfuron)+B23 (JC-940);
A1 and/or A1* and/or A2 and/or A3+B61 (imazosulfuron)+B24 (dithiopyr);
A1 and/or A1* and/or A2 and/or A3+B61 (imazosulfuron)+B25 (bromobutide);
A1 and/or A1* and/or A2 and/or A3+B61 (imazosulfuron)+B26 (cinmethylin);
A1 and/or A1* and/or A2 and/or A3+B61 (imazosulfuron)+B27 (CH-900);
A1 and/or A1* and/or A2 and/or A3+B62 (cyclosulfamuron)+B1 (butachlor);
A1 and/or A1* and/or A2 and/or A3+B62 (cyclosulfamuron)+B2 (butenachlor);
A1 and/or A1* and/or A2 and/or A3+B62 (cyclosulfamuron)+B3 (thenylchlor);
A1 and/or A1* and/or A2 and/or A3+B62 (cyclosulfamuron)+B4 (pretilachlor);
A1 and/or A1* and/or A2 and/or A3+B62 (cyclosulfamuron)+B5 (mefenacet);
A1 and/or A1* and/or A2 and/or A3+B62 (cyclosulfamuron)+B6 (naproanilid);
A1 and/or A1* and/or A2 and/or A3+B62 (cyclosulfamuron)+B7 (propanil);
A1 and/or A1* and/or A2 and/or A3+B62 (cyclosulfamuron)+B8 (etobenzanid);
A1 and/or A1* and/or A2 and/or A3+B62 (cyclosulfamuron)+B9 (dimepiperate);
A1 and/or A1* and/or A2 and/or A3+B62 (cyclosulfamuron)+B10 (molinate);
A1 and/or A1* and/or A2 and/or A3+B62 (cyclosulfamuron)+B11 (thiobencarb);
A1 and/or A1* and/or A2 and/or A3+B62 (cyclosulfamuron)+B12 (pyributicarb);
A1 and/or A1* and/or A2 and/or A3+B62 (cyclosulfamuron)+B13 (quinclorac);
A1 and/or A1* and/or A2 and/or A3+B62 (cyclosulfamuron)+B14a (sulcotrione);
A1 and/or A1* and/or A2 and/or A3+B62 (cyclosulfamuron)+B15 (cycloxydim);
A1 and/or A1* and/or A2 and/or A3+B62 (cyclosulfamuron)+B16 (sethoxydim);
A1 and/or A1* and/or A2 and/or A3+B62 (cyclosulfamuron)+B17 (NBA 061);
A1 and/or A1* and/or A2 and/or A3+B62 (cyclosulfamuron)+B18 (piperophos);
A1 and/or A1* and/or A2 and/or A3+B62 (cyclosulfamuron)+B19 (anilofos);
A1 and/or A1* and/or A2 and/or A3+B62 (cyclosulfamuron)+B20 (fenoxaprop and/or fenoxaprop-P);
A1 and/or A1* and/or A2 and/or A3+B62 (cyclosulfamuron)+B21 (haloxyfop);
A1 and/or A1* and/or A2 and/or A3+B62 (cyclosulfamuron)+B22 (DEH-112);
A1 and/or A1* and/or A2 and/or A3+B62 (cyclosulfamuron)+B23 (JC-940);
A1 and/or A1* and/or A2 and/or A3+B62 (cyclosulfamuron)+B24 (dithiopyr);
A1 and/or A1* and/or A2 and/or A3+B62 (cyclosulfamuron)+B25 (bromobutide);
A1 and/or A1* and/or A2 and/or A3+B62 (cyclosulfamuron)+B26 (cinmethylin);
A1 and/or A1* and/or A2 and/or A3+B62 (cyclosulfamuron)+B27 (CH-900);
A1 and/or A1* and/or A2 and/or A3+B64 (azimsulfuron)+B1 (butachlor);
A1 and/or A1* and/or A2 and/or A3+B64 (azimsulfuron)+B2 (butenachlor);
A1 and/or A1* and/or A2 and/or A3+B64 (azimsulfuron)+B3 (thenylchlor);
A1 and/or A1* and/or A2 and/or A3+B64 (azimsulfuron)+B4 (pretilachlor);
A1 and/or A1* and/or A2 and/or A3+B64 (azimsulfuron)+B5 (mefenacet);
A1 and/or A1* and/or A2 and/or A3+B64 (azimsulfuron)+B6 (naproanilid);
A1 and/or A1* and/or A2 and/or A3+B64 (azimsulfuron)+B7 (propanil);
A1 and/or A1* and/or A2 and/or A3+B64 (azimsulfuron)+B8 (etobenzanid);
A1 and/or A1* and/or A2 and/or A3+B64 (azimsulfuron)+B9 (dimepiperate);
A1 and/or A1* and/or A2 and/or A3+B64 (azimsulfuron)+B10 (molinate);
A1 and/or A1* and/or A2 and/or A3+B64 (azimsulfuron)+B11 (thiobencarb);

A1 and/or A1* and/or A2 and/or A3+B64 (azimsulfuron)+ B12 (pyributicarb);
A1 and/or A1* and/or A2 and/or A3+B64 (azimsulfuron)+ B13 (quinclorac);
A1 and/or A1* and/or A2 and/or A3+B64 (azimsulfuron)+ B14a (sulcotrione);
A1 and/or A1* and/or A2 and/or A3+B64 (azimsulfuron)+ B15 (cycloxydim);
A1 and/or A1* and/or A2 and/or A3+B64 (azimsulfuron)+ B16 (sethoxydim);
A1 and/or A1* and/or A2 and/or A3+B64 (azimsulfuron)+ B17 (NBA 061);
A1 and/or A1* and/or A2 and/or A3+B64 (azimsulfuron)+ B18 (piperophos);
A1 and/or A1* and/or A2 and/or A3+B64 (azimsulfuron)+ B19 (anilofos);
A1 and/or A1* and/or A2 and/or A3+B64 (azimsulfuron)+ B20 (fenoxaprop and/or fenoxaprop-P);
A1 and/or A1* and/or A2 and/or A3+B64 (azimsulfuron)+ B21 (haloxyfop);
A1 and/or A1* and/or A2 and/or A3+B64 (azimsulfuron)+ B22 (DEH-112);
A1 and/or A1* and/or A2 and/or A3+B64 (azimsulfuron)+ B23 (JC-940);
A1 and/or A1* and/or A2 and/or A3+B64 (azimsulfuron)+ B24 (dithiopyr);
A1 and/or A1* and/or A2 and/or A3+B64 (azimsulfuron)+ B25 (bromobutide);
A1 and/or A1* and/or A2 and/or A3+B64 (azimsulfuron)+ B26 (cinmethylin);
A1 and/or A1* and/or A2 and/or A3+B64 (azimsulfuron)+ B27 (CH-900);

The abovementioned combinations can also optionally be improved by adding the safener C3-1.

It may also be advantageous to replace the safener compound C2-1 by or to use the safener compound C2-1 together with one or more herbicides having safener action and/or safeners. This applies in a similar manner to the safener C3-1.

Thus, in the abovementioned combinations, daimuron (B42)) and/or quinclorac (B13)) can additionally improve the herbicidal activity against *cyperus* spp. and grasses, and/or they can replace some or all of the safener C2-1.

Furthermore, the safener C2-1 can advantageously be replaced by or used together with one or more of the compounds from the following group:
ethyl 1-(2,4-dichlorophenyl)-5-(ethoxycarbonyl)-5-methyl-2-pyrazoline-3-carboxylate (C1-1),
ethyl 1-(2,4-dichlorophenyl)-5-methylpyrazole-3-carboxylate (C1-2),
ethyl 1-(2,4-dichlorophenyl)-5-isopropylpyrazole-3-carboxylate (C1-3),
ethyl 1-(2,4-dichlorophenyl)-5-(1,1-dimethylethyl)-pyrazole-3-carboxylate (C1-4),
ethyl 1-(2,4-dichlorophenyl)-5-phenylpyrazole-3-carboxylate (C1-5),
ethyl 1-(2,4-dichlorophenyl)-5-trichloromethyl-(1H)-1,2,4-triazole-3-carboxylate (C1-6, fenchlorazol)
ethyl 5-(2,4-dichlorobenzyl)-2-isoxazolin-3-carboxylate (C1-7),
ethyl 5-phenyl-2-isoxazoline-3-carboxylate (C1-8),
1,3-dimethylbut-1-yl (5-chloroquinolin-8-yloxy)acetate (C2-2),
4-allyloxybutyl (5-chloroquinolin-8-yloxy)acetate (C2-3),
1-allyloxyprop-2-yl (5-chloroquinolin-8-yloxy)acetate (C2-4),
ethyl (5-chloroquinolin-8-yloxy)acetate (C2-5),
methyl (5-chloroquinolin-8-yloxy)acetate (C2-6),
allyl (5-chloroquinolin-8-yloxy)acetate (C2-7),
2-(2-propylideneiminooxy)-1-ethyl (5-chloroquinolin-8-yloxy)acetate (C2-8),
2-oxoprop-1-yl (5-chloroquinolin-8-yloxy)acetate (C2-9),
diethyl (5-chloroquinolin-8-yloxy)malonate,
diallyl (5-chloroquinolin-8-yloxy)malonate,
methyl ethyl (5-chloroquinolin-8-yloxy)malonate,
2,4-dichlorophenoxyacetic acid (ester) (2,4-D),
2-(4-chloro-2-methylphenoxy)propionic ester (mecoprop),
MCPA,
3,6-dichloro-2-methoxybenzoic acid (ester) (dicamba) and
ethyl 5,5-diphenyl-2-isoxazoline-3-carboxylate (C3-1).

In addition, the mixtures of the invention may comprise, to round off the properties, additionally, in most cases in minor amounts, one, two or more of the following pesticides (herbicides, insecticides, fungicides, etc.):

abamectin, AC94377, AC263222, AC3-103630, acephate, aclonifen, acrinathrin, acypectas, AKH-7088, alachlor, alanycarb, aldicarb, aldoxycarb, allethrin, alloxydim, alpha-cypermethrin, ametryn, amidosulfuron, amitraz, amitrole, ammonium sulfamate, ancymidol, anilazine, anthraquinone, asulam, atrazine, azaconazole, azadirachtin, azamethiphos, azinphos-ethyl, azinphos-methyl, azocyclotin, BAS480F, BAS490F, benalaxyl, benazolin, bendiocarb, benfluralin, benfuracarb, benomyl, benoxacor, bensulide, bensultap, benzoximate, beta-cyfluthrin, beta-cypermethrin, bifenox, bifenthrin, bilanafos, bioallethrin, bioallethrin (S-cyclopentenyl isomer), bioresmethrin, biphenyl, bitertanol, blasticidin-S, borax, Bordeaux mixture, brodifacoum, bromacil, bromadiolone, bromethalin, bromofenoxim, bromopropylate, bromoxynil, bromuconazole, bronopol, bupirimate, buprofezin, butamifos, butocarboxim, butoxycarboxim, butralin, butylamine, butylate, cadusafos, calcium polysulfide, captafol, captan, carbaryl, carbendazim, carbetamide, carbofuran, carbosulfan, carboxin, cartap, CGA50439, CGA183893, CGA219417, chinomethionat, chlomethoxyfen, chloralose, chloramben, chlorbromuron, chlorbufam, chlordane, chlorethoxyfos, chlorfenvinphos, chlorfluazuron, chlorflurenol, chloridazon, chlormephos, chlormequat, chlornitrofen, chloracetic acid, chlorobenzilate, chloroneb, chlorophacinone, chloropicrin, chlorothalonil, chlorotoluron, chlorophonium, chlorpropham, chlorpyrifos, chlorpyrifos-methyl, chlorsulfuron, chlorthal, chlorthiamid, chlozolinate, CL26691, CL304415, clethodim, clodinafop, cloethocarb, clofentezine, clomeprop, cloprop, clopyralid, cloquintocet, cloxyfonac, copper hydroxide, copper oxychloride, copper sulfate, coumaphos, coumatetralyl, 4-CPA, cuprous oxide, cyanamide, cyanazine, cyanophos, cycloate, cycloprothrin, cyfluthrin, beta-cyfluthrin, cyhalothrin, lambda-cyhalothrin, cyhexatin, cymoxanil, cypermethrin, alpha-cypermethrin, beta-cypermethrin, zeta-cypermethrin, cyphenotrin, cyproconazole, cyromazine, daminozide, dazomet, 2,4-DB, DCIP, debacarb, decan-1-ol, deltamethrin, demeton-S-methyl, desmedipham, desmetryn, diafenthiuron, diazinon, dichlobenil, dichlofluanid, dichlone, dichlormid, dichlorophen, 1,3-dichloropropene, dichlorprop, dichlorprop-P, dichlorvos, diclofop, diclomezine, dicloran, diclofol, dicrotophos, dienochlor, diethofencarb, diethyltoluamide, difenacoum, diefenoconazole, difenzoquat, difethialone, diflubenzuron, diflufenican, dikegulac, dimefuron, dimethachlor, dimethametryn, dimethenamid, dimethipin, dimethirimol, dimethoate, dimethomorph, dimethyl phthalate, dimethylvinphos, diniconazole, dinitramine, dinocap, dinoterb, diofenolan, dioxabenzofos, diphacinone, diphenamid, diphenylamine, dipropyl pyridine-2,5-dicarboxylate, diquat, disulfuton, dithianon, diuron, DKA-24, DNOC, dodemorph, dodine, edifenphos, empenthrin, endosulfan, endothal, ENT8184, EPN, EPTC, ergocalciferol, esfenvalerate, esprocarb, ET751, ethalfluralin, ethametsulfuron-methyl, ethephon, ethiofencarb, ethion, ethirimol, ethofumesate, ethoprophos, ethoxyquin, ethychlozate, ethylene dibromide, ethylene dichloride, etofenprox, etridiazole, F8426, famphur, fenamiphos, fenarimol, fenazaquin, fenbuconazole, fenbutatin oxide, fenchlorazole, fenclorim, fenfuram, fenitrothion, fenobucarb, fenothiocarb, fenoxycarb, fenpiclonil, fenpropathrin, fenpropidin, fenpropimorph, fenpyroximate, fenthion, fentin, fenuron, fenvalerate, ferbam, ferbam, ferimzone, fipronil, flamprop, flamprop-M, flazasulfuron, flocoumafen, fluazifop, fluazifop-P, fluazinam, fluazuron, fluchloralin, flucycloxuron, flucythrinate, fludioxonil, flufenoxuron, flumetralin, flumetsulam, flumiclorac, flumioxazin, fluometuron, fluoroacetamide, fluoroglycofen, fluoromide, flupoxam, flupropanate, fluquinconazole, flurazole, flurenol, fluridone, flurochloridone, fluroxypyr, flurprimidol, flurtamone, flusilazole, flusulfamide, flutolanil, flutriafol, tau-fluvalinate, fluxofenim, folpet, fomesafen, fonofos, forchlorfenuron, formetanate, formothion, fosamine, fosetyl, fosthiazate, fuberidazole, furalaxyl, furathiocarb, furilazole, gibberellic acid, gibberellin $A_4$ gibberellin $A_7$, guazatine, GY-81, halfenprox, halosulfuron, HC-252, gamma-HCH, heptachlor, heptenophos, hexachlorobenzene, hexaconazole, hexaflumuron, hexazinone, hexythiazox, hydramethylnon, 2-hydrazinoethanol, hyprodrene, 8-hydroxyquinoline sulfate, hymexazol, ICIA0858, ICIA5504, imazalil, imazamethabenz, imazapyr, imazaquin, imazethapyr, imibenconazole, imidacloprid, iminoctadien, inabenfide, indol-3-ylacetic acid, 4-indol-3-ylbutyric acid, ipconazole, iprobenfos, iprodione, isazofos, isofenphos, isopamphos, isoprocarb, isoprothiolane, isoproturon, isouron, isoxaben, isoxapyrifop, isoxathion, kasugamycin, KIH9201, lactofen, lambda-cyhalothrin, lenacil, linuron, lufenuron, malathion, maleic hydrazide, mancopper, mancozeb, maneb, MCPA-thioethyl, MCPB, mecarbam, mefluidide, mepanipyrim, mephosfolan, mepiquat, mepronil, metalaxyl, metaldehyde, metam, metamitron, metazachlor, metconazole, methabenzthiazuron, methacrifos, methamidophos, methasulfocarb, methidathion, methiocarb, methomyl, methoprene, methoxychlor, methylarsonic acid, methyl bromide, methyldymron, methyl isothiocyanate, metiram, metobenzuron, metobromuron, metolcarb, metoxuron, metribuzin, mevinphos, milbemectin, MK-243, monocrotophos, monolinuron, muscalure, myclobutanil, nabam, naled, naphthenic acid, 2-(1-naphthyl)acetamide, (1-naphthyl)acetic acid, (2-naphthoyloxy)acetic acid, napropamide, naptalam, natamycin, NC-330, neburon, NI-25, nickel bis(dimethyldithiocarbamate), niclosamide, nicotine, nitenpyram, nithiazine, nitrapyrin, nitrothal-isopropyl, norflurazon, nuarimol, octhilinone, 2-(octylthio)ethanol, ofurace, omethoate, orbencarb, oryzalin, oxabetrinil, oxadixyl, oxamyl, oxine-copper, oxolinic acid, oxycarboxin, oxydemeton-methyl, paclobutrazol, paraquat, parathion, parathion-methyl, pebulate, pefurazoate, penconazole, pencycuron, pentachlorophenol, pentanochlor, permethrin, phenmedipham, phenothrin, phenthoate, 2-phenylphenol, N-phenylphthalamic acid, phorate, phosalone, phosdiphen, phosmet, phosphamidon, phoxim, phthalide, pindone, piperalin, piperonyl butoxide, pirimicarb, pirimiphos-ethyl, pirimiphos-methyl, polyoxins, prallethrin, pretilachlor, primisulfuron, probenazole, prochloraz, procymidone, prodiamine, profenofos, prohexadione, prometon, propachlor, propamocarb, propaphos, propaquizafop, propargite, propazine, propetamphos, propham, propiconazole, propineb, propisochlor, propoxur, propyzamide, prosulfocarb, prosulfuron, prothiofos, pymetrozine, pyraclofos, pyrethrins, pyridaben, pyridaphenthion, pyridate, pyrifenox, pyrimethanil, pyrimidifen, pyriproxyfen, pyrithiobac-sodium, pyroquilon, quinalophos, quinmerac, quinoclamine, quintozene, quizalofop, quizalofop-P, resmethrin, rimsulfuron, rotenone, RU15525, S421, siduron, silafluofen, smazine, sodium fluoroacetate, SSF-109, SSI-121, streptomycin, strychnine, sulcofuron, sulfentrazone, sulfluramid, sulfometuron, sulfotep, sulfur, suiprofos, tar oils, 2,3,6-TBA, TCA-sodium, tebuconazole, tebufenozide, tebufenpyrad, tebutam, tebuthiuron, tecloftalam, tecnazene, teflubenzuron, tefluthrin, temephos, terbacil, terbufos, terbumeton, terbuthylazine, terbutryn, tetrachlorvinphos, tetraconazole, tetradifon, tetramethrin, tetramethrin[(1R)-isomers], thiabendazole, thidiazuron, thifensulfuron, thifluzamide, thiocyclam, thiodicarb, thiofanox, thiometon, thiophanate-methyl, thiram, tiocarbazil, tolclofos-methyl, tolylfluanid, tralkoxydim, tralomethrin, transfluthrin, triadimefon, triadimenol, tri-allate, triazamate, triazophos, triazoxide, tribenuron, S,S,S-tributyl phosphorotrithioate, trichlorfen, tricyclazole, tridemorph, trietazine, triflumizole, triflumuron, trifluralin, triflusulfuron, triforine, trimethacarb, trinexapac, triticonazole, uniconazole, validamycin, vamidothion, vernolate, vinclozolin, warfarin, XDE537, XMC, xylylcarb, zineb, ziram.

This results in numerous possibilities of combining two or more active compounds with one another and to use them together for controlling weeds in rice crops without deviating from the essence of the invention.

The herbicidal compositions (combinations) according to the invention have excellent herbicidal activity against a broad spectrum of economically important mono- and dicotyledonous harmful plants. Even perennial weeds which sprout from rhizomes, stem-tubors or other permanent organs and which are difficult to control are covered well by the active compound combinations. Here, it is immaterial whether the substances are applied by the presowing, the preemergence or the post-emergence method.

Among the monocotyledonous weed species, echinochloa and cyperus species from the annual group and permanent cyperus species from among the perennial species, for example, are covered well.

The active compound combinations according to the invention control weeds which are encountered under the specific cultivation conditions in rice, such as, for example, sagittaria, alisma, rotala, monochoria, eleocharis, scirpus, cyperus, etc., very efficiently.

If the herbicidal compositions according to the invention are applied before germination, the emergence of the weed seedlings is either prevented completely, or the weeds grow until they have reached the cotyledon stage, after which they stop to grow and finally die off completely after three to four weeks have passed.

When the active compound combination of the invention is applied to the green parts of the plant by the post-emergence method, the growth is likewise stopped drastically shortly after the treatment. The weed plants remain at the growth stage that they have reached at the time of application, or they die off more or less quickly after a certain period of time, so that it is possible in this manner to eliminate weed competition, which is harmful to crop plants, at a very early stage and lasting by using the novel compositions according to the invention.

Although the compositions according to the invention have excellent herbicidal activity against mono- and dicotyledonous weeds, the crop plant is damaged to a negligible extent, if at all. For this reason, the compositions are highly suitable for selectively controlling undesirable plant growth, especially in rice.

As already mentioned, the harmful plants to be controlled include, specifically, especially grasses, dicotyledonous plants and/or cyperaceae which are otherwise difficult to control. Harmful plants which are, to be controlled preferably with the combinations of type A and type B compounds according to the invention include, inter alia, *Echinochloa colonum, Echinochloa chinesis, Echinochloa crus galli, Leptochloa chin./fil., Paspalum dis., Brachiaria platyphylla, Digitaria* spp., *Ischaemum, Leersia hexandra, Oryza sativa* (Red rice), *Cenchrus echinatus, Rottboellia exaltata, Leersia* and the like from among the grasses, *Monochoria vag., Potamogeton dis., Rotala indica, Marsilea crenata, Ludwigia ad., Salvina* mol., *Ipomoea, Sesbania ex., Heteranthera, Commelinia, Butomus, Aeschynomene, Alisma plantago, Eclypta, Murdania, Xanthium, Alteranthera* spp., *Spenodea zey., Sagittaria, luncus* spp., *Polygonum, Ammania ind.* from among the weeds and *Cyperus diff., Cyperus iria, Fimbristylis litt., Cyperus ferax, Cyperus esculentes* from among the annuals *cyperaceae* and also *Eleocharis* spp., *Scirpus* spp., *Scirpus mucronatus* and *Cyperus rotundus* from among the perennial *cyperaceae*.

In summary, it may be stated that superadditive (synergistic) effects are achieved when sulfonylureas of the formula I and/or their salts are used together wtih one or more active compounds from group B. The activity in the combinations is more pronounced than that of the individual products used employed alone.

These effects permit
the application rate to be reduced,
a broader spectrum of broad-leaved weeds and weed grasses to be controlled,
a more rapid and safer action,
a more prolonged action,
complete control of harmful plants with only one or few applications and
a widening of the period of time when the active compounds in the combination can be applied.

The abovementioned properties are required in weed control practice to keep agricultural crops free from undesirable competing plants and thus to ensure and/or increase yields from a qualitative and quantitative point of view. The combinations according to the invention markedly surpass the prior art with a view to the above-described properties.

Additionally, the combinations according to the invention permit the outstanding control of otherwise resistant harmful plants.

The following examples serve to illustrate the invention:

1. FORMULATION EXAMPLES a) A dust is obtained by mixing 10 parts by weight of an active compound combination according to the invention and 90 parts by weight of talc as inert substance and comminuting the mixture in a hammer mill.

b) A wettable powder which is readily dispersible in water is obtained by mixing 25 parts by weight of active compounds A+B, 64 parts by weight of kaolin-containing quartz as inert substance, 10 parts by weight of potassium ligninsulfonate and 1 part by weight of sodium oleoylmethyltaurate as wetting agent and dispersant, and grinding the mixture in a pinned-disk mill.

c) A dispersion concentrate which is readily dispersible in water is obtained by mixing 20 parts by weight of active compounds A +B with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.), and grinding the mixture in a ball mill to a fineness of below 5 microns.

d) An emulsifiable concentrate is obtained from 15 parts by weight of cyclohexanone as solvent and 10 parts by weight of ethoxylated nonylphenol as emulsifier.

e) Water-dispersible granules are obtained by mixing 75 parts by weight of active compounds A+B, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulation liquid.

f) Water-dispersible granules are also obtained by homogenizing, in a colloid mill, 25 parts by weight of active compounds A+B, 5 parts by weight of sodium 2,2'-dinaphthylmethane-6,6'-disulfonate, 2 parts by weight of sodium oleoylmethyltaurate, 1 part by weight of polyvinyl alcohol, 17 parts by weight of calcium carbonate and 50 parts by weight of water, precomminuting the mixture, subsequently grinding it in a bead mill and atomizing and drying the resulting suspension in a spray tower by means of a single-substance nozzle.

g) Extruder granules are obtained by mixing and grinding 20 parts by weight of active compounds A+B, 3 parts by weight of sodium lignosulfonate, 1 part by weight of carboxymethylcellulose and 76 parts by weight of kaolin and moistening the mixture with water. This mixture is extruded and subsequently dried in a stream of air.

2. BIOLOGICAL EXAMPLES

The examples mentioned below were carried out in the greenhouse, and in some instances, in field trials.

i) Pre-emergence Action Against Weeds

Seeds or rhizome pieces of mono- and dicotyledonous weed plants are placed into sandy loam soil in plastic pots having a diameter of 9 cm and are covered with soil. Weeds which are encountered in the cultivation of rice are cultivated in the soil which is saturated with water, the amount of water that is filled into the pots being such that the water level reaches the surface of the soil or is some millimeters above the soil surface. The active compound combinations according to the invention, formulated in the form of wettable powders or emulsion concentrates, and in parallel experiments the correspondingly formulated individual active compounds are then applied as aqueous suspensions or as emulsions in an amount of water of 300 to 600 l/ha (converted), at different dosages, onto the surface of the soil cover, or they are, in the case of rice, poured into the water used for irrigation.

After the treatment, the pots are placed in a greenhouse under good growth conditions (temperature, atmospheric humidity, water supply) for the weeds. Visual evaluation of the plants or the emergence damage was carried out after the test plants had emerged after a test period of 3 to 4 weeks, in comparison to untreated controls. The experiments are designed statistically, with several, up to five, repetitions. The herbicidal compositions according to the invention have good herbicidal pre-emergence activity against a broad spectrum of weed grasses and broad-leaved weeds.

ii) Post-emergence Activity Against Weeds

Seeds or rhizome pieces of mono- and dicotyledonous weed plants are placed into sandy loam soil in plastic pots, covered with soil and grown in a greenhouse under good growth conditions (temperature, atmospheric humidity, water supply). Weeds which are encountered in the cultivation of rice are cultivated in pots in which the water level is up to 2 cm over the soil surface. Three weeks after sowing, the test plants are treated at the three-leaf stage. The active compound combinations according to the invention, formulated as wettable powders or emulsion concentrates, and, in parallel experiments, the correspondingly formulated individual active compounds are sprayed onto the green parts of the plants at different dosages using an amount of water of 300 to 600 l/ha (converted), and, after about 3 to 4 weeks of the test plants in the greenhouse under optimum growth conditions (temperature, atmospheric humidity, water supply), the effect of the preparations is evaluated visually in comparison to untreated controls. In the case of rice or weeds which are encountered in the cultivation of rice, the active compounds are also added directly to the water for irrigation (application analogous to the so-called granules application) or sprayed onto plants and added to the water for irrigation. The experiments were designed with several, up to five, repetitions. The herbicidal compositions according to the invention also have good herbicidal post-emergence activity against a broad spectrum of economically important weed grasses and broad-leaved weeds.

iii) Evaluation of the Combination Effects in the Examples

For the assessment of the combination effects, the activity of the individual components was added and compared to the effect of the mixtures of the same dosage. In many cases, it became evident that the combinations had higher efficacies than the sum of the individual effects.

In cases with less pronounced effects, the expected value was calculated using Colby's formula and compared to the empirical result. The calculated expected theoretical efficacy of a combination is determined using the formula of S. R. Colby: "Calculation of synergistic and antagonistic responses of herbicide combinations", Weeds 15 (1967), pages 20 to 22.

For combinations of two compounds, this formula is:

$$E = X + Y - \frac{X \cdot Y}{100}$$

and, correspondingly, for combinations of three herbicidally active compounds:

$$E = X + Y + Z + \frac{X \cdot Y \cdot Z}{10,000} - \frac{XY + XZ + YZ}{100}$$

where

X=% damage by herbicide A at an application rate of x kg of ai/ha;

Y=% damage by herbicide B at an application rate of y kg of ai/ha;

Z=% damage by a further herbicide C at an application rate of z kg of ai/ha;

E=expected value, i.e. expected damage by herbicides A+B (or A+B+C) at x+y (or x+y+z) kg of ai/ha.

Synergistic effects were assumed to be present when the empirical value was greater than the expected value. Combinations of individual components of the same activity compounds could also be prepared by using the sum formula.

However, in most cases the synergistic increase in activity is so high that the Colby criterium can be dispensed with; in these cases, the activity of the combination considerably surpasses the formal (calculated) sum of the activities of the individual compounds.

Particular attention has to be drawn to the fact that when the synergism between the active compounds employed here is assessed, the highly different application rates of the individual active compounds have to be taken into consideration. Thus, it is not expedient to compare the activities of the active compound combinations and those of the individual active compounds in each case at identical application rates. The amounts of active compounds that can be saved according to the invention only become evident by the superadditive activity increase when the combined application rates are used, or by the reduction of the application rates of both individual active compounds in the combinations in comparison to the individual active compounds when the effect is in each case the same.

TABLE 1

| Active compound(s) | g of ai/ha | CUMDI % control | ORYSW % damage |
|---|---|---|---|
| A1*) | 1.25 | 60 | 15 |
|  | 2.5 | 80 | 15 |
| C3-1) | 15 | 0 | 0 |
|  | 30 | 0 | 0 |
|  | 60 | 0 | 0 |
| A1*) + C3-1) | 1.25 + 15 | 84 (60 + 0) | 0 |
|  | 2.5 + 30 | 85 (80 + 0) | 0 |

CUMDI = *Cucumis dipsaceus*
ORYSW = *Oryza sativa* (paddy rice)
A1*) = Sodium salt of methyl 4-iodo-2-[3-(4-methoxy-6-methyl-1,3,5-triazin-2-yl)ureidosulfonyl]benzoate = AEF 115008
C3-1) = ethyl 5,5-diphenyl-2-isoxazoline-3-carboxylate
( ) = % activity of the individual active compounds

TABLE 2

| Active compound(s) | g of ai/ha | ECHCO | ELEIN | ORYSW*) |
|---|---|---|---|---|
|  |  | % control |  | % damage |
| A1*) | 1.25 | 0 | 0 | 10 |
|  | 2.5 | 35 | 0 | 25 |
|  | 5 | 37 | 0 | 25 |
| B63a) | 45 | 0 | 0 | 10 |
|  | 60 | 0 | 0 | 10 |
| A1*) + B63a) | 1.25 + 45 | 82 (0 + 0) | 90 (0 + 0) | 15 (10 + 10) |
|  | 2.5 + 45 | 88 (35 + 0) | 90 (0 + 0) | 13 (25 + 10) |

ECHCG = *Echinochloa crusgalli*
ELEIN = *Eleusine indica*
ORYSW = *Oryza sativa*
A1*) = Sodium salt of methyl 4-iodo-2-[3-(4-methoxy-6-methyl-1,3,5-triazin-2-yl)ureidosulfonyl]-benzoate
B63a) = Ethoxysulfuron
( ) = % activity of the individual active compounds
Field trial: Treatment at the 1–2 leaf stage rice, 2–3 leaf stage weed grasses
Evaluation: 28 days after application
*)Regional acceptance level ≦ 30% damage (Latinamerica)

TABLE 2a

| Active compound(s) | g of ai/ha | LEFFI % control | ORYSW*) % damage |
|---|---|---|---|
| A1*) | 1.25 | 0 | 10 |
|  | 2.5 | 73 | 25 |
|  | 5 | 72 | 25 |
| B63a) | 45 | 0 | 10 |
|  | 60 | 0 | 10 |
| A1*) + B63a) | 1.25 + 45 | 90 (0 + 0) | 15 (10 + 10) |
|  | 2.5 + 45 | 90 (73 + 0) | 13 (25 + 10) |

LEFFI = *Leptochloa filiformis*
ORYSW = *Oryza sativa*
A1*) = Sodium salt of methyl 4-iodo-2-[3-(4-methoxy-6-methyl-1,3,5-triazin-2-yl)ureidosulfonyl]-benzoate
B63a) = Ethoxysulfuron
( ) = % activity of the individual active compounds
Field trial: Treatment at the 1–2 leaf stage rice, 2–3 leaf stage weed grasses
Evaluation: 28 days after application
*)Regional acceptance level ≦ 30% damage (Latinamerica)

TABLE 3

| Active compound(s) | g of ai/ha | CYPIR % control | ORYSW % damage |
|---|---|---|---|
| A1*) | 0.75 | 40 | 0 |
|  | 1.5 | 67 | 0 |
|  | 2.5 | 87 | 0 |
| B63a) | 22.5 | 60 | 0 |
|  | 45 | 95 | 0 |
| A1*) + B63a) | 0.75 + 22.5 | 95 (40 + 0) {E = 76} | 0 |
|  | 1.5 + 22.5 | 96 (67 + 60) {E = 87} | 0 |

CYPIR = *Cyperus irria*
ORYSW = *Oryza sativa*
A1*) = Sodium salt of methyl 4-iodo-2-[3-(4-methoxy-6-methyl-1,3,5-triazin-2-yl)ureidosulfonyl]-benzoate
B63a) = Ethoxysulfuron
( ) = % activity of the individual active compounds
{E = } = Expected value, calculated according to Colby
Field trial: Treatment at the 4–5 leaf stage (seed rice) 2 leaf stage weed grasses
Evaluation: 28 days after application

TABLE 4

| Active compound(s) | g of ai/ha | ECHCG % control | ORYSW*) % damage |
|---|---|---|---|
| A1*) | 1.25 | 0 | 0 |
|  | 2.5 | 0 | 0 |
|  | 5 | 0 | 1 |
| B20) | 10 | 0 | 0 |
|  | 20 | 0 | 0 |
| A1*) + B20) | 1.25 + 20 | 73 (0 + 0) | 14 |
|  | 2.5 + 10 | 43 (0 + 0) | 1 |
|  | 2.5 + 20 | 68 (0 + 0) | 15 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]-benzoate
B20) = fenoxaprop-P-ethyl
( ) = % activity of the individual active compounds
*)Field trial: Regional acceptance level = 15% (Southeast Asia)

TABLE 5

| Active compound(s) | g of ai/ha | ECHCG % control | ORYSW % damage |
|---|---|---|---|
| A1*) | 1.25 | 0 | 0 |
|  | 2.5 | 0 | 0 |
|  | 5 | 0 | 1 |

TABLE 5-continued

| Active compound(s) | g of ai/ha | ECHCG % control | ORYSW % damage |
|---|---|---|---|
| B19) | 250 | 30 | 2 |
|  | 500 | 40 | 10 |
| A1*) + B19) | 1.25 + 250 | 50 (0 + 0) | 2 |
|  | 2.5 + 500 | 83 (50 + 0) | 13 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]-benzoate
B19) = anilofos
( ) = % activity of the individual active compounds
Field trial: Treatment at the 2–4 leaf stage rice, evaluation after 28 days

TABLE 6

| Active compound(s) | g of ai/ha | ECHCG % control | ORYSW % damage |
|---|---|---|---|
| A1*) | 2 | 10 | 0 |
| B1) | 300 | 81 | 0 |
|  | 600 | 89 | 0 |
| A1*) + B1) | 2 + 300 | 87 {83} | 0 |
|  | 2 + 600 | 93 {90} | 0 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate
B1) = butachlor
( ) = % activity of the individual active compounds
{ } = Expected value, calculated according to Colby's method
Field trial: Treatment at the 1–2 leaf stage, evaluation 28 days after the application.

TABLE 7

| Active compound(s) | g of ai/ha | ECHCG % control | MASCR % control | ORYSW % damage |
|---|---|---|---|---|
| A1*) | 2 | 10 | 33 | 0 |
| B7) | 1000 | 79 | 0 | 0 |
|  | 2000 | 88 | 0 | 0 |
| A1*) + B7) | 2 + 1000 | 90 (79 + 10) | 83 (33 + 0) | 0 |
|  | 2 + 2000 | 95 {90} | 84 (33 + 0) | 0 |

ECHCG = *Echinochloa crusgalli*
MASCR = *Marsilea crenata*
ORYSW = *Oryza sativa*
A1*) = Sodium salt of methyl 4-iodo-2-[3-(4-methoxy-6-methyl-1,3,5-triazin-2-yl)ureidosulfonyl]benzoate
B7) = propanil
( ) = % activity of the individual active compounds
{ } = Expected value calculated according to Colby's method
Field trial: Treatment at the 1–2 leaf stage, evaluation 28 days after the application.

TABLE 8

| Active compound(s) | g of ai/ha | ECHCG % control | ORYSW % damage |
|---|---|---|---|
| A1*) | 1.5 | 40 | 10 |
|  | 3 | 60 | 10 |
| B7) | 1250 | 0 | 0 |
|  | 2500 | 0 | 0 |
|  | 5000 | 10 | 0 |

TABLE 8-continued

| Active compound(s) | g of ai/ha | ECHCG % control | ORYSW % damage |
|---|---|---|---|
| A1*) + B7) | 1.5 + 2500 | 65 (40 + 0) | 12 |
|  | 1.5 + 5000 | 75 (40 + 10) | 14 |
|  | 3 + 1250 | 70 (60 + 0) | 11 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate
B7) = propanil
( ) = % activity of the individual active compounds
Greenhouse trial: Treatment at the 1–2 leaf stage, evaluation 22 days after the application.

TABLE 9

| Active compound(s) | g of ai/ha | ECHCG % control | ORYSW % damage |
|---|---|---|---|
| A1*) | 1.5 | 40 | 10 |
|  | 3 | 60 | 10 |
| B48) | 19 | 15 | 0 |
|  | 38 | 30 | 0 |
|  | 75 | 40 | 5 |
| A1*) + B48) | 1.5 + 38 | 85 (40 + 30) | 10 |
|  | 3 + 19 | 75 {66} | 11 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate
B22) = KIH 2023 = bispyribuc
( ) = % activity of the individual active compounds
{ } = expected value, calculated according to Colbys method Greenhouse trial: Treatment at the 1–2 leaf stage, evaluation 22 days after the application.

TABLE 10

| Active compound(s) | g of ai/ha | SCIJU % control | ORYSW % damage |
|---|---|---|---|
| A1*) | 1.5 | 40 | 10 |
|  | 3 | 40 | 10 |
| B58) | 7.5 | 35 | 0 |
|  | 15 | 40 | 0 |
|  | 30 | 55 | 2 |
|  | 60 | 60 | 5 |
| B59) | 7.5 | 50 | 0 |
|  | 15 | 55 | 0 |
|  | 30 | 60 | 2 |
| A1*) + B58) | 3 + 7.5 | 85 (40 + 35) | 8 |
|  | 1.5 + 30 | 97 (40 + 55) | 12 |
| A1*) + B59) | 3 + 7.5 | 93 {70} | 8 |
|  | 1.5 + 15 | 96 {73} | 10 |

SCIJU = *Scirpus juncoides*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B58) = bensulfuron
B59) = pyrazosulfuron
{ } = expected value according to Colby
( ) = % activity of the individual active compounds Greenhouse trial: Treatment at the 1–2 leaf stage, evaluation 20 days after the application.

TABLE 11

| Active compound(s) | g of ai/ha | ECHCG % control | ORYSW % damage |
|---|---|---|---|
| A1*) | 1.5 | 40 | 10 |
|  | 3 | 60 | 10 |
| B61) | 8 | 0 | 0 |
|  | 15 | 25 | 0 |
|  | 30 | 50 | 0 |
|  | 60 | 60 | 0 |
| A1*) + B61) | 1.5 + 8 | 76 (40 + 0) | 9 |
|  | 1.5 + 15 | 83 (40 + 25) | 10 |
|  | 1.5 + 60 | 96 {76} | 12 |
|  | 3 + 30 | 93 {80} | 8 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B61) = imazosulfuron
( ) = % activity of the individual active compounds
{ } = expected value according to the Colby method Greenhouse trial: Treatment at the 1–2 leaf stage, evaluation 20 days after the application.

TABLE 12

| Active compound(s) | g of ai/ha | CYPSE % control | ORYSW % damage |
|---|---|---|---|
| A1*) | 1.5 | 10 | 10 |
|  | 3 | 30 | 10 |
| B60) | 15 | 0 | 0 |
|  | 30 | 15 | 0 |
|  | 60 | 15 | 5 |
| A1*) + B60) | 1.5 + 60 | 63 (10 + 15) | 10 |
|  | 3 + 15 | 65 (30 + 0) | 12 |

CYPSE = *Cyperus serotinus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B60) = cinosulfuron
( ) = % activity of the individual active compounds Greenhouse trial: Treatment at the 1–2 leaf stage, evaluation 20 days after the application.

TABLE 13

| Active compound(s) | g of ai/ha | SAGPY % control | ORYSW % damage |
|---|---|---|---|
| A1*) | 1.5 | 30 | 10 |
|  | 3 | 50 | 10 |
| B17) | 50 | 0 | 0 |
|  | 100 | 40 | 0 |
|  | 200 | 80 | 0 |
| A1*) + B17) | 1.5 + 100 | 85 (30 + 40) | 11 |
|  | 3 + 50 | 65 (50 + 0) | 9 |

SAGPY = *Sagittaria pygmaea*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B17) = fentrazamide
( ) = % activity of the individual active compounds Greenhouse trial: Treatment at the 5–6 leaf stage, evaluation 20 days after the application.

TABLE 14

| Active compound(s) | g of ai/ha | SAGPY % control | ORYSW % damage |
|---|---|---|---|
| A1*) | 1.5 | 30 | 10 |
|  | 3 | 50 | 10 |
| B73) | 50 | 10 | 0 |
|  | 100 | 15 | 0 |
|  | 200 | 20 | 5 |
| B13) | 250 | 30 | 0 |
|  | 500 | 30 | 0 |
|  | 1000 | 30 | 0 |
| B4) | 125 | 65 | 15 |
|  | 250 | 70 | 15 |
|  | 500 | 75 | 35 |
| A1*) + B73) | 1.5 + 200 | 75 (30 + 20) | 10 |
|  | 3 + 50 | 85 (50 + 10) | 11 |
| A1*) + B13) | 1.5 + 1000 | 75 (30 + 30) | 10 |
|  | 3 + 250 | 85 (50 + 30) | 11 |
| A1*) + B4) | 1.5 + 500 | 93 {83} | 10 |
|  | 3 + 125 | 97 {75} | 11 |

SAGPY = *Sagittaria pygmaea*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B73) = MY 100
B13) = quinchlorac
B4) = pretilachlor
( ) = % activity of the individual active compounds
{ } = expected value according to Colby Greenhouse trial: Treatment at the 3–4 leaf stage, evaluation 21 days after the application.

TABLE 15

| Active compound(s) | g of ai/ha | SCIMA % control | ORYSW % damage |
|---|---|---|---|
| A1*) | 1.25 | 35 | 5 |
|  | 2.5 | 40 | 10 |
|  | 5 | 45 | 10 |
| B64) | 5 | 78 | 3 |
|  | 9 | 80 | 8 |
|  | 18 | 83 | 10 |
|  | 37 | 85 | 10 |
| A1*) + B64) | 1.25 + 5 | 90 {86} | 11 |
|  | 1.25 + 37 | 95 {90} | 15 |
|  | 2.5 + 37 | 93 {89} | 14 |
|  | 5 + 5 | 90 {88} | 12 |

SCIMA = *Scirpus maritimus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B64) = azimsulfuron
( ) = % activity of the individual active compounds
{ } = expected value according to Colby
Greenhouse trial: Treatment at the 2–3 leaf stage, evaluation 20 days after the application.

TABLE 16

| Active compound(s) | g of ai/ha | CYPSE % control | ORYSW % damage |
|---|---|---|---|
| A1*) | 1.25 | 10 | 5 |
|  | 2.5 | 30 | 10 |
|  | 5 | 50 | 10 |
| B72) | 18.75 | 25 | 3 |
|  | 37.5 | 35 | 8 |
|  | 75 | 60 | 8 |
| A1*) + B72) | 1.25 + 75 | 80 (10 + 60) | 13 |
|  | 2.5 + 18.75 | 75 (30 + 25) | 12 |

CYPSE = *Cyperus serotinus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B72) = LGC40863 = pyribenzoxime
( ) = % activity of the individual active compounds Greenhouse trail: Treatment at the 2–3 leaf stage, evaluation 20 days after the application.

TABLE 17

| Active compound(s) | g of ai/ha | ECHCG % control | ORYSW % damage |
|---|---|---|---|
| A1*) | 1 | 5 | 7 |
|  | 2 | 25 | 12 |
|  | 4 | 45 | 18 |
| B51) | 25 | 37 | 0 |
|  | 50 | 63 | 3 |
|  | 100 | 63 | 6 |
|  | 200 | 80 | 10 |
| B38) | 7.5 | 50 | 0 |
|  | 15 | 52 | 0 |
|  | 30 | 52 | 0 |
| A1*) + B51) | 2 + 25 | 75 (25 + 37) | 8 |
|  | 1 + 200 | 88 {81} | 14 |
| A1*) + B38) | 2 + 7.5 | 85 (25 + 50) | 12 |
|  | 1 + 30 | 75 (5 + 52) | 6 |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B51) = oxadiargyl
B38) = carfentrazone
( ) = % activity of the individual active compounds
{ } = expected value according to the Colby method Field trial: Treatment at the 2 leaf stage, evaluation 14 days after the application.

TABLE 18

| Active compound(s) | g of ai/ha | ECHCG % control | ORYSW % damage |
|---|---|---|---|
| A1*) | 1 | 5 | 7 |
|  | 2 | 25 | 12 |
| B63a) | 5 | 7 | 7 |
|  | 10 | 7 | 7 |
| B20) | 30 | 75 | 0 |
| C3-1) | 30 |  |  |
| A1*) + B63a) | 1 + 5 | 33 (5 + 7) |  |
| A1*) + B63a) + B20) + C3-1) | 1 + 5 + 30 + 30 | 98 (5 + 7 + 75) |  |

ECHCG = *Echinochloa crusgalli*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B63a) = ethoxysulfuron
B20) = fenoxaprop-P
C3-1) = ethyl 5,5-diphenyl-2-isoxazoline-3-carboxylate
( ) = % activity of the individual active compounds Field trial: Treatment at the 1–2 leaf stage, evaluation 14 days after the application.

TABLE 19

| Active compound(s) | g of ai/ha | CYPSE % control | ORYSW % damage |
|---|---|---|---|
| A1*) | 1.5 | 10 | 8 |
|  | 3 | 30 | 12 |
| B70) | 150 | 50 | 0 |
|  | 450 | 65 | 0 |
| B33b) | 100 | 40 | 6 |
|  | 200 | 50 | 8 |
|  | 400 | 80 | 12 |
| A1*) + B70) | 3 + 150 | 85 (30 + 50) | 10 |
|  | 1.5 + 450 | 80 (10 + 65) | 8 |
| A1*) + B33) | 3 + 100 | 85 (30 + 40) | 14 |
|  | 1.5 + 200 | 80 (10 + 50) | 10 |

CYPSE = *Cyperus serotinus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B70) = KP314 (pentoxazone)
B33b) = azole of the formula B33b)
( ) = % activity of the individual active compounds Field trial: Treatment at the 2 leaf stage, evaluation 14 days after the application.

TABLE 20

| Active compound(s) | g of ai/ha | IPOHE % control | ORYSW % damage |
|---|---|---|---|
| A1*) | 2.5 | 30 | 8 |
| B40) | 420 | 65 | 20 |
| B11) | 3300 | 43 | 3 |
| B10) | 4480 | 55 | 0 |
| A1*) + B40) | 2.5 + 420 | 85 {75} | 18 |
| A1*) + B11) | 2.5 + 3300 | 75 {60} | 5 |
| A1*) + B10) | 2.5 + 4480 | 100 (30 + 55) | 7 |

IPOHE = *Ipomoea hederacea*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B40) = triclopyr
B11) = thiobencarb as trade product ™Bolero
B10) = molinate as trade product ™Ordram
( ) = % activity of the individual active compounds
{ } = expected value according to Colby Field trial: Treatment at the 4–6 leaf stage, evaluation 28 days after the application.

TABLE 21

| Active compound(s) | g of ai/ha | CYPSE % control | ORYSW % damage |
|---|---|---|---|
| A1*) | 2.5 | 25 | 8 |
| B12) | 600 | 65 | 3 |
| B9) | 3000 | 45 | 5 |
| B24) | 60 | 60 | 6 |
| B71) | 150 | 55 | 4 |
| A1*) + B12) | 2.5 + 600 | 93 (25 + 65) | 9 |
| A1*) + B9) | 2.5 + 3000 | 83 (25 + 45) | 8 |
| A1*) + B24) | 2.5 + 60 | 88 {70} | 6 |
| A1*) + B71) | 2.5 + 150 | 87 {66} | 7 |

CYPSE = *Cyperus serotinus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B12) = pyributicarb
B9) = dimepiperate
B24) = dithiopyr
B71) = indanofan
( ) = % activity of the individual active compounds
{ } = expected value according to Colby Field trial: Treatment at the 2 leaf stage, evaluation 28 days after the application.

TABLE 22

| Active compound(s) | g of ai/ha | SAGPY % control | ORYSW % damage |
|---|---|---|---|
| A1*) | 2.5 | 20 | 6 |
|  | 5 | 40 | 12 |
| B5) | 600 | 0 | 0 |
|  | 1200 | 0 | 3 |
|  | 2400 | 0 | 10 |
| A1*) + B5) | 2.5 + 2400 | 55 (20 + 0) | 8 |
|  | 5 + 600 | 65 (40 + 0) | 10 |

SAGPY = *Sagittaria pygmaea*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B5) = mefenacet
( ) = % activity of the individual active compounds Field trial: Treatment: 1–2 leaf stage, evaluation 28 days after the application.

TABLE 23

| Active compound(s) | g of ai/ha | CYPIR % control | ORYSW % damage |
|---|---|---|---|
| A1*) | 0.62 | 53 | 3 |
|  | 1.25 | 85 | 8 |
|  | 2.5 | 98 | 12 |
| B39) | 250 | 42 | 0 |
|  | 400 | 78 | 0 |
|  | 800 | 97 | 3 |
| A1*) + B39) | 0.62 + 250 | 99 (53 + 42) | 0 |

CYPIR = *Cyperus iria*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B39) = bentazone
( ) = % activity of the individual active compounds Field trial: Treatment: 4–6 leaf stage, evaluation 36 days after the application.

TABLE 24

| Active compound(s) | g of ai/ha | CYPIR % control | ORYSW % damage |
|---|---|---|---|
| A1*) | 2.5 | 17 | 0 |
|  | 5 | 27 | 0 |
| B44) | 400 | 30 | 0 |
| A1*) + B44) | 2.5 + 400 | 67 (17 + 30) | 0 |
|  | 5 + 400 | 78 (27 + 30) | 0 |

CYPIR = *Cyperus iria*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B44) = clomazone
( ) = % activity of the individual active compounds Field trial: Treatment by the pre-emergence method, evaluation 53 days after the application.

TABLE 25

| Active compound(s) | g of ai/ha | POLCO % control | ORYSW % damage |
|---|---|---|---|
| A1*) | 1.25 | 35 | 6 |
|  | 2.5 | 80 | 12 |
| B31) | 240 | 45 | 8 |
|  | 480 | 80 | 10 |

TABLE 25-continued

| Active compound(s) | g of ai/ha | POLCO % control | ORYSW % damage |
|---|---|---|---|
| A1*) + B31) | 1.25 + 240 | 84 (35 + 45) | 11 |

POLCO = *Polygonum convolvulus*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B31) = dicamba
( ) = % activity of the individual active compounds Field trial: Treatment at the 3 leaf stage, evaluation 33 days after the application.

TABLE 26

| Active compound(s) | g of ai/ha | COMBE % control | ORYSW % damage |
|---|---|---|---|
| A1*) | 2.5 | 47 | 0 |
|  | 5 | 67 | 0 |
| B57) | 1 | 20 | 0 |
|  | 2 | 68 | 0 |
| A1*) + B57) | 2.5 + 1 | 73 (47 + 20) | 0 |

COMBE = *Commelina benghalensis*
ORYSW = *Oryza sativa*
A1*) = Sodium salt of methyl 4-iodo-2-[3-(4-methoxy-6-methyl-1,3,5-triazin-2-yl)ureidosulfonyl]benzoate = iodosulfuron
B57) = metsulfuron
( ) = % activity of the individual active compounds Field trial: Treatment at the 3 leaf stage, evaluation 33 days after the application.

What is claimed is:

1. A herbicidal composition, comprising a synergistic combination of A) at least one synergistically herbicidally active compound from the group of the substituted phenylsulfonylureas of the formula I and their agriculturally accepted, i.e. acceptable and compatible, salts

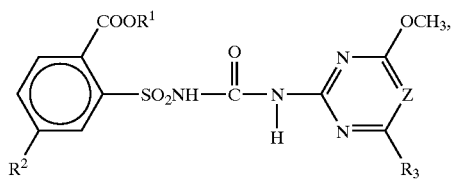

in which
R$^1$ is (C$_1$–C$_8$)-alkyl, (C$_3$–C$_4$)-alkenyl, (C$_3$–C$_4$)-alkynyl or (C$_1$–C$_4$)-alkyl, which is mono- to tetrasubstituted by radicals from the group consisting of halogen and (C$_1$–C$_2$)-alkoxy;
R$^2$ is I or CH$_2$NHSO$_2$CH$_3$ when
Z is CH
or
R$^2$ is CH$_2$NHSO$_2$CH$_3$ when
Z is N
R$^3$ is methyl or methoxy
and
B) at least one synergistically herbicidally active compound from the group of the compounds consisting of
Ba) herbicides which are selective in rice, mainly against grasses, comprising B1)
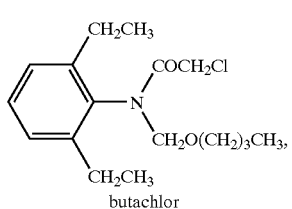
butachlor B2)
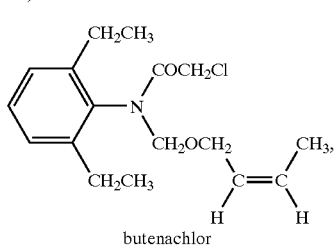
butenachlor B3)
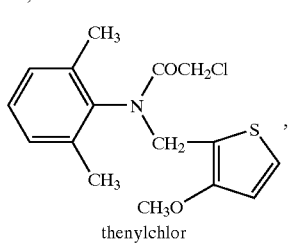
thenylchlor B4)
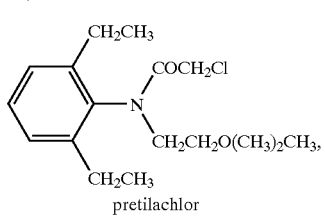
pretilachlor B5)
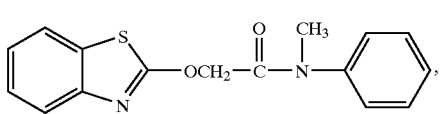
mefenacet B5a)
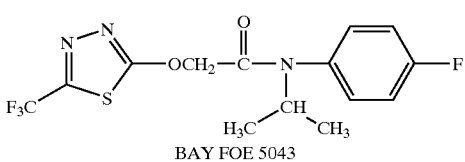
BAY FOE 5043

B6)
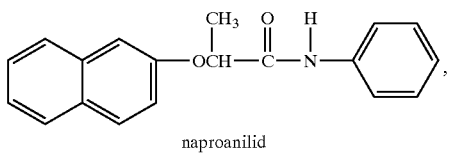
naproanilid

-continued

B7)
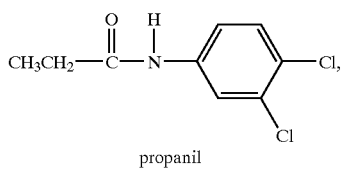
propanil

B8)
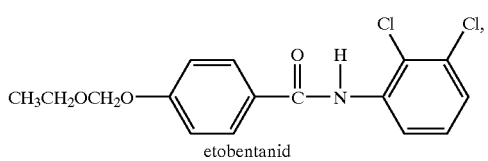
etobentanid

B9)
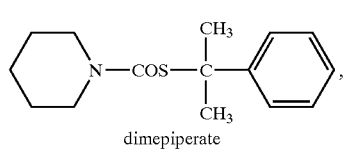
dimepiperate

B10)
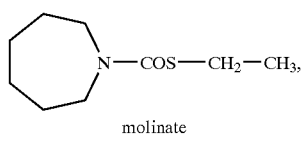
molinate

B11)
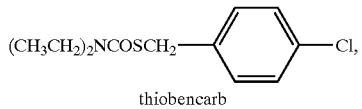
thiobencarb

B12)
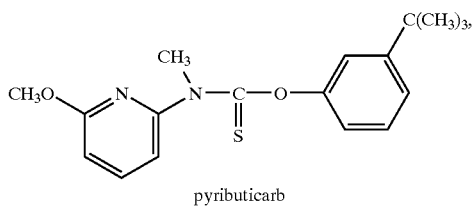
pyributicarb

B13)
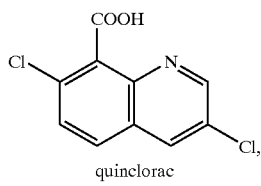
quinclorac

B14a)
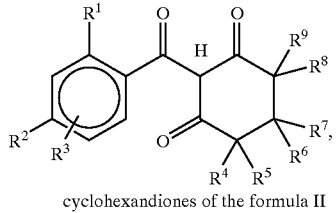
cyclohexandiones of the formula II in which $R^1$ is halogen, $(C_1-C_4)$-alkoxy, $(C_1-C_4)$-alkyl, $(C_1-C_4)$-haloalkyl, $-NO_2$, $-CN$ or $S(O)_n R^{10}$;

$R^2$ and $R^3$ independently of one another are hydrogen, halogen, $(C_1-C_4)$-alkyl, $(C_1-C_4)$-alkoxy, $(C_1-C_4)$-haloalkoxy, $(C_1-C_4)$-haloalkyl, $-NO_2$, $-CN$ or $S(O)_m R^{11}$, $-NR^{12}R^{13}$, $-NR^{14}-CO-R^{15}$;

$R^4$ is hydrogen, $(C_1-C_4)$-alkyl or $-CO-O-(C_1-C_4)$-alkyl;

$R^5$, $R^6$, $R^7$, $R^8$, $R^9$ independently of one another are hydrogen or $(C_1-C_4)$-alkyl or $-CO-R^{16}$;

$R^{10}$ is $(C_1-C_4)$-alkyl, $(C_1-C_4)$-haloalkyl or $(C_1-C_4)$-alkoxy;

$R^{11}$ is $(C_1-C_4)$-alkyl, $(C_1-C_4)$-haloalkyl, phenyl, benzyl or $-NR^{17}R^{18}$;

$R^{12}$ and $R^{13}$ independently or one another are hydrogen or $(C_1-C_4)$-alkyl;

$R^{14}$ is hydrogen or $(C_1-C_4)$-alkyl;

$R^{15}$ is $(C_1-C_4)$-alkyl;

$R^{16}$ is hydrogen, $(C_1-C_4)$-alkyl, $(C_1-C_4)$-haloalkyl or $(C_1-C_4)$-alkoxy;

$R^{17}$ and $R^{18}$ independently of one another are hydrogen or $(C_1-C_4)$-alkyl; and n and m independently or one another are 0, 1 or 2, B15) cycloxydim

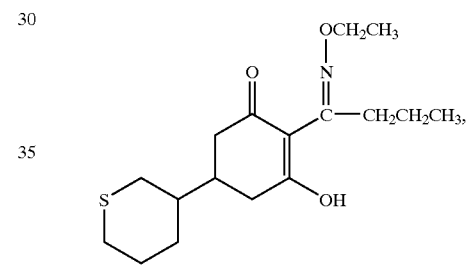

B16)

sethoxydim

B17)

Bayer NBA 061

B18)

piperophos

-continued

B19) anilofos

B20) fenoxaprop, fenoxaprop-P

B21) haloxyfop

B22) cyhalofop

B23) JC-940

B24) dithiopyr

B25) bromobutide

-continued

B26)

cinmethylin

B27) CH-900

Bb) herbicides which are selective in rice, mainly against dicotyledonous harmful plants and cyperaceae, comprising

B28) 2,4-D

B29) mecoprop, mecoprop-P

B30) MCPA

B31)

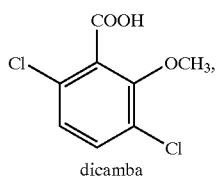

dicamba

B32)

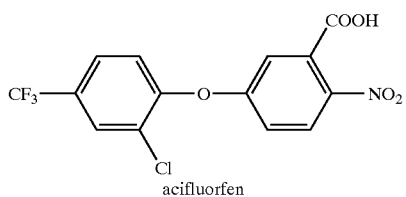

acifluorfen

B33)

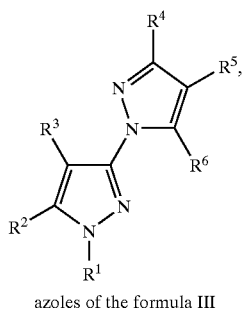

azoles of the formula III in which
R$^1$ is (C$_1$–C$_4$)-alkyl,
R$^2$ is (C$_1$–C$_4$)-alkyl, (C$_1$–C$_4$)-alkylthio or (C$_1$–C$_4$)-alkoxy, each radical of which may be substituted by one or more halogen atoms, or
R$^1$ and R$^2$ together from the group (CH$_2$)$_m$ where m=3 or 4
R$^3$ is hydrogen or halogen,
R$^4$ is hydrogen or (C$_1$–C$_4$)-alkyl,
R$^5$ is hydrogen, nitro, cyano or one of the groups —COOR$^7$, —C(=X)NR$^7$R$^8$ or —C(=X)R$^{10}$,
R$^6$ is hydrogen, halogen, cyano, (C$_1$–C$_4$)-alkyl, (C$_1$–C$_4$)-alkylthio or —NR$^{11}$R$^{12}$,
R$^7$ and R$^8$ are identical or different and are hydrogen or (C$_1$–C$_4$)-alkyl, or
R$^7$ and R$^8$ are identical with the nitrogen to which they are attached form a saturated 5- or 6-membered carbocyclic ring,
R$^{10}$ is hydrogen or (C$_1$–C$_4$)-alkyl, where the latter may be unsubstituted or substituted by one or more halogen atoms, and
R$^{11}$ and R$^{12}$ are identical or different and are hydrogen, (C$_1$–C$_4$)-alkyl or (C$_1$–C$_4$)-alkoxycarbonyl, where
R$^{11}$ and R$^{12}$ together with the nitrogen to which they are attached may form a 3-, 5- or 6-membered carbocyclic or aromatic ring in which one carbon atom may optionally be replaced by an oxygen atom,

B34)

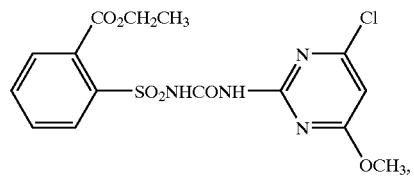

chlorimuron

B35)

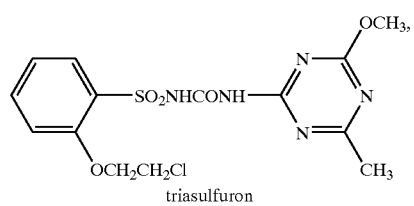

triasulfuron

B36)

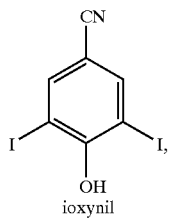

ioxynil

B37)

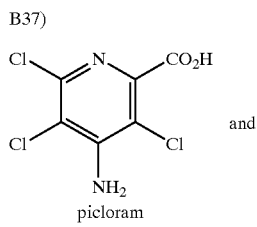

picloram and

B38)

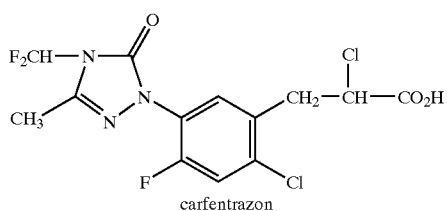

carfentrazon

Bc) herbicides which are selective in rice, mainly against cyperaceae, comprising B39)
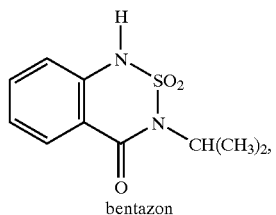
bentazon
B40)
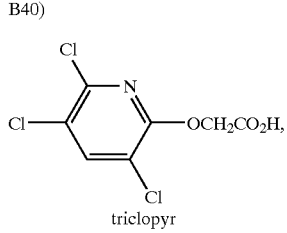
triclopyr
B41)
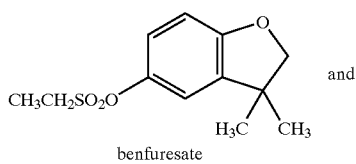
benfuresate
and
B42)
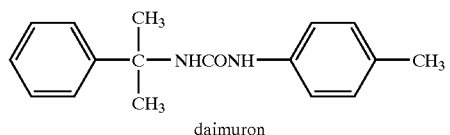
daimuron
and
Bd) herbicides which are selective in rice, mainly against grasses and dicotyledonous harmful plants and also against harmful cyperaceae plants, comprising
B43)
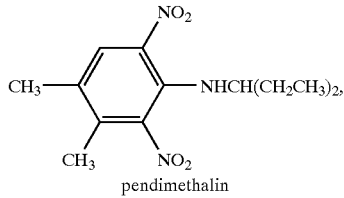
pendimethalin
B44)
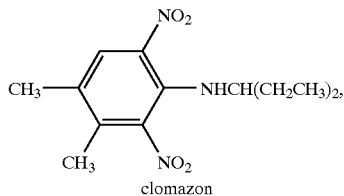
clomazon
B45)
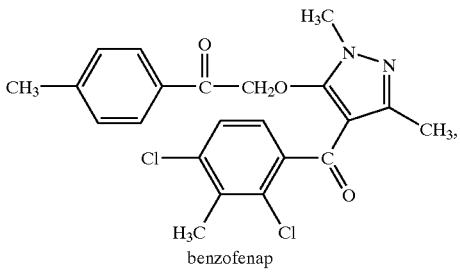
benzofenap
B46)
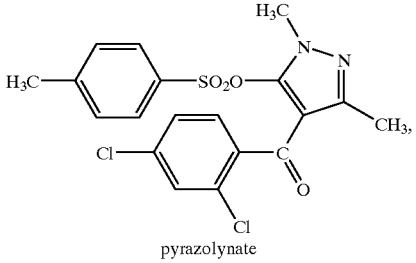
pyrazolynate
B47)
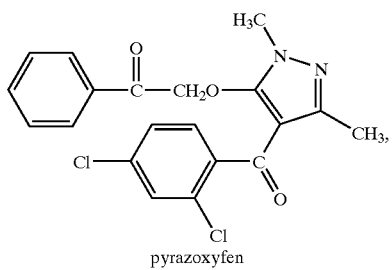
pyrazoxyfen
B48)
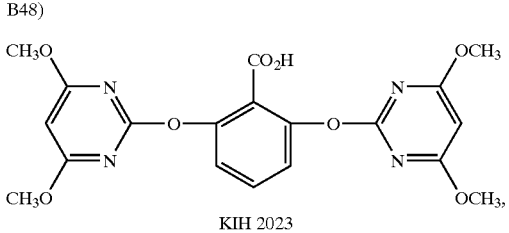
KIH 2023
B49)
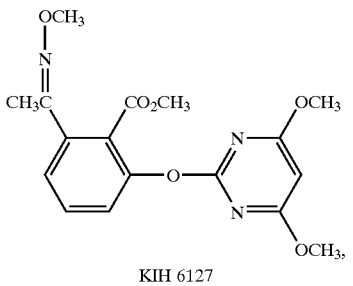
KIH 6127

B50)
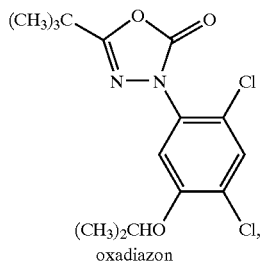
oxadiazon
B51)
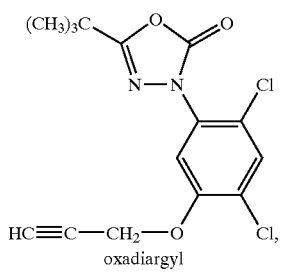
oxadiargyl
B52)
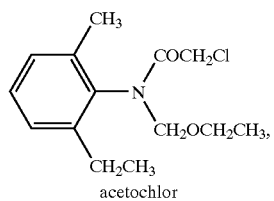
acetochlor
B53)
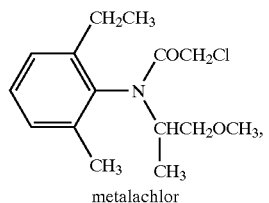
metalachlor
B54)
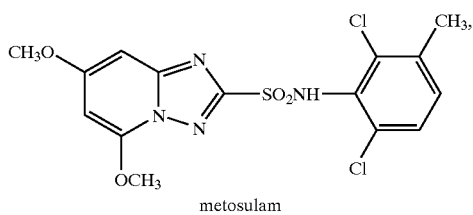
metosulam
B55)
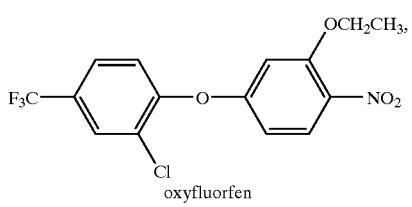
oxyfluorfen
B56)
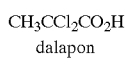
$CH_3CCl_2CO_2H$
dalapon
B57)
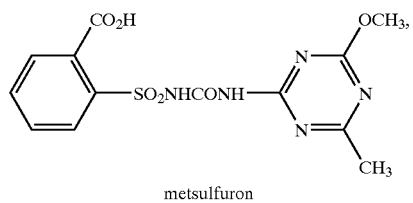
metsulfuron
B58)
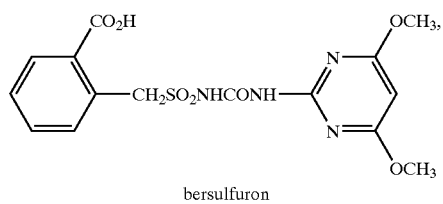
bersulfuron
B59)
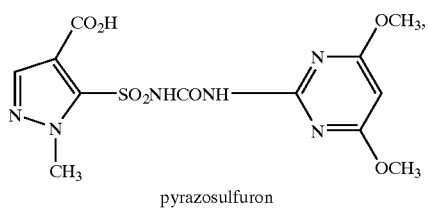
pyrazosulfuron
B60)
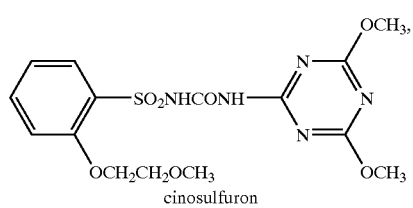
cinosulfuron
B61)
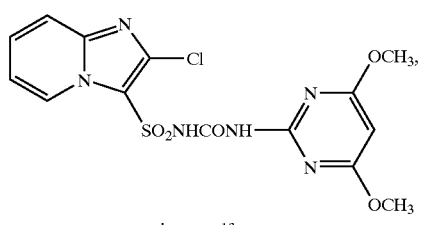
imazosulfuron
B62)
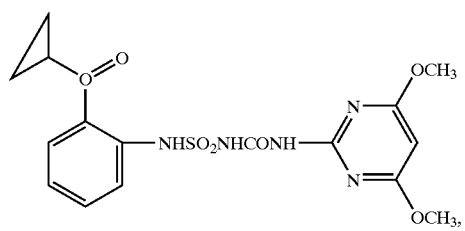
AC 322, 140 (cyclosulfamuron)

B63)

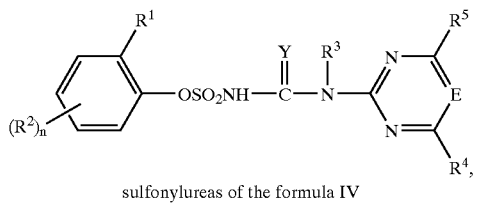

sulfonylureas of the formula IV in which
a) $R^1$ is ethoxy, propoxy or isopropoxy and $R^2$ is halogen, $NO_2$, $CF_3$, CN, $(C_1-C_4)$-alkyl, $(C_1-C_4)$-alkoxy, $(C_1-C_4)$-alkylthio or $((C_1-C_4)$-alkoxy) carbonyl and n is 0, 1, 2, or 3 or
b) $R^1$ is saturated or unsaturated $(C_1-C_8)$-alkoxy, which is substituted by halogen, saturated or unsaturated $(C_1-C_6)$-alkoxy, a radical of the formula $((C_1-C_6)$-alkyl)-S—, $((C_1-C_6)$-alkyl)-SO—, $((C_1-C_6)$-alkyl)-$SO_2$—, $((C_1-C_6)$-alkyl)-O—CO—, $NO_2$, CN or phenyl; furthermore $(C_2-C_8)$-alkenyloxy or -alkynyloxy and $R^2$ is saturated or unsaturated $(C_1-C_8)$-alkyl, phenyl, phenoxy, $(C_1-C_4)$-alkoxy)carbonyl, where all of the abovementioned radicals $R^2$ may be substituted by halogen, $NO_2$, $(C_1-C_4)$-alkylsulfonyl or -sulfinyl and n is 0, 1, 2 or 3 or
c) $R^1$ is $(C_1-C_8)$-alkoxy and $R^2$ is $(C_2-C_8)$-alkenyl or —alkynyl, phenyl, phenoxy, where the radicals mentioned above for $R^2$ are unsubstituted or substituted by halogen, $(C_1-C_4)$-alkoxy or $(C_1-C_4)$-alkylthio, or $(C_1-C_4)$-alkylsulfonyl or -sulfinyl and n is 1, 2 or 3 or
d) $R^1$ is, in each case in the 2-position on the phenyl radical, halogen, methoxy, ethyl or propyl, $R^2$ is $((C_1-C_4)$-alkoxy)carbonyl in the 6-position on the phenyl radical and n=1 and in all cases a) to d)
$R^3$ is hydrogen, saturated or unsaturated $(C_1-C_8)$-alkyl or $(C_1-C_4)$-alkoxy,
$R^4, R^5$ is independently of one another are hydrogen, halogen, $(C_1-C_4)$-alkyl, $(C_1-C_4)$-alkoxy, $(C_1-C_4)$-alkylthio, where the three last-mentioned radicals are unsubstituted or substituted by halogen, $(C_1-C_4)$-alkoxy or $(C_1-C_4)$-alkylthio, Y is O or S and
E is CH or N,

B64)

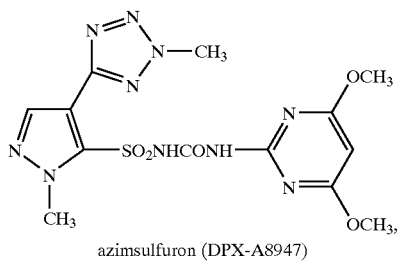

azimsulfuron (DPX-A8947)

B65)

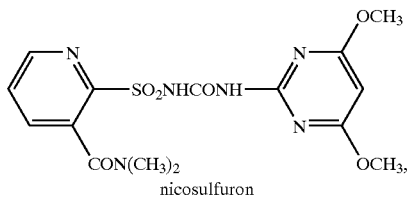

nicosulfuron

B66)

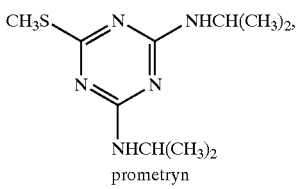

prometryn

B67)

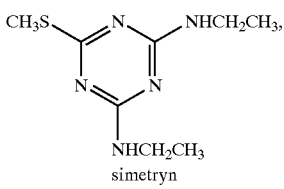

simetryn

B68)

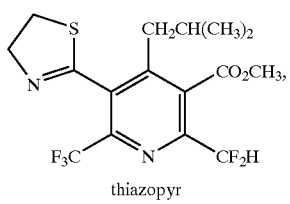

thiazopyr

B69)

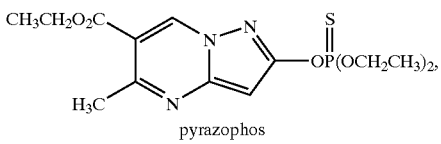

pyrazophos

B70)

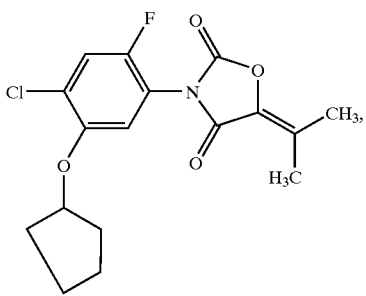

pentoxazone

B71)

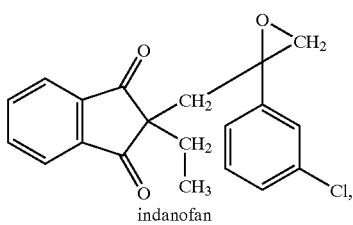

indanofan

-continued

B72)

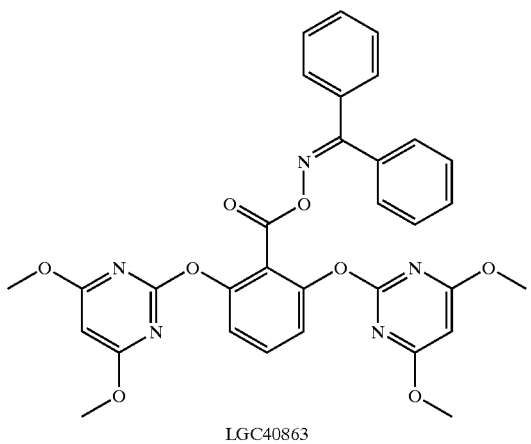

LGC40863 and

B73)

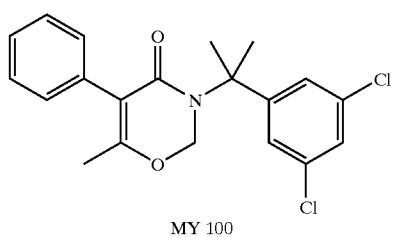

MY 100 with the proviso that
ii) compositions which comprise
A") at least one compound from the group of the substituted phenylsulfonylureas of the formula I" and their agriculturally accepted salts (I")

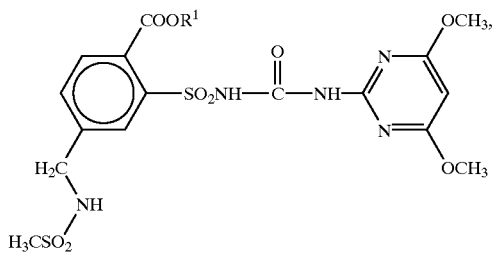

in which
R$^1$ is (C$_1$–C)-alkyl, (C$_3$–C$_4$)-alkenyl, (C$_3$–C$_4$)-alkyl or (C$_1$–C$_4$)-alkyl, which is mono- to tetrasubstituted by radicals from the group consisting of halogen and (C$_1$–C$_2$)-alkoxy
in combination with
B") fenoxaprop, pendimethalin, mecoprop, MCPA, 2,4-D, dicamba, a compound of the abovementioned formula III, bentaxon, ioxynil, metosulam, or metsulfuron as the only herbicidally active compounds,
are excluded.

2. The herbicidal composition as claimed in claim 1 wherein the herbicide of the formula (I) or its salts, R$^1$ is methyl.

3. The herbicidal composition as claimed is claim 1, wherein,
in the herbicide of the formula (I) or its salt R$^1$ is methyl, ethyl, n- or isopropyl, n-, tert-, 2-butyl isobutyl, n-pentyl, isopentyl, n-hexyl, isohexyl, 1,3-dimethylbutyl, n-heptyl, 1-methylhexyl or 1,4-dimethylpentyl;

R$^2$ is CH$_2$NHSO$_2$CH$_3$;

R$^3$ is methoxy; and

Z is CH.

4. The herbicidal composition as claimed in claim 3, wherein
in the herbicide of the formula (I) or its salts R$^1$ is methyl.

5. The herbicide composition as claimed in claim 4, wherein
the composition comprises the compounds A2)

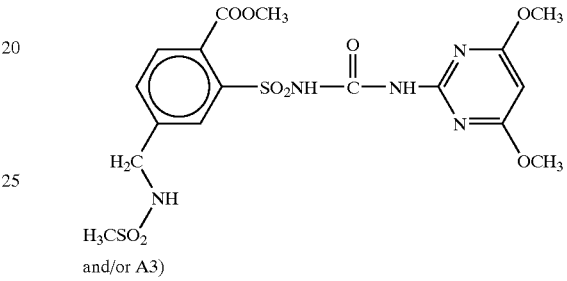

and/or A3)

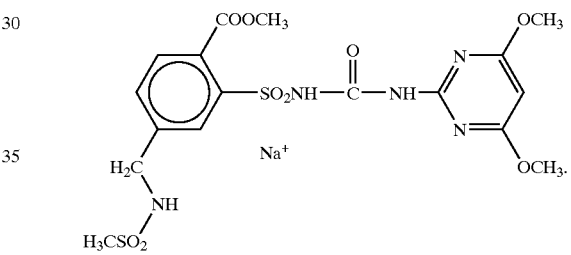

6. The herbicidal composition as claimed in claim 1, wherein
the salt of the herbicide of the formula (I) is formed by replacing the hydrogen of the —SO$_2$—NH— group by a cation from the group of the alkali metals, alkaline earth metals and ammonium.

7. The herbicidal composition as claimed in claim 6, wherein the cation is sodium.

8. The herbicidal composition as claimed in claim 1, wherein
the composition comprises, as herbicides of group 3, one or more herbicides which are selective in rice, mainly against grasses that are selected from the group consisting of chloracetanilides, thiocarbamates, quinolinecarboxylic acids, cyclohexanediones, cyclohexanedione oximes, NBA061, organophosphorus compounds, 2-(4-aryloxyphenoxy)propionic acids, or their esters, ureas, pyridincarbothioates, butyramides, menthyl benzyl ethers and triazoles.

9. The herbicidal composition as claimed in claim 8 wherein
the composition comprises, as herbicides of group B, at least on herbicide selected from the group consisting of B1)
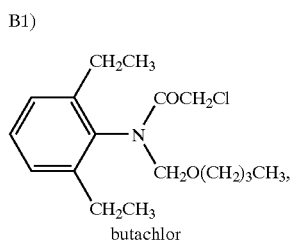
butachlor
B2)
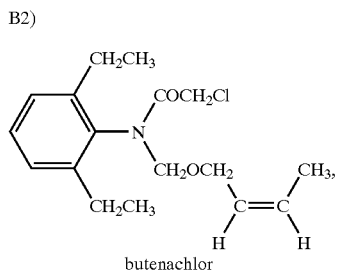
butenachlor
B3)
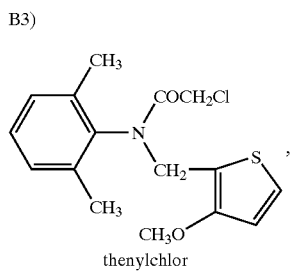
thenylchlor
B4)
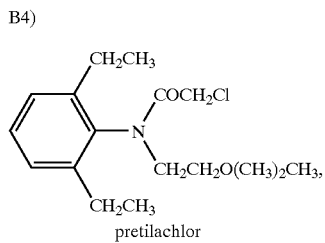
pretilachlor
B5)
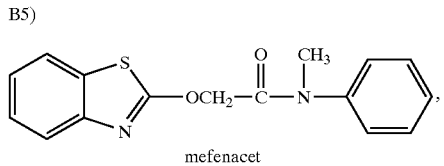
mefenacet
B5a)
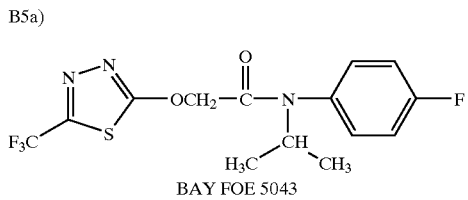
BAY FOE 5043
B6)
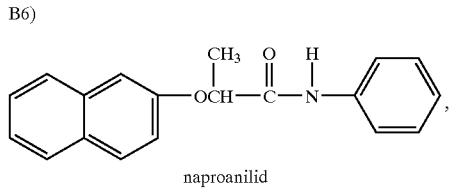
naproanilid
B7)
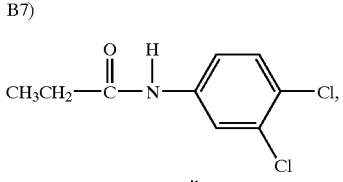
propanil
B8)
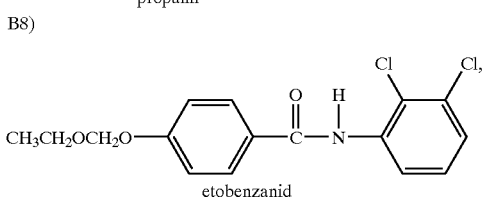
etobenzanid
B9)
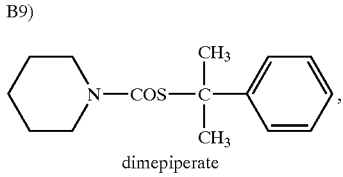
dimepiperate
B10)
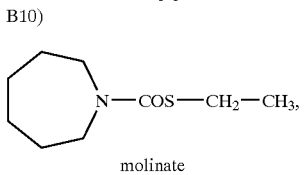
molinate
B11)
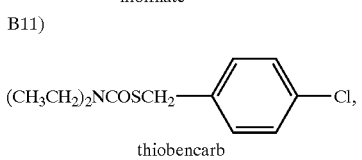
thiobencarb
B12)
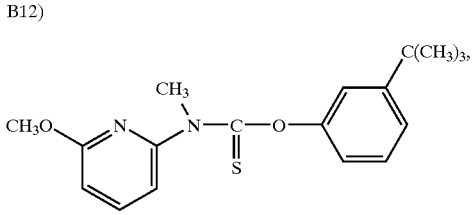
pyributicarb
B13)
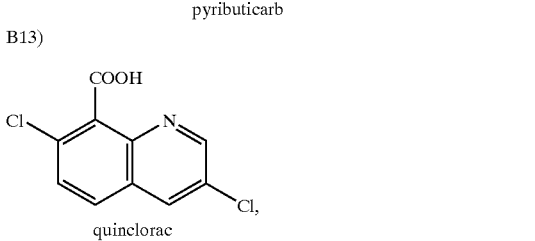
quinclorac
B14)
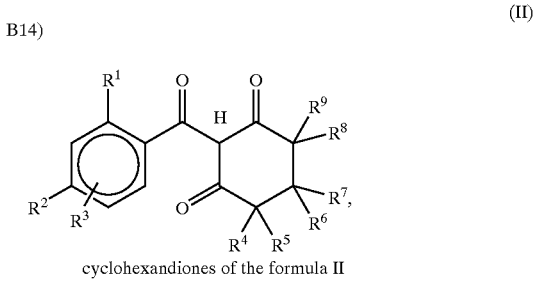
cyclohexandiones of the formula II
(II)

in which

R[1] is halogen ($C_1$–$C_4$)-alkoxy, ($C_1$–$C_4$)-alkyl, ($C_1$–$C_4$)-haloalkyl, —$NO_2$, —CN or $S(O)_n R^{10}$;

R[2] and R[3] independently of one another are hydrogen, halogen, ($C_1$–$C_4$)-alkyl, ($C_1$–$C_4$)-alkoxy, ($C_1$–$C_4$)-haloalkoxy, ($C_1$–$C_4$)-haloalkyl, —$NO_2$, —CN or $S(O)_m R^{11}$, —$NR^{12}R^{13}$, —$NR^{14}$—CO—$R^{15}$;

R[4] is hydrogen, ($C_1$–$C_4$)-alkyl or —CO—O—($C_1$–$C_4$)-alkyl;

R[5], R[6], R[7], R[8], R[9] independently of one another are hydrogen or ($C_1$–$C_4$)-alkyl or —CO—$R^{16}$;

R[10] is ($C_1$–$C_4$)-alkyl, ($C_1$–$C_4$)-haloalkyl, phenyl, benzyl or —$NR^{17}R^{18}$;

R[12] and R[13] independently of one another are hydrogen or ($C_1$–$C_4$)-alkyl;

R[14] is hydrogen or ($C_1$–$C_4$)-alkyl;

R[15] is ($C_1$–$C_4$)-alkyl;

R[16] is hydrogen, ($C_1$–$C_4$)-alkyl, ($C_1$–$C_4$)-haloalkyl or ($C_1$–$C_4$)-alkoxy;

R[17] and R[18] independently of one another are hydrogen or ($C_1$–$C_4$)-alkyl; and n and m independently of one another are 0, 1 or 2,

B15)

cycloxydim

B16)

sethoxydim

B17)

Bayer NBA 061

B18)

piperophos

B19)

anilofos

B20)

fenoxaprop, fenoxaprop-P

B21)

haloxyfop

B22)

cyhalofop

B23)

JC-940

B24)

dithiopyr

B25)

bromobutide

B26)

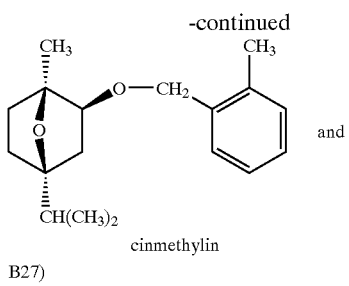
cinmethylin

B27)
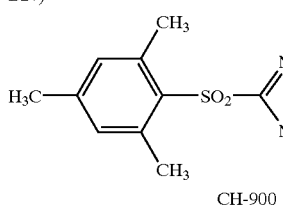
CH-900

10. The herbicidal composition as claimed in claim 5, wherein the composition comprises, as herbicides of group B, at least one herbicidal selected from the group consisting of anilofos, fenoxaprop, fenoxaprop-P, butachlor and propanil.

11. The herbicidal composition as claimed in claim 1, wherein the composition comprises, as herbicides of group B, one or more herbicides which are selective in rice, mainly against dicotyledonous harmful plants and cyperaceae, that are selected from the group consisting of aryloxyalkylcarboxylic acids, dicamba, nitrodiphenylethers, azoles, pyrazoles, sulfonylureas, hydroxybenzonitriles, pyridincarboxylic acids and triazoles.

12. The herbicidal composition as claimed in claim 10 wherein the composition comprises, as herbicides of group B, at least one herbicide selected from the group consisting of B28)
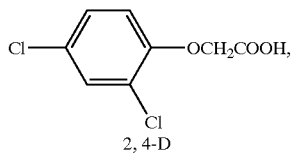
2,4-D B29)
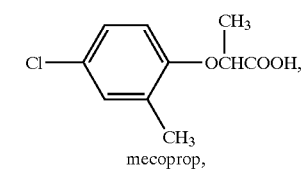
mecoprop,

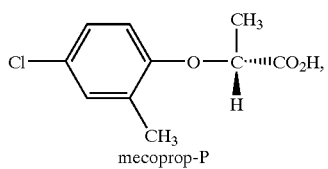
mecoprop-P

B30)
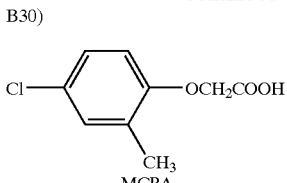
MCPA

B31)
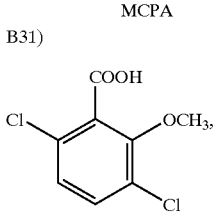
dicamba

B32)
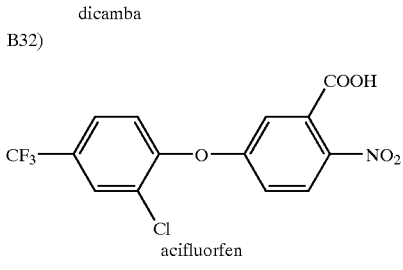
acifluorfen

B33)

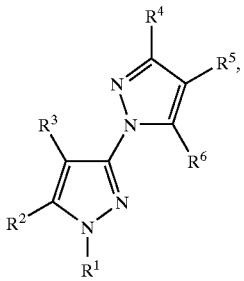
azoles of the formula III in which $R^1$ is $(C_1-C_4)$-alkyl, $R^2$ is $(C_1-C_4)$-alkyl, $(C_1-C_4)$-alkylthio or $(C_1-C_4)$-alkoxy, each radical of which may be substituted by one or more halogen atoms, or $R^1$ and $R^2$ together form the group $(CH_2)_m$ where m=3 or 4, $R^3$ is hydrogen or halogen, $R^4$ is hydrogen or $(C_1-C_4)$-alkyl, $R^5$ is hydrogen, nitro, cyano or one of the groups —$COOR^7$, —$C(=X)NR^7R^8$ or —$C(=X)R^{10}$, $R^6$ is hydrogen, cyano, $(C_1-C_4)$-alkyl, $(C_1-C_4)$-alkylthio or —$NR^{11}R^{12}$, $R^7$ and $R^8$ are identical or different and are hydrogen or $(C_1-C_4)$-alkyl, or $R^7$ and $R^8$ together with the nitrogen to which they are attached form a saturated 5- or 6-membered carbocyclic ring, $R^{10}$ is hydrogen or $(C_1-C_4)$-alkyl, where the latter may be unsubstituted or substituted by one or more halogen atoms, and $R^{11}$ and $R^{12}$ are identical or different and are hydrogen, $(C_1-C_4)$-alkyl or $(C_1-C_4)$-alkoxycarbonyl, where $R^{11}$ and $R^{12}$ together with the nitrogen to which they are attached may form a 3-, 5-, or 6-membered carbocyclic or aromatic ring in which one carbon atom may optionally be replaced by and oxygen atom, B34)
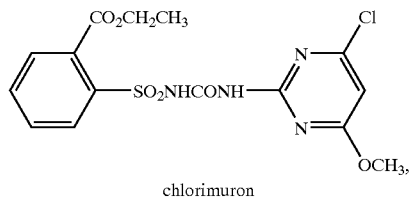
chlorimuron B35)
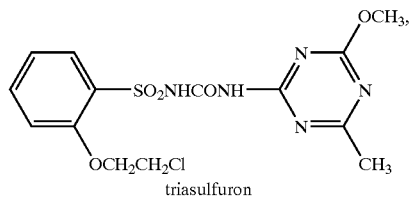
triasulfuron B36)
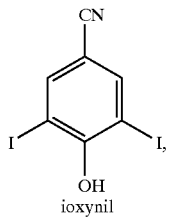
ioxynil B37)
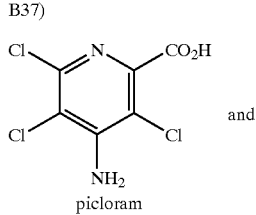
and
picloram B38)
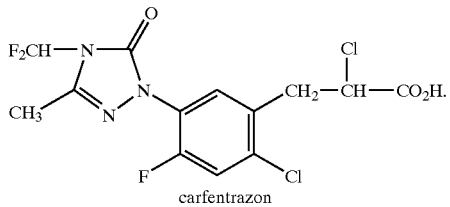
carfentrazon 13. The herbicidal composition as claimed in claim one or more of the preceding claims 5, wherein,
the composition comprises, at least one herbicide selected from the group consisting of 2,4-D, MCPA, mecoprop and dicamba.

14. The herbicidal composition as claimed in claim 1, wherein
the composition comprises, as herbicides of group B, one or more herbicides which are selective in rice, mainly against cyperaceae, that are selected from the group consisting of bentazon, triclopyr, benzofuranyl compounds and ureas.

15. The herbicidal composition as claimed in claim 14, wherein
the composition comprises, as herbicides of group B, at least one herbicide selected from the group consisting of B39)
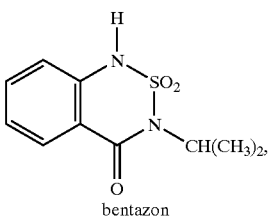
bentazon B40)
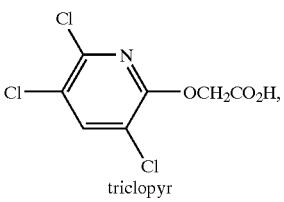
triclopyr B41)
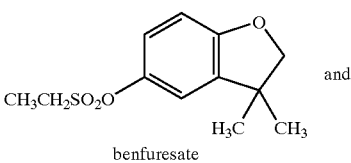
and
benfuresate B42)
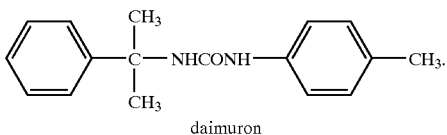
daimuron 16. The herbicidal composition as claimed in claim 5, wherein
the composition comprises, as herbicides of group B, at least one herbicide selected from the group consisting of bentazon and daimuron.

17. The herbicidal composition as claimed in claim 1, wherein,
the composition comprises, as herbicides of group B, one or more herbicides which are selective in rice against grasses and dicotyledonous harmful plants on cyperacae that are selected from the group consisting of 2,6-dinitroanilines, pyrazoles, pyrimidinyloxobenzoic acids, oxadiazoles, anilides, diphenyl ethers, alkylcarboxylic acids, sulfonylureas given in formula I, 1,3,5-triazines, pyridines, organophosphorus compounds, pentoxazon, indanofan, LGC40863 and MY100.

18. The herbicidal composition as claimed in claim 17, wherein
the composition comprises, as herbicides of group B, at least one herbicide selected from the group consisting of B43)
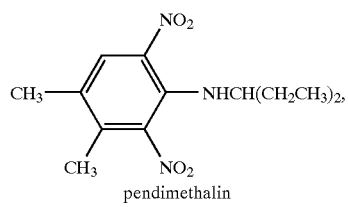
pendimethalin
B44)
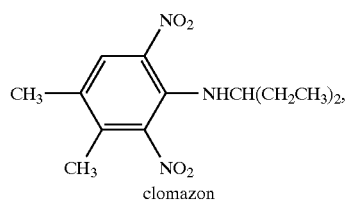
clomazon
B45)
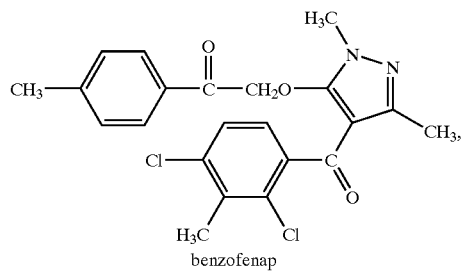
benzofenap
B46)
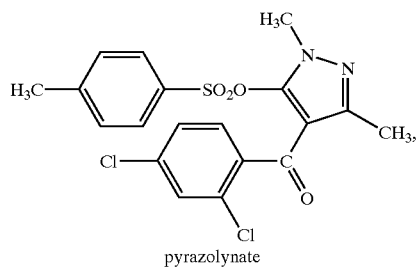
pyrazolynate
B47)
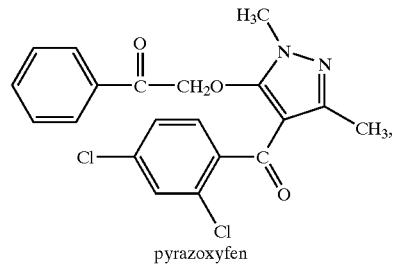
pyrazoxyfen
B48)
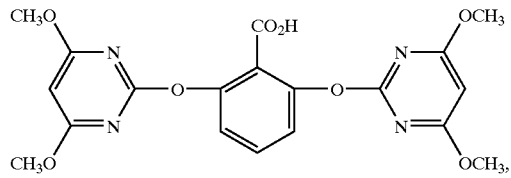
KIH 2023
-continued
B49)
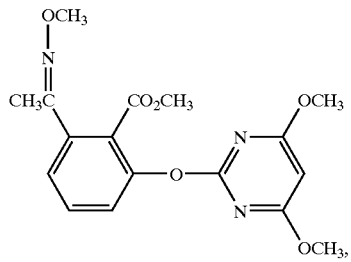
KIH 5127
B50)
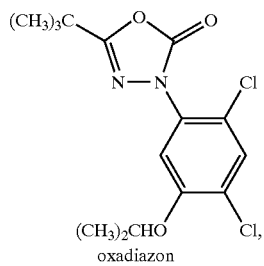
oxadiazon
B51)
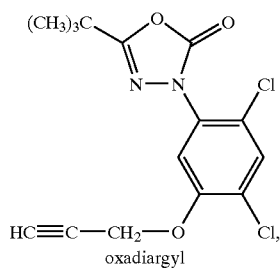
oxadiargyl
B52)
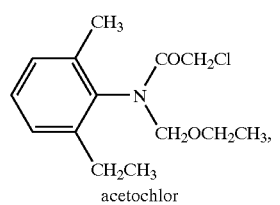
acetochlor
B53)
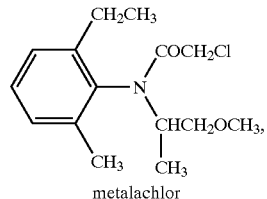
metalachlor
B54)
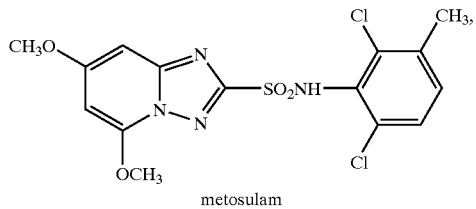
metosulam -continued B55)
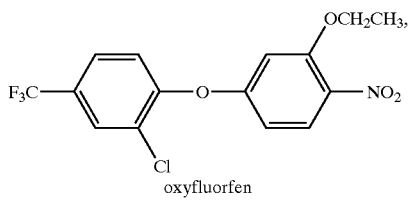
oxyfluorfen B56)
CH₃CCl₂CO₂H,
dalapon B57)
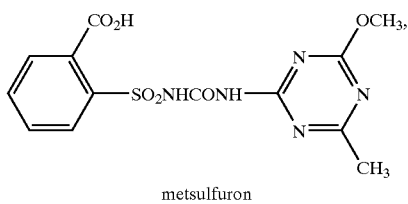
metsulfuron B58)
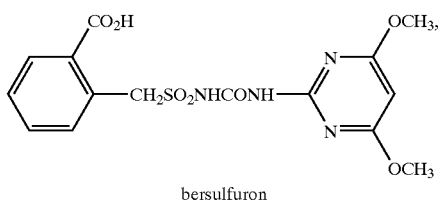
bersulfuron B59)
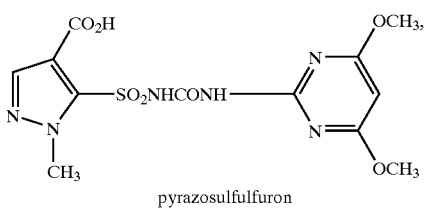
pyrazosulfulfuron B60)
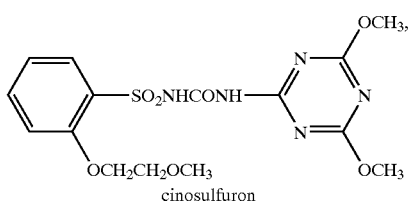
cinosulfuron B61)
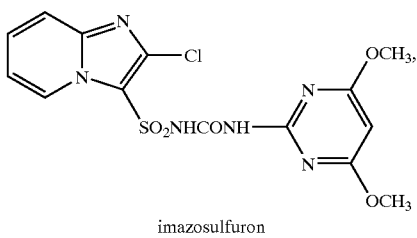
imazosulfuron -continued B62)
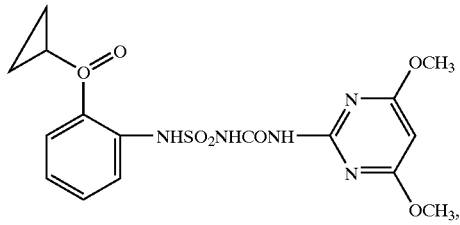
AC 322, 140 (cyclosulfamuron)

B63)
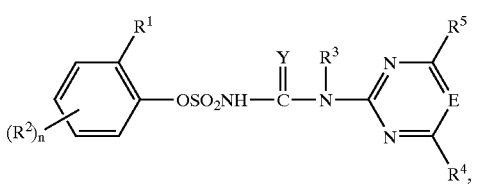
sulfonylureas of the formula IV in which a) $R^1$ is ethoxy, propoxy or isopropoxy and $R^2$ is halogen, $NO_2$, $CF_3$, CN, $(C_1-C_4)$-alkyl, $(C_1-C_4)$-alkoxy, $(C_1-C_4)$-alkylthio or $((C_1-C_4)$-alkoxy)carbonyl and n is 0, 1, 2, or 3 or b) $R^1$ is saturated or unsaturated $(C_1-C_6)$-alkoxy, which is substituted by halogen, saturated or unsaturated $(C_1 14 C_6)$-alkoxy, a radical of the formula $(((C_1-C_6)$-alkyl)-S—, $((C_1-C_6)$-alkyl)-O—CO—, $NO_2$, CN or phenyl; furthermore $(C_2-C_8)$-alkenyloxy or -alkynyloxy and $R^2$ is saturated or unsaturated $(C_1-C_8)$-alkyl, phenyl, phenoxy, $(C_1-C_4)$-alkoxy, $(C_1-C_4)$-alkylthio, $((C_1-C_4)$-alkoxy)carbonyl, where all of the abovementioned radicals $R^2$ may be substituted by halogen, $(C_1-C_4)$-alkoxy or $(C_1-C_4)$-alkylthio, or halogen, $NO_2$, $(C_1-C_4)$-alkylsulfonyl or -sulfinyl and n is 0, 1, 2 or 3 or c) $R^1$ is $(C_1-C_8)$-alkoxy and $R^2$ is $(C_2-C_8)$-alkenyl or -alkynyl, phenyl, phenoxy, where the radicals mentioned above for $R^2$ are unsubstituted or substituted by halogen, $(C_1-C_4)$-alkoxy or $(C_1-C_4)$-alkylthio, or $(C_1-C_4)$-alkylsulfonyl or -sulfinyl and n is 1, 2, or 3 or d) $R^1$ is, in each case in the 2-position on the phenyl radical, halogen, methoxy, ethyl or propyl, $R^2$ is $((C_1-C_4)$-alkoxy)carbonyl in the 6-position on the phenyl radical and n=1 and in all cases a) to d)

$R^4$, $R^5$ independent of one another are hydrogen, halogen, $(C_1-C_4)$-alkylthio, where the three last-mentioned radicals are unsubstituted or substituted by halogen, $(C_1-C_4)$-alkoxy or $(C_1-C_4)$-alkylthio, Y is O or S and
E is CH or N,
B64)
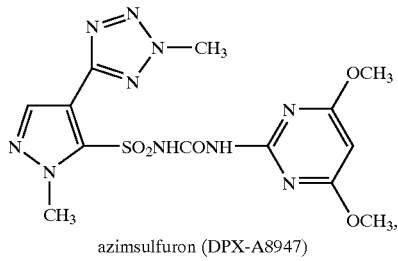
azimsulfuron (DPX-A8947)
B65)
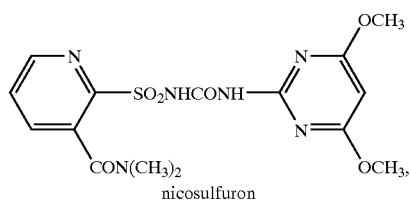
nicosulfuron
B66)
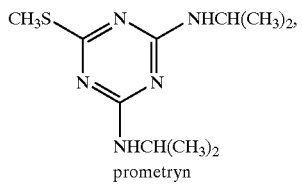
prometryn
B67)
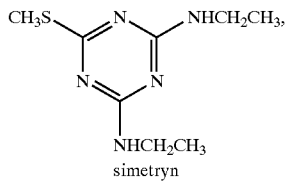
simetryn
B68)
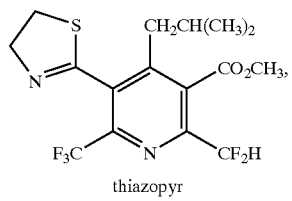
thiazopyr
B69)
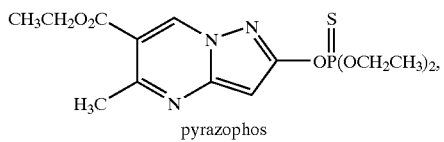
pyrazophos
-continued
B70)
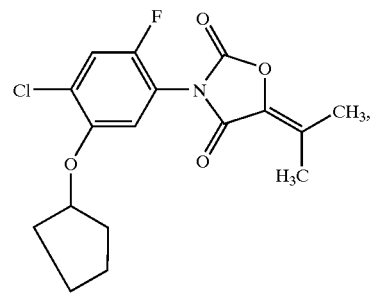
pentoxazone
B71)
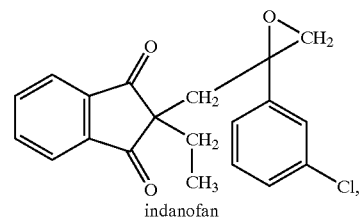
indanofan
B72)
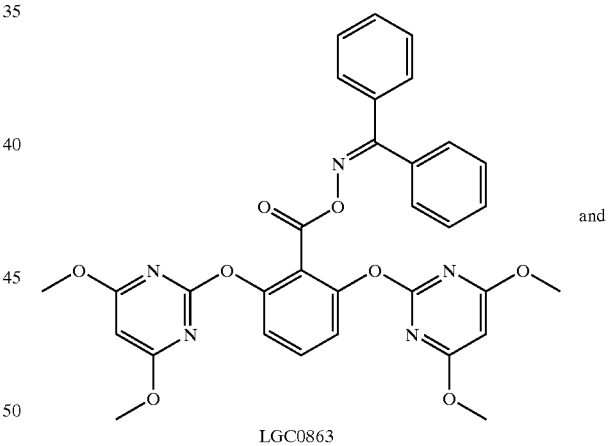
LGC0863
and
B73)
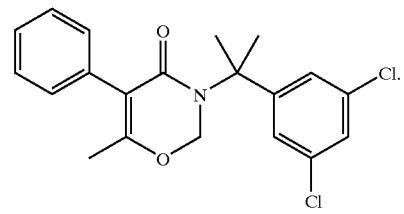
MY 100

19. The herbicidal composition as claimed in claim 1, wherein
the composition comprises the compounds of the formula I or their salts (group A compounds) and the compound from group B in a weight ratio of from 1:20,000 to 200:1.

20. The herbicidal composition as claimed in claim 19, wherein
the weight ratio is from 1:8000 to 100:1.

21. The herbicidal composition as claimed in claim 19, wherein
the weight ratio is from 1:4000 to 50:1.

22. The composition as claimed in claim 1, wherein
the composition comprises from 0.1 to 99% by weight of the active compounds A and B, in addition to customary formulation auxiliaries.

23. A herbicidal composition, comprising a synergistic amount of B) at least on herbicidally active compound from the group of the substituted phenylsulfonylureas of the formula I and their agriculturally accepted, i.e., acceptable and compatible, salts

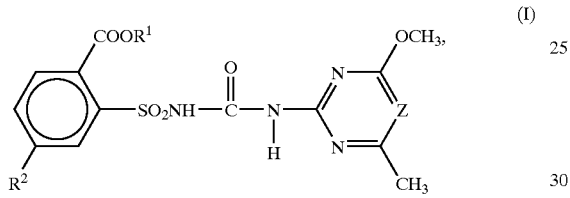

in which
$R^1$ is $(C_1-C_8)$-alkyl, $(C_3-C_4)$-alkenyl, $(C_3-C_4)$-alkynyl or$(C_1-C_4)$-alkyl, which is mono- to tetrasubstituted by radicals from the group consisting of halogen and $(C_1-C_2)$-alkoxy;
$R^2$ is I or $(H_2NHSO_2CH_3)$ when
Z CH
or
$R^2$ is $CH_2NHSO_2CH_3$ when
Z is N
$R^3$ is methyl or methoxy,
in combination with
at least one herbicidally active compound from the group of the compounds B consisting of
B1) butachlor,
B2) butenachlor,
B3) thenylchlor
B4) pretilachlor
B5) mefenacet,
B5a) Bay FOE 5043
B6) naproanilid,
B7) propanil,
B8) etonenzanid,
B9) dimepiperate,
B10) molinate,
B11) thiobencarb
B12) pyributicarb,
B13) quinclorac,
B14a) sulcotrione
B15) cycloxydim
B16) sethoxydim B17) NBA 061
B18) piperophos,
B19) anilofos
B21) haloxyfop,
B22) cyhalofop,
B23) JC-940,
B24) dithiopyr,
B25) bromobutide,
B26) cinmethylin,
B27) CH-900,
B32) acifluorfen
B34) chlorimuron,
B37) picloram,
B38) carfentrazon,
B40) triclopyr,
B41) benfuresate,
B42) daimuron,
B44) clomazon,
B45) benzofenap,
B46) pyrazolnyate,
B47) pyrazoxyfen,
B49) KIH 6127
B50) oxadiazon,
B51) oxadiargyl,
B56) bensulfuron,
B58) bensulfuron,
B59) pyrazolsulfuron,
B60) cinosulfuron,
B61) imazosulfuron,
B62) AC 322, 140 (cyclosulfamuron)
B63a) ethoxysulfuron (HOE 095404)
B64) azimsulfuron (DPX-A8947)
B66) prometryn,
B67) simetryn,
B68) thiazopyr,
B69) pyrazophos,
B70) pentoxazone,
B71) indanofan,
B72) LGC 40863
and
B73) MY 100
or in connection with two or more herbicidally active compounds from the group of the compounds B" consisting of
B1) butenachlor,
B2) butenachlor,
B3) thenylchlor,
B4) pretilachlor,
B5) mefenacet,
B5a) Bay FOE 5043,
B6) naproanilid,
B7) propanil,
B8) etobenzanid,
B9) dimepiperate,
B10) molinate,
B11) thiobencarb
B12) pyributicarb, B13) quinclorac,
B14a) sulcotrione,
B15) cycloxydim,
B16) sethoxydim,
B17) NBA 061,
B18) piperophos,
B19) anilofos,
B20) fenoxaprop, fenoxaprop-P
B21) haloxyfop,
B22) cyhalofop,
B23) JC-940
B24) dithiopyr,
B25) bromobutide,
B26) cinmethylin,
B27) CH-900,
B30) MCPA,
B31) dicamba,
B32) acifluorfen,

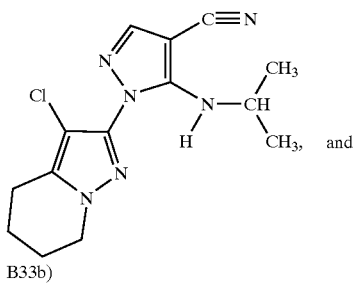

B33a)

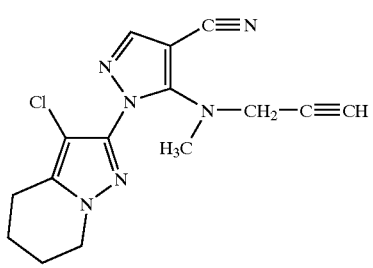

B33b)

B34) chlorimuron
B35) triasulfuron,
B36) ioxynil,
B37) picloram,
B38) carfentrazon,
B39) bentazon,
B40) triclopyr,
B41) benfuresate,
B42) daimuron,
B43) pendimethalin,
B44) clomazon,
B45) benzofenap,
B46) pyrazolynate,
B47) pyazoxyfen,
B48) KIH 2023,
B49) KIH 6127,
B50) oxadiazon, B51) oxadiargyl,
B52) acetochlor,
B53) metolachlor,
B54) metosulam,
B55) oxyfluorfen,
B56) dalapon
B57) metsulfuron,
B58) bensulfuron,
B60) cinosulfuron,
B61) imazosulfuron,
B62) AC 322, 140 (cyclosulfamuron),
B63a) ethoxysulfuron (HOE 095404),
B64) azimsulfuron (DPX-A8947)
B65) nicosulfuron,
B66) prometryn,
B67) simetryn,
B66) prometryn,
B67) simetryn,
B68) thiazopyr,
B69) pyrazophos,
B70) pentoxazone,
B71) indanofan,
B72) LGC 40863 and
B73) MY 100 wherein in the case B" at least one of the compounds from the group B" also has to belong to B'.

24. The herbicidal composition as claimed in claim 5, which comprises at Least one group B herbicide selected from the group consisting of B14a)

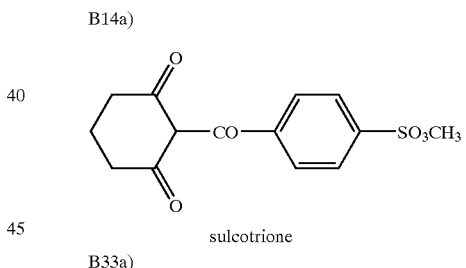

sulcotrione

B33a)

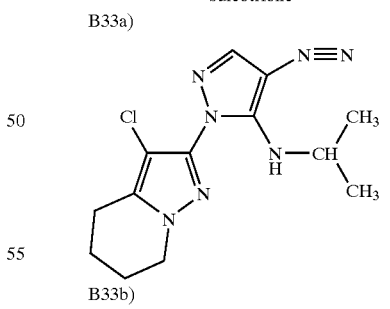

B33b)

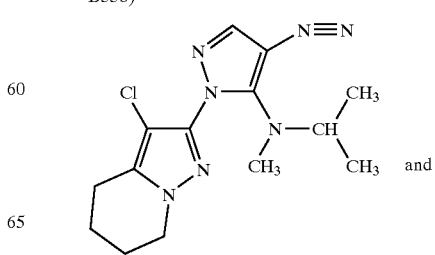

and

B63a)

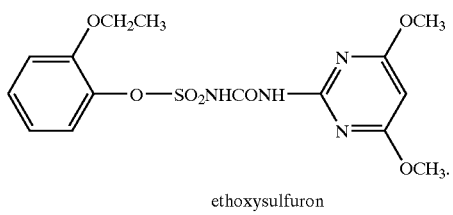

ethoxysulfuron

25. A process for preparing a herbicidal composition as claimed in claim 1 which comprises, formulating the compounds of the formula I or their salts (group A compounds) with one or more compounds of group B analogously to a customary crop protection formulation selected from the group consisting of wettable powders, emulsifiable concentrates, aqueous solution, emulsions, sprayable solutions (tank mix), oil- or water-based dispersions, suspoemulsions, dusting agents, seed dressings, granules for soil application or application by broadcasting, water-dispersible granules, ULV formulations, microcapsules and waxes.

26. A method for controlling undesirable plants, which comprises, applying a herbicidally effective amount of herbicide compositions according to claim 1, to the undesirable plants or to the area under cultivation.

27. The method as claimed in claim 26, wherein the application rate for the compounds of the formula (I) or their salts (group A compounds) is from 0.1 to 100 g of ai/ha, and the application rates for the compounds of group B are from 1 to 5000 g of ai/ha.

28. The method as claimed in claim 27, wherein the application rate for the compounds of group A are from 0.5 to 60 g of ai/ha.

29. The method as claimed in claim 27, wherein the application rate for the compounds of group A is from 2 to 40 g of ai/ha.

30. The method as claimed in claim 26, wherein the active compounds of types A and B are supplied simultaneously or at different times in a weight ratio of from 1:20,000 to 200:1.

31. The method as claimed in claim 26, wherein the combinations are employed for the selective control of undesirable plants.

32. The method as claimed in claim 31, wherein the combinations are employed in transgenic crops.

33. The method as claimed in claim 31, wherein the combinations are employed in rice.

34. A method for controlling undesirable harmful plants in rice crops which comprises applying to said harmful plants or to an area where they reside an effective amount of a herbicidal composition comprising:

A) at least one herbicidally active compound from the group of the substituted phenylsulfonylureas of the formula I and their agriculturally accepted, salts

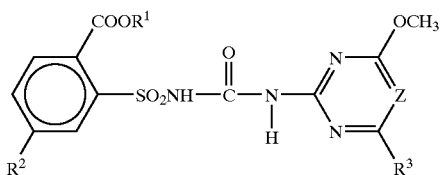

in which
$R^1$ is $(C_1-C_8)$-alkyl, $(C_3-C_4)$-alkenyl, $(C_3-C_4)$-alkynyl or $(C_1-C_4)$-alkyl, which is mono- to tetrasubstituted by radicals selected from the group consisting of halogen and/or $(C_1-C_2)$-alkoxy;

$R^2$ is I or $CH_2NHSO_2CH_3$ when
Z is CH
or
$R^2$ is $CH_2NHSO_2CH_3$ when
Z is N
$R^3$ is methyl or methoxy,
and
B) at least on herbicidally active compound from the group of the compounds consisting of
Ba) herbicides which are selective in rice against grasses selected from the group consisting of
B1) butachlor,
B2) butenachlor,
B3) thenylchlor,
B4) pretilachlor,
B5) mefenacet,
B5a) Bay FOE 5043,
B6) naproanilid,
B7) propanil,
B8) etobenzanid,
B9) dimepiperate,
B10) molinate,
B11) thiobencarb,
B12) pyributicarb,
B13) quinclorac,
B14) cyclohexandiones of the formula II t,2121
in which
$R^1$ is halogen, $(C_1-C_4)$-alkoxy, $(C_1-C_4)$-alkyl, $(C_1-C_4)$-haloalkyl, $-NO_2$, $-CN$ or $S(O)_nR^{10}$;
$R^2$ and $R^3$ independently of one another are hydrogen, halogen, $(C_1-C_4)$-alkyl, $(C_1-C_4)$-alkoxy, $(C_1-C_4)$-haloalkoxy, $(C_1-C_4)$-alkyl, $(C_1-C_4)$-alkoxy, $(C_1-C_4)$-haloalkyl, $(C_1-C_4)$-haloalkyl, $-NO_2$, $-CN$ or $S(O)_mR^{11}$, $-NR^{12}R^{13}$, $-NR^{14}-CO-R^{15}$;
$R^4$ is hydrogen, $(C_1-C_4)$-alkyl or $-CO-O-(C_1-C_4)$-alkyl;
$R^5,R^6,R^7,R^8,R^9$, independently of one another are hydrogen or $(C_1-C_4)$-alkyl or $-CO-R^{16}$;
$R^{10}$ is $(C_1-C_4)$-alkyl, $(C_1-C_4)$-haloalkyl or $(C_1-C_4)$-alkoxy;
$R^{11}$ is $(C_1-C_4)$-alkyl, $(C_1-C_4)$-haloalkyl, phenyl, benzyl or $-NR^{17}R^{18}$;
$R^{12}$ and $R^{13}$ independently of one another are hydrogen or $(C_1-C_4)$-alkyl;
$R^{14}$ is hydrogen or $(C_1-C_4)$-alkyl
$R^{15}$ is $(C_1-C_4)$-alkyl;
$R^{16}$ is hydrogen, $(C_1-C_4)$-alkyl, $(C_1-C_4)$-haloalkyl or $(C_1-C_4)$-alkoxy;
$R^{17}$ and $R^{18}$ independently or one another are hydrogen or $(C_1-C_4)$-alkyl; and
n and m independently or one another are 0, 1 or 2,
B15) sethoxydim
B16) NBA 061,
B17) piperophos,
B18) anilofos,
B19) fenoxaprop, fenoxaprop-P,
B20) haloxyfop, B21) cyhalofop,
B22) JC-940
B23) dithiopyr,
B24) bromobutide,
B25) cinmethylin and
B26) CH-900,
Bb) herbicides which are selective in rice against dicotyledonous harmful plants and cyperaceae selected from the group consisting of
B27) 2,4-D,
B28) mecoprop, mecoprop-P,
B29) MCPA,
B30) dicamba,
B31) acifluorfen, B33a)

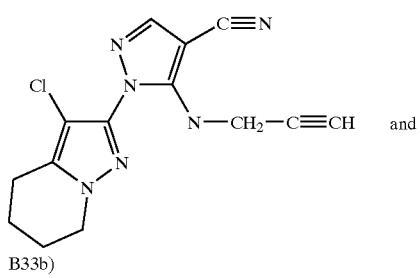

B33b)

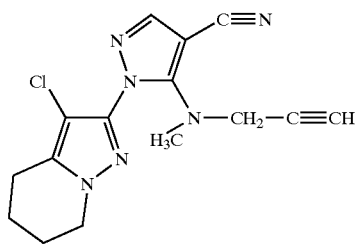

B34) chlorimuron,
B35) triasulfuron,
B36) ioxynil
B37) picloram and
B38) carfentrazon,
Bc) herbicides which are selective in rice against cyperaceae selected from the group consisting of
B39) bentazon,
B40) triclopyr,
B41) benfuresate, and
B42) daimuron,
Bb) herbicides which are selective in rice against grasses and dicotyledonous harmful plants and harmful cyperaceae plants selected from the group consisting of B43) pendimethalin,
B44) clomazon,
B45) benzofenap,
B46) pyrazolynate,
B47) pyrazoxyfen,
B48) KIH 2023,
B49) KIH 6127
B50) oxadiazon,
B51) oxadiargyl,
B52) acetochlor,
B53) metolachlor,
B54) metosulam,
B55) oxyfluorfen,
B56) dalapon,
B57) metsulfuron,
B58) bensulfuron,
B59) pyrazosulfuron
B60) cinosulfuron,
B61) imazosulfuron,
B62) AC 322, 140 (cyclosulfamuron),
B63a) ethoxysulfuron (HOE 095404)
B64) azimsulfuron (DPX-A8947),
B65) nicosulfuron,
B66) prometryn,
B67) simetryn,
B68) thiazopyr,
B69) pyrazophos,
B70) pentoxazone,
B71) indanofan,
B72) LGC 40863 and
B73) MY 100,
in a weight ratio A:B in the range from 1:20,000 to 200:1.

35. The method as claimed in claim 34, wherein the amounts are synergistic.

36. The method as claimed in claim 34, wherein the herbicidal compositions comprise at least one compound from A) and at least one compound from Ba).

37. The method as claimed in claim 34, wherein the herbicidal compositions comprise at least one compound from A) and at least one compound from Bb).

38. The method as claimed in claim 34, wherein the herbicidal composition comprises at least one compound from A) and at least on compound from Bc).

39. The method as claimed in claim 34, wherein the herbicidal composition comprises at least one compound from A) and at least one compound from Bd).

* * * * *